United States Patent
Nunez et al.

(10) Patent No.: US 11,198,724 B2
(45) Date of Patent: Dec. 14, 2021

(54) TREATMENT OF STAPHYLOCOCCAL DISORDERS

(71) Applicants: THE REGENTS OF THE UNIVERSITY OF MICHIGAN, Ann Arbor, MI (US); Gabriel Nunez, Ann Arbor, MI (US); Jon Oscherwitz, Ann Arbor, MI (US); Kemp Cease, Ann Arbor, MI (US); Yumi Nakamura, Ann Arbor, MI (US); Tyler Nygaard, Bozeman, MT (US)

(72) Inventors: Gabriel Nunez, Ann Arbor, MI (US); Jon Oscherwitz, Ann Arbor, MI (US); Kemp Cease, Ann Arbor, MI (US); Yumi Nakamura, Ann Arbor, MI (US); Tyler Nygaard, Bozeman, MT (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/774,589

(22) PCT Filed: Mar. 14, 2014

(86) PCT No.: PCT/US2014/029768
§ 371 (c)(1),
(2) Date: Sep. 10, 2015

(87) PCT Pub. No.: WO2014/153241
PCT Pub. Date: Sep. 25, 2014

(65) Prior Publication Data
US 2016/0031973 A1    Feb. 4, 2016

Related U.S. Application Data

(60) Provisional application No. 61/784,476, filed on Mar. 14, 2013.

(51) Int. Cl.
*C07K 16/12* (2006.01)
*A61K 45/06* (2006.01)
(Continued)

(52) U.S. Cl.
CPC .......... *C07K 16/1271* (2013.01); *A61K 31/05* (2013.01); *A61K 31/18* (2013.01);
(Continued)

(58) Field of Classification Search
CPC ........ C12N 1/20; C12N 15/09; C12N 15/113; C07G 11/00; C12P 21/00; C07K 5/117;
(Continued)

(56) References Cited

U.S. PATENT DOCUMENTS 3,687,808 A    8/1972 Merigan et al.
5,432,272 A    7/1995 Benner
(Continued)

FOREIGN PATENT DOCUMENTS

CA    2842626 A1    1/2013
CN    101594859    * 12/2009 ........... A61K 31/192
(Continued)

OTHER PUBLICATIONS

Kretschmer, et al. ('Human Formyl Peptide Receptor 2 Senses Highly Pathogenic *Staphylococcus aureus*' (Cell Host & Microbe. Jun. 2010. vol. 7:463-473).*
(Continued)

*Primary Examiner* — Jana A Hines
(74) *Attorney, Agent, or Firm* — Marshall, Gerstein & Borun LLP

(57) ABSTRACT

Materials and methods are provided for treatment and/or prevention of Staphylococcal diseases and disorders such as infection and dermal inflammation.

30 Claims, 45 Drawing Sheets

Specification includes a Sequence Listing.

(51) Int. Cl.

| | | |
|---|---|---|
| A61K 31/05 | (2006.01) | |
| A61K 31/18 | (2006.01) | |
| A61K 31/192 | (2006.01) | |
| A61K 31/196 | (2006.01) | |
| A61K 31/235 | (2006.01) | |
| A61K 31/277 | (2006.01) | |
| A61K 31/47 | (2006.01) | |
| A61K 39/085 | (2006.01) | |
| A61K 31/37 | (2006.01) | |
| A61K 31/366 | (2006.01) | |
| A61K 31/713 | (2006.01) | |
| A61K 39/40 | (2006.01) | |
| C12N 15/113 | (2010.01) | |
| A61K 39/00 | (2006.01) | |

(52) U.S. Cl.
CPC .......... *A61K 31/192* (2013.01); *A61K 31/196* (2013.01); *A61K 31/235* (2013.01); *A61K 31/277* (2013.01); *A61K 31/366* (2013.01); *A61K 31/37* (2013.01); *A61K 31/47* (2013.01); *A61K 31/713* (2013.01); *A61K 39/085* (2013.01); *A61K 39/40* (2013.01); *A61K 45/06* (2013.01); *C12N 15/113* (2013.01); *A61K 2039/505* (2013.01); *A61K 2039/575* (2013.01); *C07K 2317/34* (2013.01); *C07K 2317/76* (2013.01); *C12N 2310/11* (2013.01); *C12N 2310/14* (2013.01); *C12N 2320/31* (2013.01)

(58) Field of Classification Search
CPC .......... C07K 5/11; C07K 5/097; C07K 16/12; C07K 7/06; A61K 38/00; A61K 38/06; A61K 38/07; A61K 38/08; A61P 37/08
See application file for complete search history.

(56) References Cited

U.S. PATENT DOCUMENTS

| | | | | |
|---|---|---|---|---|
| 8,680,147 | B2 * | 3/2014 | Raederstorff | A61K 8/37 514/569 |
| 2005/0249720 | A1 | 11/2005 | Perez | |

FOREIGN PATENT DOCUMENTS

| | | | | |
|---|---|---|---|---|
| EP | 1072679 A2 | | 1/2001 | |
| WO | WO 1995/005852 | * | 3/1995 | ............... A61K 8/64 |
| WO | WO-97/12896 A1 | | 4/1997 | |
| WO | WO 2005/075505 | * | 8/2005 | ............... C07L 5/097 |
| WO | WO-2005/075505 A1 | | 8/2005 | |
| WO | WO 2008/103751 | * | 8/2008 | ............... C12N 1/20 |
| WO | WO-2008/103751 A2 | | 8/2008 | |
| WO | WO 2009/095719 | * | 8/2009 | ............... A61P 37/08 |
| WO | WO-2009/095719 A2 | | 8/2009 | |
| WO | WO 2010051296 | * | 5/2010 | ............ A61K 31/235 |
| WO | WO 2012/031260 | * | 3/2012 | ............. C07K 16/12 |
| WO | WO-2012/031260 A2 | | 3/2012 | |
| WO | WO-2012031260 A2 | * | 3/2012 | ............... A61P 31/04 |

OTHER PUBLICATIONS

Liu et al., ('IgE, Mast Cells, and Eosinophils In Atopic Dermatitis'. Clin. Reviews in Allergy and Immunl. 2011. vol. 4; pp. 298-310).*
Marconi et al., (J. of Venomous Animals and Toxins including Tropical Diseases. Mar. 2005. vol. 11, No. 2: 117-128. Table 1. 'Standardization of the PCR Technique for the Detection of Delta Toxin in *Staphylococcus* spp.').*
Leung et al., (Acta Derm Venereol 2008. Suppl 216:21-27) (Year: 2008).*
Dahl, (Arch Dermatol. Oct. 1983;119(10):840-6). (Year: 1983).*
Hong et al., (Semin Cutan Med Surg. Jun. 2011; 30(2): 71-86) (Year: 2011).*
Leung et al., (J of Allergy and Clin Immunol. Sep. 1999; pp. S99-S108) (Year: 1999).*
Liu et al., ('IgE, Mast Cells, and Eosinophils In Atopic Dermatitis'. Clin. Reviews in Allergy and Immunl. 2011. vol. 4; pp. 298-310). (Year: 2011).*
Cogen et al., (PLOS One Jan. 2010, vol. 5. Issue 1, e8557, pp. 1-7) (Year: 2010).*
Oh et al., vol. 2012, Article ID 781375, 13 pages) (Year: 2012).*
Barman et al., Enteric salmonellosis disrupts the microbial ecology of the murine gastrointestinal tract, Infect. Immun., 76(3):907-15 (2008).
Chonn et al., Recent advances in liposomal drug-delivery systems, Curr. Opin. Biotechnol., 6(6):698-708 (1995).
Elias et al., "Outside-to-inside" (and now back to "outside") pathogenic mechanisms in atopic dermatitis, J. Invest. Dermatol., 128(5):1067-70 (2008).
Englisch et al., Chemically Modified Oligonucleotides as Probes and Inhibitors, Angewandte Chemie, International Edition, 30: 613-722 (1991).
Freier et al., The ups and downs of nucleic acid duplex stability: structure-stability studies on chemically-modified DNA:RNA duplexes, Nucleic Acids Res., 25(22):4429-43 (1997).
Galli et al., IgE and mast cells in allergic disease, Nat. Med., 18(5):693-704 (2012).
Galli et al., Phenotypic and functional plasticity of cells of innate immunity: macrophages, mast cells and neutrophils, Nat. Immunol., 12(11):1035-44 (2011).
Grimbaldeston et al., Mast cell-deficient W-sash c-kit mutant Kit W-sh/-sh mice as a model for investigating mast cell biology in vivo, Am. J. Pathol., 167(3):835-48 (2005).
Hasegawa et al., Differential release and distribution of Nod1 and Nod2 immunostimulatory molecules among bacterial species and environments, J. Biol. Chem., 281(39):29054-63 (2006).
International Preliminary Reporton Patentability, International Application No. PCT/US14/29768, dated Sep. 15, 2015.
International Search Report and Written Opinion, International Application No. PCT/US14/29768, dated Aug. 25, 2014.
Kawakami et al., Regulation of mast-cell and basophil function and survival by IgE, Nat. Rev. Immunol., 2(10):773-86 (2002).
Kozman et al., Encoding a superantigen by *Staphylococcus aureus* does not affect clinical characteristics of infected atopic dermatitis lesions, Br. J. Dermatol., 163(6):1308-11 (2010).
Kretschmer et al., Human formyl peptide receptor 2 senses highly pathogenic *Staphylococcus aureus*, Cell Host Microbe, 7(6):463-73 (2010).
Kroschwitz (ed.), The Concise Encyclopedia Of Polymer Science and Engineering, pp. 858-859, John Wiley & Sons, (1990).
Leung et al., A potential role for superantigens in the pathogenesis of psoriasis, J. Invest. Dermatol., 100(3):225-8 (1993).
Leung et al., Atopic dermatitis, Lancet, 361(9352):151-60 (2003).
Leung et al., Presence of IgE antibodies to staphylococcal exotoxins on the skin of patients with atopic dermatitis. Evidence for a new group of allergens, J. Clin. Invest., 92(3):1374-80 (1993).
Liu et al., IgE, mast cells, and eosinophils in atopic dermatitis, Clin. Rev. Allergy Immunol., 41 (3):298-310 (2011).
Marconi et al., Standardization of the PCR technique for the detection of delta toxin in *Staphylococcus* spp, J. Venomous Animals and Toxins including Tropical Diseases, 11 (2):117-28 (2005).
Miller et al., Amino acid requirements for the production of enterotoxin B by *Staphylococcus aureus* S-6 in a chemically defined medium, Appl. Microbiol., 25(5):800-6 (1973).
Neuber et al., Effects of *Staphylococcus aureus* cell wall products (teichoic acid, peptidoglycan) and enterotoxin B on immunoglobulin (IgE, IgA, IgG) synthesis and CD23 expression in patients with atopic dermatitis, Immunology, 75(1):23-8 (1992).
Nilsson et al., Alpha-toxin and gamma-toxin jointly promote *Staphylococcus aureus* virulence in murine septic arthritis, Infect. Immun., 67(3):1045-9 (1999).
Novick et al., Synthesis of staphylococcal virulence factors is controlled by a regulatory RNA molecule, EMBO J., 12(10):3967-75 (1993).

(56) References Cited

OTHER PUBLICATIONS

Queck et al., RNAIII-independent target gene control by the agr quorum-sensing system: insight into the evolution of virulence regulation in *Staphylococcus aureus*, Mol. Cell, 32(1):150-8 (2008).
Rudikoff et al., Atopic dermatitis, Lancet, 351 (9117):1715-21 (1998).
Sanghvi, Antisense Research and Application, Ed. S. T. Crooke and B. Lebleu, CRC Press, (1991).
Schmaler et al., Lipoproteins in *Staphylococcus aureus* mediate inflammation by TLR2 and iron-dependent growth in vivo, J. Immunol., 182(11):7110-8 (2009).
Seidl et al., Relationship of agr expression and function with virulence and vancomycin treatment outcomes in experimental endocarditis due to methicillin-resistant *Staphylococcus aureus*, Antimicrob. Agents Chemother., 55(12):5631-9 (2011).
Selander et al., TLR2/MyD88-dependent and -independent activation of mast cell IgE responses by the skin commensal yeast Malassezia sympodialis, J. Immunol., 182(7):4208-16 (2009).
Spergel et al., Epicutaneous sensitization with protein antigen induces localized allergic dermatitis and hyperresponsiveness to methacholine after single exposure to aerosolized antigen in mice, J. Clin. Invest., 101(8):1614-22 (1998).
Stoll et al., *Staphylococcus aureus* deficient in lipidation of prelipoproteins is attenuated in growth and immune activation, Infect. Immun., 73(4):2411-23 (2005).
Supajatura et al., Differential responses of mast cell Toll-like receptors 2 and 4 in allergy and innate immunity, J. Clin. Invest., 109(10):1351-9 (2002).
Wang et al., Identification of novel cytolytic peptides as key virulence determinants for community-associated MRSA, Nat. Med., 13(12):1510-4 (2007).
Wershil et al., Recruitment of neutrophils during IgE-dependent cutaneous late phase reactions in the mouse is mast cell-dependent. Partial inhibition of the reaction with antiserum against tumor necrosis factor-alpha, J. Clin. Invest., 87(2):446-53 (1991).
Williams et al., How epidemiology has challenged 3 prevailing concepts about atopic dermatitis, J. Allergy Clin. Immunol., 118(1):209-13 (2006).
Yamada et al., Generation of a large Number of connective tissue type mast cells by culture of murine fetal skin cells, J. Invest. Dermatol., 121 (6):1425-32 (2003).

* cited by examiner

| Staphylococcus strain | β-hex activity (%) |
|---|---|
| S.aureus (Newman) | 75.62 ± 6.12 *** |
| S.aureus (Newman Δlgt) | 59.58 ± 3.11 *** |
| S.aureus (8325-4) | 41.36 ± 1.90 *** |
| S.aureus (8325-4 Δcap5) | 34.24 ± 1.90 *** |
| S.aureus (SA113) | 7.27 ± 0.03 |
| S.saprophyticus | 16.99 ± 1.46 *** |
| S.epidermidis | 11.90 ± 1.72 * |
| S.xylosus | 8.38 ± 0.53 |
| S.sciuri | 4.15 ± 0.56 |
| S.cohnii | 5.07 ± 0.15 |
| S.succinus | 6.04 ± 1.38 |
| S.lentus | 5.76 ± 0.38 |
| S.fleuretti | 5.73 ± 0.28 |
| unstimulated MCs | 6.24 ± 0.18 |

*FIG. 5C*

| MC-degranulation activity | (%) |
|---|---|
| BHI sup +bacterial pellet | 100 |
| BHI sup | 120 |
| Washed bacterial pellet | 7.2 |
| sonicated bacterial pellet | 0 |
| RPMI sup | 17 |
| TSB sup | 55 |
| chemical medium sup | 13 |
| chemical medium + 2%Yeast Extract sup | 48 |
| boiling (100°C 30min) | 70 |
| (100°C over night) | 0 |
| acid (pH3) | 63 |
| alkaline (pH12) | 25 |
| phenol/chloroform | 0 |
| protenase K | 0 |

Chromatography

| | |
|---|---|
| DEAE-cellulose binding | Yes |
| CM-cellulose binding | Yes |
| gel filtration (pH 7.4) | void fraction |
| isoelectric pH (pI) | pH 8.8 |

*FIG. 6A*

|   | Protein Name | AA | total independent spectra | cover length (%) |
|---|---|---|---|---|
| 1 | δ-toxin | 26 | 121 | 100 |
| 2 | cysteine protease precursor, putative | 393 | 15 | 19.6 |
| 3 | hypothetical protein SAOUHSC00617 | 168 | 12 | 18.5 |
| 4 | lipase precursor | 690 | 11 | 7.4 |
| 5 | hypothetical protein SAOUHSC00094 | 199 | 3 | 25.1 |

*FIG. 6C*

Rabbit anti-DeltaC and DeltaN inhibit mast cell degranulation

SEQUENCE LISTING

<160> NUMBER OF SEQ ID NOS: 26

<210> SEQ ID NO 1
<211> LENGTH: 26
<212> TYPE: PRT
<213> ORGANISM: Staphylococcus aureus

<400> SEQUENCE: 1

Met Ala Gln Asp Ile Ile Ser Thr Ile Gly Asp Leu Val Lys Trp Ile
1               5                   10                  15

Ile Asp Thr Val Asn Lys Phe Thr Lys Lys
            20                  25

<210> SEQ ID NO 2
<211> LENGTH: 19
<212> TYPE: PRT
<213> ORGANISM: Staphylococcus aureus

<400> SEQUENCE: 2

Met Ala Gln Asp Ile Ile Ser Thr Ile Gly Asp Leu Val Lys Trp Ile
1               5                   10                  15

Ile Asp Thr

<210> SEQ ID NO 3
<211> LENGTH: 18
<212> TYPE: PRT
<213> ORGANISM: Staphylococcus aureus

<400> SEQUENCE: 3

Ile Gly Asp Leu Val Lys Trp Ile Ile Asp Thr Val Asn Lys Phe Thr
1               5                   10                  15

Lys Lys

<210> SEQ ID NO 4
<211> LENGTH: 11
<212> TYPE: PRT
<213> ORGANISM: Staphylococcus aureus

<400> SEQUENCE: 4

Ile Gly Asp Leu Val Lys Trp Ile Ile Asp Thr
1               5                   10

<210> SEQ ID NO 5
<211> LENGTH: 25
<212> TYPE: PRT
<213> ORGANISM: Staphylococcus epidermidis

<400> SEQUENCE: 5

Met Ala Ala Asp Ile Ile Ser Thr Ile Gly Asp Leu Val Lys Trp Ile
1               5                   10                  15

Ile Asp Thr Val Asn Lys Phe Lys Lys
            20                  25

<210> SEQ ID NO 6
<211> LENGTH: 25
<212> TYPE: PRT
<213> ORGANISM: Staphylococcus epidermidis

<400> SEQUENCE: 6

Met Ala Ala Asp Ile Ile Ser Thr Ile Gly Asp Leu Val Lys Trp Ile
1               5                   10                  15

Ile Asp Thr Val Asn Lys Phe Lys Lys
            20                  25

<210> SEQ ID NO 7
<211> LENGTH: 25
<212> TYPE: PRT
<213> ORGANISM: Staphylococcus warneri

<400> SEQUENCE: 7

Met Thr Ala Asp Ile Ile Ser Thr Ile Gly Asp Phe Val Lys Trp Ile
1               5                   10                  15

Leu Asp Thr Val Lys Lys Phe Thr Lys
            20                  25

<210> SEQ ID NO 8
<211> LENGTH: 25
<212> TYPE: PRT
<213> ORGANISM: Staphylococcus intermedius

```
<400> SEQUENCE: 8

Met Ala Ala Asp Ile Ile Ser Thr Ile Val Glu Phe Val Lys Leu Ile
1               5                   10                  15

Ala Glu Thr Val Ala Lys Phe Ile Lys
            20                  25

<210> SEQ ID NO 9
<211> LENGTH: 21
<212> TYPE: PRT
<213> ORGANISM: Artificial Sequence
<220> FEATURE:
<223> OTHER INFORMATION: Synthetic peptide -- fPSM alpha 2
<220> FEATURE:
<221> NAME/KEY: MISC_FEATURE
<222> LOCATION: (1)..(1)
<223> OTHER INFORMATION: N-terminal formyl-methionine

<400> SEQUENCE: 9

Met Gly Ile Ile Ala Gly Ile Ile Lys Val Ile Lys Ser Leu Ile Glu
1               5                   10                  15

Gln Phe Thr Gly Lys
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide fPSM alpha-3
<220> FEATURE:
<221> NAME/KEY: MISC_FEATURE
<222> LOCATION: (1)..(1)
<223> OTHER INFORMATION: N-terminal formyl-methionine

<400> SEQUENCE: 10

Met Gly Ile Ile Ala Gly Ile Ile Lys Phe Ile Lys Gly Leu Ile Glu
1               5                   10                  15

Lys Phe Thr Gly Lys
            20

<210> SEQ ID NO 11
<211> LENGTH: 26
<212> TYPE: PRT
<213> ORGANISM: Artificial Sequence
<220> FEATURE:
<223> OTHER INFORMATION: Synthetic peptide -- f delta-toxin --
      Staphylococcus aureus
<220> FEATURE:
<221> NAME/KEY: MISC_FEATURE
<222> LOCATION: (1)..(1)
<223> OTHER INFORMATION: N-terminal formyl-methionine

<400> SEQUENCE: 11

Met Ala Gln Asp Ile Ile Ser Thr Ile Gly Asp Leu Val Lys Trp Ile
1               5                   10                  15

Ile Asp Thr Val Asn Lys Phe Thr Lys Lys
            20                  25

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide -- WRWWWW-CONH2
<220> FEATURE:
<221> NAME/KEY: MISC_FEATURE
```

```
<222> LOCATION: (6)..(6)
<223> OTHER INFORMATION: C-terminal tryptophan amide

<400> SEQUENCE: 12

Trp Arg Trp Trp Trp Trp
1               5

<210> SEQ ID NO 13
<211> LENGTH: 13
<212> TYPE: PRT
<213> ORGANISM: Artificial Sequence
<220> FEATURE:
<223> OTHER INFORMATION: Synthetic peptide -- MMK-1

<400> SEQUENCE: 13

Leu Glu Ser Ile Phe Arg Ser Leu Leu Phe Arg Val Met
1               5                   10

<210> SEQ ID NO 14
<211> LENGTH: 21
<212> TYPE: DNA
<213> ORGANISM: Artificial Sequence
<220> FEATURE:
<223> OTHER INFORMATION: Synthetic primer -- Gapdh forward primer -- Mus
      musculus

<400> SEQUENCE: 14
cctcgtcccg tagacaaaat g                                                21

<210> SEQ ID NO 15
<211> LENGTH: 21
<212> TYPE: DNA
<213> ORGANISM: Artificial Sequence
<220> FEATURE:
<223> OTHER INFORMATION: Synthetic primer -- Gapdh reverse primer -- Mus
      musculus

<400> SEQUENCE: 15
tctccacttt gccacctgca a                                                21

<210> SEQ ID NO 16
<211> LENGTH: 40
<212> TYPE: DNA
<213> ORGANISM: Artificial Sequence
<220> FEATURE:
<223> OTHER INFORMATION: Synthetic polynucleotide -- Delta Barn --
      Bordetella pertussis

<400> SEQUENCE: 16
ctagatcaca gagatgtgat ggatcctagt tgatgagttg                            40

<210> SEQ ID NO 17
<211> LENGTH: 40
<212> TYPE: DNA
<213> ORGANISM: Artificial Sequence
<220> FEATURE:
<223> OTHER INFORMATION: Synthetic polynucleotide -- Delta Mlu --
      Bordetella pertussis

<400> SEQUENCE: 17
gttgggatgg cttaataacg cgtactttta gtactatacg                            40

<210> SEQ ID NO 18
<211> LENGTH: 62
<212> TYPE: DNA
<213> ORGANISM: Artificial Sequence
<220> FEATURE:
```

<223> OTHER INFORMATION: Synthetic polynucleotide -- HLDATT1 --
      Staphylococcus epidermidis

<400> SEQUENCE: 18
ggggacaagt tgtacaaaa aagcaggctt ggtacttctg gttcgtcaaa gtaagaggca    60
ca                                                                  62

<210> SEQ ID NO 19
<211> LENGTH: 61
<212> TYPE: DNA
<213> ORGANISM: Artificial Sequence
<220> FEATURE:
<223> OTHER INFORMATION: Synthetic polynucleotide -- HLDATT2 --
      Staphylococcus epidermidis

<400> SEQUENCE: 19
ggggaccact tgtacaaga aagctgggtg gcacttctgg ttcgtcaaag taagaagcac    60
a                                                                   61

<210> SEQ ID NO 20
<211> LENGTH: 34
<212> TYPE: DNA
<213> ORGANISM: Artificial Sequence
<220> FEATURE:
<223> OTHER INFORMATION: Sytnthetic polynucleotide -- HLD1 --
      Staphylococcus epidermidis

<400> SEQUENCE: 20
cgaaaggagt gaagttataa tagcagcaga tatc                               34

<210> SEQ ID NO 21
<211> LENGTH: 34
<212> TYPE: DNA
<213> ORGANISM: Artificial Sequence
<220> FEATURE:
<223> OTHER INFORMATION: Synthetic polynucleotide -- HLD2 --
      Staphylococcus epidermidis

<400> SEQUENCE: 21
gatatctgct gctattataa cttcactcct ttcg                               34

<210> SEQ ID NO 22
<211> LENGTH: 40
<212> TYPE: DNA
<213> ORGANISM: Artificial Sequence
<220> FEATURE:
<223> OTHER INFORMATION: Synthetic polynucleotide -- P3prEco --
      Staphylococcus aureus

<400> SEQUENCE: 22
caattttaca ccactctcct cactggaatt ccattatacg                         40

<210> SEQ ID NO 23
<211> LENGTH: 40
<212> TYPE: DNA
<213> ORGANISM: Artificial Sequence
<220> FEATURE:
<223> OTHER INFORMATION: Synthetic polynucleotide -- P3prBam --
      Staphylococcus aureus

<400> SEQUENCE: 23
atgcggatcc ctcatcaact attttccatc acatctctgt                         40

<210> SEQ ID NO 24
<211> LENGTH: 30

```
<212> TYPE: DNA
<213> ORGANISM: Artificial Sequence
<220> FEATURE:
<223> OTHER INFORMATION: Synthetic polynucleotide -- luxBamHI --
      Staphylococcus aureus

<400> SEQUENCE: 24
atgcggatcc tgcagatgaa gcaagaggag                              30

<210> SEQ ID NO 25
<211> LENGTH: 30
<212> TYPE: DNA
<213> ORGANISM: Artificial Sequence
<220> FEATURE:
<223> OTHER INFORMATION: Synthetic polynucleotide -- luxSalI --
      Staphylococcus aureus

<400> SEQUENCE: 25
atgcgtcgac gcagcggtat ttttcgatca                              30

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide -- luxArvseq --
      Staphylococcus aureus

<400> SEQUENCE: 26
aaggcgcgac tgttattcat                                         20
```

TREATMENT OF STAPHYLOCOCCAL DISORDERS

CROSS REFERENCE TO RELATED APPLICATIONS

This application claims the benefit of Provisional U.S. Patent Application No. 61/784,476, filed on Mar. 14, 2013, incorporated herein by reference in its entirety.

STATEMENT OF GOVERNMENT SUPPORT

This invention was made with government support under R01AR059688 awarded by the National Institutes of Health. The government has certain rights in the invention.

INCORPORATION OF SEQUENCE LISTING

The sequence listing that is contained in the file named "46671A_SeqListing.txt", which is 7.17 kilobytes as measured in Microsoft Windows operating system and was created on Mar. 14, 2014, is filed electronically herewith and incorporated herein by reference.

BACKGROUND

Staphylococci constitute a genus of gram-positive bacteria responsible for a number of disorders afflicting humans and other mammals, including infection (e.g. MRSA infections) and skin inflammation (e.g., atopic dermatitis). Atopic dermatitis (AD) is a chronic inflammatory skin disease that affects 15 to 30% of children and approximately 5% of adults in industrialized countries (Williams, et al., *J Allergy Clin Immunol* 118, 209-213 (2006)). Although the pathogenesis of AD is not fully understood, the disease is mediated by an abnormal immunoglobulin E (IgE) immune response in the setting of skin barrier dysfunction (Elias, et al., *J Invest Dermatol* 128, 1067-1070 (2008)). Mast cells (MCs) are key effector cells in IgE-mediated allergic disorders including AD. Stimulation with antigen and specific IgE initiates the activation of MCs by promoting the aggregation of FcεRI (Kawakami, et al., *Nat Rev Immunol* 2, 773-786 (2002)). Upon activation, MCs release their membrane-bound cytosolic granules leading to the release of multiple molecules that are important in the pathogenesis of AD and host defense (Galli, et al., *Nat Med* 18, 693-704 (2012); Galli, et al., *Nat Immunol* 12, 1035-1044 (2011)). More than 90% of AD patients are colonized with *Staphylococcus aureus* in the lesional skin whereas most healthy individuals do not harbor the pathogen (Rudikoff, et al., *Lancet* 351, 1715-1721 (1998)). Staphylococcal exotoxins (SEs), particularly SEA, SEB and TSST-1, can act as superantigens and/or antigens in models of AD (Leung, et al., *J Invest Dermatol* 100, 225-228 (1993); Neuber, et al., *Immunology* 75, 23-28 (1992)). However, the role of SEs in disease pathogenesis remains unclear and controversial (Kozman, A. et al. *Br J Dermatol* 163, 1308-1311 (2010)). Furthermore, a large percentage of AD patients are colonized with *S. aureus* that do not produce identifiable SEs (Leung, et al., *J Clin Invest* 92, 1374-1380 (1993)). Accordingly, a need continues to exist for materials and methods for treating, or ameliorating a symptom of, chronic inflammatory skin diseases such as atopic dermatitis.

SUMMARY OF THE INVENTION

The disclosure provides a method for treating or preventing Staphylococcal disorders such as dermal inflammation comprising the step of administering to an individual a therapeutically or prophylactically effective amount of a compound that inhibits *Staphylococcus* delta toxin. The disclosure also provides a method for preventing or treating a Staphylococcal infection comprising administering a prophylactically or therapeutically effective amount of a compound effective in inhibiting the activity or expression of delta toxin. In various aspects, the *Staphylococcus* delta toxin is a *S. aureus, S. epidermidis, S. saprophyticus, S. epidermidis, S. warneri, S. intermedius,* or *S. pseudointermedius* delta toxin.

In various aspects, the dermal inflammation arises from mast cell-mediated cytokine release, or from mast cell degranulation.

In various aspects, the inflammation is dermatitis. In various embodiments, the dermatitis is atopic dermatitis.

In various aspects, the compound inhibits delta toxin activity, the compound binds the delta toxin, the compound inhibits delta toxin interaction with mast cells, the compound inhibits delta toxin secretion, the compound inhibits delta toxin expression, the compound inhibits delta toxin transcription, or the compound inhibits delta toxin translation.

In various aspects, the compound is a polypeptide, the compound is an antibody, the compound is an antibody isolated from a polyclonal sera, the compound is a monoclonal antibody, the compound is a humanized antibody, the compound is a chimeric antibody, the compound is a single-chain antibody, the compound is a single chain Fv antibody, the compound is an Fab antibody, the compound is an Fab' antibody, the compound is an (Fab')$_2$ or the compound is an antigen-binding fragment of a monoclonal antibody. In various aspects, the compound is a delta toxin binding peptide.

In various aspects the delta toxin is set out in any one of SEQ ID NOs: 1, 2, 3, 4, 5, 6, 7, or 8. In various aspects, the delta toxin is 90% or more identical, 91% or more identical, 92% or more identical, 93% or more identical, 94% or more identical, 96% or more identical, 97% or more identical, 98% or more identical, 99% or more identical to any one of the δ-toxin proteins set out in SEQ ID NOs: 1, 2, 3, 4, 5, 6, 7, or 8. In various aspects, the compound specifically binds a carboxy terminal fragment of a delta toxin or the compound specifically binds an amino terminal fragment of the delta toxin.

In various aspects, the compound is a polynucleotide. In various aspects, the polynucleotide is an antisense oligonucleotide, an inhibitory RNA (RNAi), an antisense RNA, a short hairpin RNA (shRNA), a small interfering RNA (siRNA), a microRNA (miRNA), or a ribozyme.

In various aspects the method is carried out with the compound administered with a second therapeutic agent. In various aspects, the compounds and the second therapeutic agent are administered concurrently, and in the various aspects, compounds and the second therapeutic agent are administered consecutively. In various aspects, the second therapeutic agent is selected from the group consisting of a therapeutic protein, an antibiotic agent, an anti-inflammatory agent and a immunosuppressive agent.

Consistent with the foregoing, one aspect of the disclosure provides a method for treating or preventing skin inflammation comprising the step of administering to an individual a prophylactically or therapeutically effective amount of a compound that inhibits *Staphylococcus* delta toxin. In some embodiments, the *Staphylococcus* delta toxin is a *S. aureus, S. epidermidis, S. saprophyticus, S. epidermidis, S. warneri, S. intermedius* or *S. pseudintermedius* delta toxin.

In some embodiments, the skin inflammation arises from mast cell-mediated cytokine release. In some embodiments, the skin inflammation arises from mast cell degranulation. An exemplary skin inflammation amenable to the methods of the disclosure is dermatitis, such as atopic dermatitis.

Embodiments of this aspect of the disclosure are contemplated wherein the compound inhibits delta toxin activity, expression, or both activity and expression. For example, activity inhibition is achieved wherein the compound binds delta toxin, and/or inhibits delta toxin interaction with mast cells. Delta toxin expression is inhibited by inhibiting delta toxin secretion, and/or by inhibiting transcription and/or translation of RNA producing delta toxin.

In some embodiments of this aspect of the disclosure, compounds that inhibit RNA producing delta toxin (e.g., RNAIII) also inhibit expression of the regulatory RNAIII and, thus, the multiple virulence factors regulated by RNAIII.

In some embodiments of this aspect of the disclosure, the compound is a polypeptide. An exemplary polypeptide contemplated by the disclosure is an anti-delta toxin antibody or antigen binding fragment thereof. In some embodiments, the antibody or antigen binding fragment thereof is isolated from a polyclonal sera., and in some embodiments, the antibody or antigen binding fragment thereof is a monoclonal antibody, or fragment thereof. The disclosure comprehends any known form of antibody or fragment thereof, including but not limited to a humanized antibody, a chimeric antibody, a trifunctional or hybrid antibody, a single-chain antibody, a single chain Fv antibody, an Fab antibody, an Fab' antibody, an (Fab')$_2$, a diabody, or an antigen-binding fragment of a monoclonal antibody. Also contemplated as polypeptides for use in the methods of the disclosure are delta toxin binding peptides. As set out in greater detail below, the disclosure also contemplates a compound that is a polynucleotide or a small molecule.

In some embodiments, the delta toxin sequence is set out in SEQ ID NO: 1 (*S. aureus*), or in SEQ ID NO: 5 (*S. epidermidis*). The methods of the disclosure include embodiments wherein the compound specifically binds a carboxy terminal region of the delta toxin, such as wherein the carboxy terminal region consists essentially of SEQ ID NO. 3. In some embodiments, the compound specifically binds an amino terminal region of delta toxin, such as wherein the amino terminal region is set out in SEQ ID NO: 2.

In some embodiments of the methods according to the disclosure, the compound is a polynucleotide. Exemplary polynucleotides include a delta toxin antisense oligonucleotide and a a delta toxin inhibitory RNA (RNAi). Examples of delta toxin RNAi include, but are not limited to, a delta toxin antisense RNA, a delta toxin short hairpin RNA (shRNA), a delta toxin small interfering RNA (siRNA), a delta toxin microRNA (miRNA), or a ribozyme that interacts with a delta toxin transcript.

The disclosure comprehends embodiments of the methods wherein the compound is selected from the group consisting of HEXESTROL; SR 2640; OCTOCRYLENE|EUSOLEX; ROBUSTIC ACID; CARNOSIC ACID; SODIUM MECLOFENAMATE; DIENESTROL; DICHLOROEVERNIC ACID; TPCK; CPD000466278_1H-Indole-2-propanoic acid, 1-[(4-chlorophenyl)methyl]-3-[(1,1-dimethylethyl)thio]-Alpha,Alpha-dimethyl-5-(1-methylethyl)-[CAS]; CPD000466395_RITONAVIR; AMINOETHOXYDIPHENYLBORANE; PYRETHRINS|DRIONE; Galangine; METHYL DEOXYCHOLATE; DANTRON; DIACERIN; PHENAZOPYRIDINE HYDROCHLORIDE; SMILAGENIN; 361549, GSK-3b Inhibitor VIII; PHENOLPHTHALEIN; Sulindac Sulfide; 2',4-DIHYDROXYCHALCONE; Lonidamine; CPD000469176_TIAGABINE HCl; CLOPIDOGREL SULFATE; FLUNIXIN MEGLUMINE|BANAMINE; TESTOSTERONE PROPIONATE; CPD000449318_Benzeneacetic acid, 2-[(2,6-dichlorophenyl)amino]-, monosodium salt [CAS]; ZOMEPIRAC SODIUM; APIGENIN DIMETHYL ETHER; NIFURSOL; HAEMATOXYLIN; URSOCHOLANIC ACID; GIBBERELLIC ACID; LUMIRACOXIB|PREXIGE; CPD000466283_Altanserin; MOXIDECTIN|CYDECTIN; 4Br-AHX; LUFENURON|PROGRAM; 3-DESHYDROXYSAPPANOL TRIMETHYL ETHER; XAV939; CPD000466374_ORMETOPRIM; PANTOPRAZOLE|PROTONIX; NORETHINDRONE; DIHYDROERGOTAMINE MESYLATE; ERGOCALCIFEROL; DIBENZOTHIOPHENE; NCI16221; CPD000466305_REPAGLINIDE; CPD000058555_LY 171883; 5-CHLOROINDOLE-2-CARBOXYLIC ACID; CHLORANIL; DANAZOL; CHRYSOPHANOL; MEGESTROL ACETATE; and SP 600125. In some embodiments, the compound is selected from the group consisting of HEXESTROL; SR 2640; OCTOCRYLENE|EUSOLEX; ROBUSTIC ACID; CARNOSIC ACID; SODIUM MECLOFENAMATE; DIENESTROL; DICHLOROEVERNIC ACID; and TPCK.

Other embodiments according to this aspect of the disclosure include any of the above-described methods wherein the compound is administered with a second therapeutic agent. In some embodiments, the compound and the second therapeutic agent are administered concurrently, or consecutively. The second therapeutic may be any of a variety of compounds, including but not limited to, a therapeutic protein, an antibiotic agent, an anti-inflammatory agent and an immunosuppressive agent.

Another aspect according to the disclosure is a method of preventing or treating a Staphylococcal infection comprising administering a prophylactically or therapeutically effective amount of a compound that inhibits *Staphylococcus* delta toxin activity or expression. In some embodiments, the *Staphylococcus* delta toxin to be inhibited is a *S. aureus, S. epidermidis, S. saprophyticus, S. epidermidis, S. warneri, S. intermedius*, or *S. pseudintermedius* delta toxin. In some embodiments, the *Staphylococcus* delta toxin is derived from a methicillin-resistant *S. aureus*.

In various embodiments of the method of preventing or treating infection, the compound inhibits delta toxin activity or expression. In some embodiments, the compound is an anti-delta toxin antibody or antigen binding fragment thereof. Embodiments are contemplated wherein the antibody or antigen binding fragment thereof is a humanized antibody, a chimeric antibody, a trifunctional or hybrid antibody, a single-chain antibody, a single chain Fv antibody, an Fab antibody, an Fab' antibody, an (Fab')$_2$, a diabody, or an antigen-binding fragment of a monoclonal antibody. In some embodiments, the antibody or antigen binding fragment thereof binds a carboxy-terminal region or an N-terminal region of delta toxin, such as wherein the antibody or antigen-binding fragment thereof binds a carboxy terminal region of delta toxin that consists essentially of SEQ ID NO:3 or binds an N-terminal region of delta toxin that consists essentially of SEQ ID NO:2. In some embodiments, the compound is a polynucleotide, such as a delta toxin antisense oligonucleotide, a delta toxin inhibitory RNA (RNAi), a delta toxin short hairpin RNA (shRNA), a delta toxin small interfering RNA (siRNA), a delta toxin microRNA (miRNA), or a ribozyme that interacts with a delta toxin transcript.

The disclosure contemplates methods of preventing or treating a Staphylococcal infection wherein the compound is selected from the group consisting of HEXESTROL; SR 2640; OCTOCRYLENE|EUSOLEX; ROBUSTIC ACID; CARNOSIC ACID; SODIUM MECLOFENAMATE; DIENESTROL; DICHLOROEVERNIC ACID; TPCK; CPD000466278_1H-Indole-2-propanoic acid, 1-[(4-chlorophenyl)methyl]-3-[(1,1-dimethylethyl)thio]-Alpha,Alpha-dimethyl-5-(1-methylethyl)-[CAS]; CPD000466395_RITONAVIR; AMINOETHOXYDIPHENYLBORANE; PYRETHRINS|DRIONE; Galangine; METHYL DEOXYCHOLATE; DANTRON; DIACERIN; PHENAZOPYRIDINE HYDROCHLORIDE; SMILAGENIN; 361549, GSK-3b Inhibitor VIII; PHENOLPHTHALEIN; Sulindac Sulfide; 2',4-DIHYDROXYCHALCONE; Lonidamine; CPD000469176_TIAGABINE HCl; CLOPIDOGREL SULFATE; FLUNIXIN MEGLUMINE-|BANAMINE; TESTOSTERONE PROPIONATE; CPD000449318_Benzeneacetic acid, 2-[(2,6-dichlorophenyl)amino]-, monosodium salt [CAS]; ZOMEPIRAC SODIUM; APIGENIN DIMETHYL ETHER; NIFURSOL; HAEMATOXYLIN; URSOCHOLANIC ACID; GIBBERELLIC ACID; LUMIRACOXIB|PREXIGE; CPD000466283_Altanserin; MOXIDECTIN|CYDECTIN; 4Br-AHX; LUFENURON|PROGRAM; 3-DESHYDROXYSAPPANOL TRIMETHYL ETHER; XAV939; CPD000466374_ORMETOPRIM; PANTOPRAZOLE|PROTONIX; NORETHINDRONE; DIHYDROERGOTAMINE MESYLATE; ERGOCALCIFEROL; DIBENZOTHIOPHENE; NCI16221; CPD000466305_REPAGLINIDE; CPD000058555_LY 171883; 5-CHLOROINDOLE-2-CARBOXYLIC ACID; CHLORANIL; DANAZOL; CHRYSOPHANOL; MEGESTROL ACETATE; and SP 600125. In some embodiments, the compound is selected from the group consisting of HEXESTROL; SR 2640; OCTOCRYLENE|EUSOLEX; ROBUSTIC ACID; CARNOSIC ACID; SODIUM MECLOFENAMATE; DIENESTROL; DICHLOROEVERNIC ACID; and TPCK.

Another aspect of the disclosure is a method of vaccinating a subject at risk of developing a Staphylococcal disorder comprising administering an immunologically effective amount of an immunogen selected from the group consisting of an inactivated Staphylococcal delta toxin, an N-terminal fragment of Staphylococcal delta toxin and a C-terminal fragment of Staphylococcal delta toxin. All or part of the Staphylococcal delta toxin sequence can be modified or enlarged by adding antigenic amino acids by chemical synthesis or techniques known in the art, including the application of heat or the use of mutagenesis, such as site-directed mutagenesis. The N-terminal and C-terminal fragments of Staphylococcal delta toxin have a majority of amino acid residues corresponding to the N-terminal or C-terminal half of full-length Staphylococcal delta toxin. In some embodiments, N-terminal or C-terminal delta toxin fragments have at least 60%, 70%, 75%, 80%, 90%, or 95% of the amino acid residues corresponding to the N-terminal or C-terminal half of full-length Staphylococcal delta toxin, respectively. N-terminal and C-terminal fragments of Staphylococcal delta toxin have reduced or non-existent toxicity relative to wild-type full-length Staphylococcal delta toxin.

A related aspect of the disclosure provides a method of vaccinating a subject at risk of developing a Staphylococcal disorder comprising administering a prophylactically effective amount of an antibody or fragment thereof that specifically binds to an N-terminal fragment of delta toxin as set forth in SEQ ID NO:2 or specifically binds to a C-terminal fragment of delta toxin as set forth in SEQ ID NO:3. In various embodiments, the antibody or fragment thereof is ultimately isolated from the species to be treated or is modified to resemble antibodies (fragments) of that species. For example, vaccinating human subjects by passive immunization may be performed by administering human antibodies or fragments thereof, or by administering humanized antibodies or fragments thereof.

Another aspect of the disclosure, related to the methods disclosed herein, are uses of the compounds disclosed herein to prevent or treat Staphylococcal disorders. More particularly, the disclosure comprehends a use of the compound (any compound) disclosed herein in preventing or treating skin inflammation. The disclosure also contemplates use of the compound (any compound) disclosed herein in preventing or treating a Staphylococcal infection. The disclosure also provides a use of the compound (any compound) disclosed herein in vaccinating a subject at risk of developing a Staphylococcal disorder. For each of the methods disclosed herein, the disclosure contemplates a use of the therapeutic or prophylactic recited in that method in preventing or treating a Staphylococcal disorder such as infection or inflammation, e.g., skin inflammation, or a use of such a therapeutic or prophylactic in the preparation of a medicament for such prevention or treatment of a Staphylococcal disorder such as infection or inflammation (e.g., skin inflammation).

Other features and advantages of the disclosure will become apparent from the following detailed description, including the drawing. It should be understood, however, that the detailed description and the specific examples, while indicating embodiments, are provided for illustration only, because various changes and modifications within the spirit and scope of the disclosure will become apparent to those skilled in the art from the detailed description.

BRIEF DESCRIPTION OF THE DRAWING

FIG. 13. a—*S. aureus* isolates from the lesional skin of AD patients were assayed for δ-toxin expression, and all supernatants from 26 *S. aureus* strains isolated from the lesional skin of AD patients produced δ-toxin; b, c—RNAIII expression was detected in lesional skin colonized with *S. aureus*, but not normal skin, of AD patients.

Figure 15:
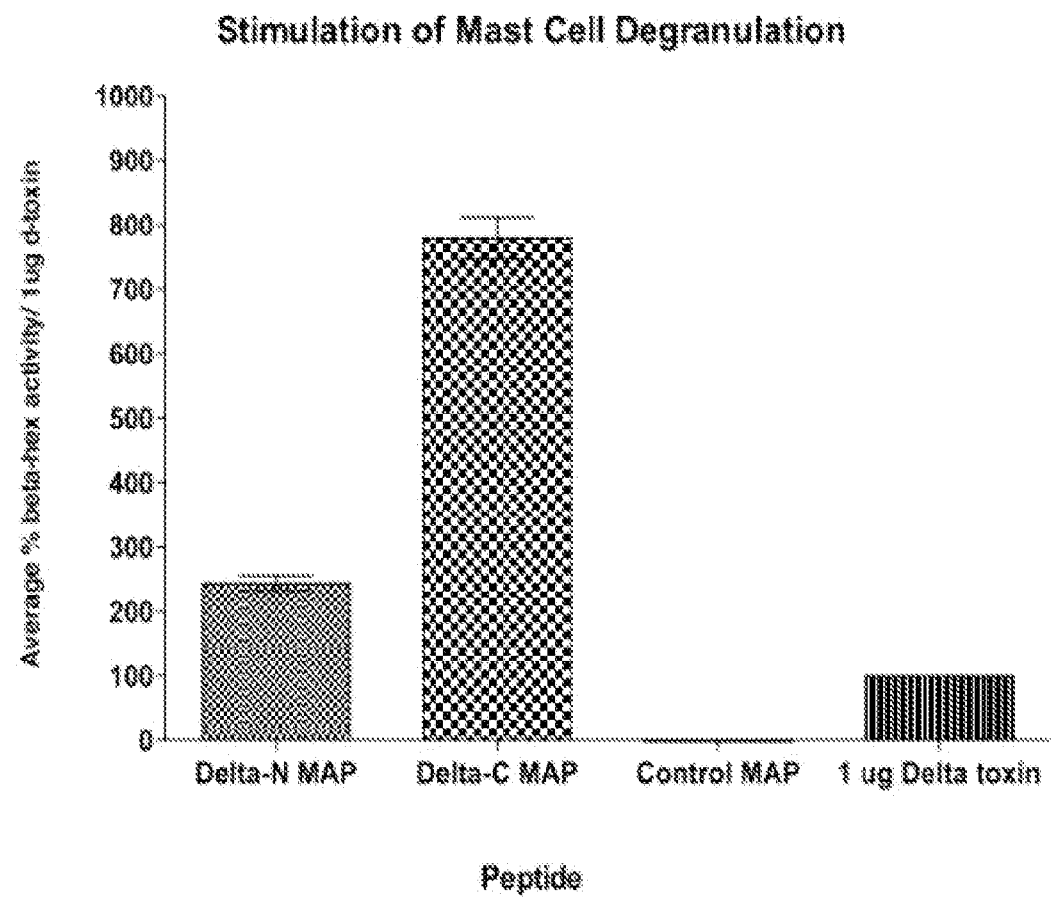

FIG. 15. Complementation of the Δhld mutant with a plasmid producing δ-toxin restored the disease score to levels comparable to the wild-type bacterium.

DETAILED DESCRIPTION OF THE INVENTION

Figure 1A:
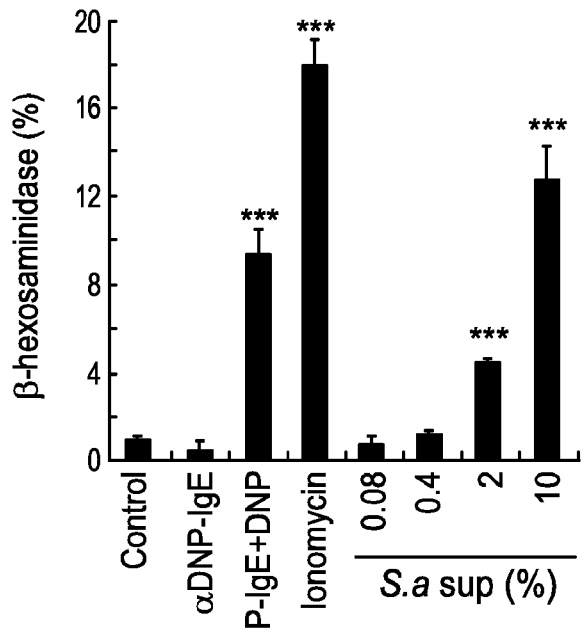
FIG. 1. δ-toxin from *S. aureus* induces MC degranulation in vitro and in vivo. a, MC degranulation activity of supernatants of BMCMCs stimulated with medium alone (Control) or indicated stimuli including different concentrations of culture supernatant of *S. aureus* 8325-4 (S.a sup). b, MC degranulation activity of supernatants of MC/9 cells stimulated with 10% of culture supernatant from LAC *S. aureus* wild-type (LAC wt) or isogenic mutants deficient in PSMα peptides (LAC Δpsmα), PSMβ peptides (LAC Δpsmβ), δ-toxin (LAC Δhld), LAC wild-type expressing vector alone (LAC pTX$_A$16), LAC deficient in δ-toxin expressing vector alone (LACΔhld pTX$_A$16) and strain complemented with δ-toxin plasmid (LACΔhld pTX$_A$hld). Control represents 10% TSB medium. c, Histamine concentrations in culture supernatant of fetal skin-derived MCs (FSMCs) after stimulation with indicated stimuli including synthetic δ-toxin at 30 μg ml$^{-1}$ for 15 min. Data represent means±s.d. of triplicate cultures. Results are representative of at least 3 independent experiments (a-c). P value refers to comparisons between experimental and control groups (a-c). d, Representative electromicroscopic images of FSMCs stimulated with synthetic δ-toxin (30 μg ml$^{-1}$) for 15 min. Images of unstimulated (Cont) and ionomycin-treated FSMCs are also shown. e, δ-toxin expression in *Staphylococcus* culture supernatants (0.5 µl per well). Loading of lanes with synthetic δ-toxin (10 ng, 100 ng) is shown as reference. f, C57BL6 (WT) and MC-deficient (Kit$^{w-sh/w-sh}$) mice were injected intradermally into the left and right ears with δ-toxin (100 µg) or PBS, respectively. One representative mouse for each group is shown. g, Quantification of Evans blue extracted from skin tissue of WT, Kit$^{w-sh/w-sh}$, Kit$^{w-sh/w-sh}$ reconstituted with BMCMCs is shown. Dots represent individual ear samples from 2 independent experiments. NS; no significant; *P<0.05; P<0.01; *P<0.001, 2-tailed t test.

The present disclosure demonstrates that culture supernatants of Staphylococcus contain potent mast cell (MC) degranulation activity. Accordingly, the disclosure provides materials and method for treating and/or preventing skin (or dermal) inflammation comprising the step of administering to an individual in need thereof a compound that neutralizes Staphylococcal δ toxin in an amount effective to neutralize δ toxin.

As described herein, biochemical purification and mass spectrometry analysis identified δ-toxin as the MC degranulation-inducing factor produced by S. aureus. MC degranulation induced by δ-toxin depended on phosphoinositide 3-kinase (PI3K) and calcium (Ca 2+) influx, but unlike that mediated by IgE crosslinking, it did not require the spleen tyrosine kinase (Syk). In addition, δ-toxin promoted antigen-independent IgE-induced MC degranulation. S. aureus isolates recovered from lesional skin of AD patients produce high amounts of δ-toxin. Importantly, skin colonization with S. aureus, but not a mutant deficient in δ-toxin, promoted IgE and IL-4 production, as well as inflammatory skin disease. Furthermore, enhancement of IgE production and dermatitis by δ-toxin was abrogated in $Kit^{W-sh/W-sh}$ $MC$-deficient mice, indicating that δ-toxin promotes skin disease through MCs. These studies identify δ-toxin as a potent inducer of MC degranulation and provide a mechanistic link between S. aureus colonization and allergic skin disease. The results disclosed herein are consistent with the host sensing S. aureus through the detection of δ-toxin, leading to the promotion of innate and adaptive Th2 immune responses via MC degranulation. The results presented herein using mouse models indicate genetically that δ-toxin promotes allergic immune responses and that strategies to inhibit δ-toxin are expected to be beneficial for the treatment of AD.

As used herein, the terms "treating", and "treatment" and the like generally mean obtaining a desired pharmacological or physiological effect. The effect may be prophylactic in terms of "preventing" or "partially preventing" a disease, symptom or condition thereof and/or may be therapeutic in terms of a partial or complete cure of a disease, condition, symptom or adverse effect attributed to the disorder. The term "treatment" as used herein covers any treatment of a disorder in a mammal, particularly a human, and includes: (a) preventing the disorder from occurring in a subject which may be predisposed to the disorder but has not yet been diagnosed as having it; (b) inhibiting the disorder, i.e., arresting its development; or (c) relieving the disorder, i.e., causing regression of the disorder and/or its symptoms or conditions.

As used herein, the terms "peptide," "polypeptide" and "protein" each refers to a molecule comprising two or more amino acid residues joined to each other by peptide bonds. These terms encompass, e.g., native and artificial proteins, protein fragments and polypeptide analogs (such as mutants, variants, and fusion proteins) of a protein sequence as well as post-translationally, or otherwise covalently or non-covalently, modified proteins. A peptide, polypeptide, or protein may be monomeric or polymeric.

A compound of the disclosure specifically binds to δ-toxin expressed by a *Staphylococcus* species. In various aspects the δ-toxin is expressed by *S. aureus*. *S. aureus* δ-toxin is also known in the art as δ-hemolysin and is a protein of 26 amino acids that contains 14 hydrophobic residues and a high percentage of nonionizable side chain amino acids. Full-length *S. aureus* δ-toxin is set out in SEQ ID NO: 1.

```
                                       (SEQ ID NO: 1)
MAQDIISTIGDLVKWIIDTVNKFTKK
```

In various aspects, compounds of the disclosure specifically bind to fragments of the full length *S. aureus* δ-toxin, such as, amino terminal (N terminal) or carboxy terminal (C-terminal) fragments. Examples, without limitation, of N terminal and C terminal peptide fragments are set out in SEQ ID NO: 2 and 3 respectively.

```
    N terminal peptide [Delta N]
                                       (SEQ ID NO: 2)
    MAQDIISTIGDLVKWIIDT C terminal peptide [Delta C]
                                       (SEQ ID NO; 3)
    IGDLVKWIIDTVNKFTKK
```

Binding to other *S. aureus* δ-toxin peptide fragments is also contemplated, including internal peptide fragments. As an example, but without limitation, an exemplary internal *S. aureus* δ-toxin fragment is set out in SEQ ID NO: 4.

```
       Internal peptide
                                       (SEQ ID NO: 4)
       IGDLVKWIIDT
```

In various embodiments, a compound of the disclosure specifically binds to *S. epidermidis* δ-toxin as set out in SEQ ID NO; 5.

```
                                       (SEQ ID NO: 5)
       MAADIISTIGDLVKWIIDTVNKFKK
```

In various embodiments, a compound of the disclosure specifically binds *S. epidermidis* δ-toxin (SEQ ID NO: 6), *S. warneri* (SEQ ID NO: 7), or *S. intermedius* (SEQ ID NO: 8).

```
                                       (SEQ ID NO: 6)
       MAADIISTIGDLVKWIIDTVNKFKK (SEQ ID NO: 7)
       MTADIISTIGDFVKWILDTVKKFTK (SEQ ID NO: 8)
       MAADIISTIVEFVKLIAETVAKFIK
```

Those of skill in the art will appreciate that the above described full length sequences represent processed form of the proteins. Accordingly, the disclosure contemplate compounds that will bind to and inhibit activity of unprocessed forms of each of these full length proteins.

Those of ordinary skill will also appreciate that other δ-toxin proteins are known in the art, and it is contemplated that compounds of the disclosure will bind and inhibit these protein as well. In particular, it is well understood that different strains of the same species of bacteria can express the same δ-toxin protein albeit with one or more amino acid variations. Thus, in still other aspects, compounds of the disclosure bind a peptide that is 85% or more identical, 86% or more identical, 87% or more identical, 88% or more identical, 89% or more identical, 90% or more identical, 91% or more identical, 92% or more identical, 93% or more identical, 94% or more identical, 96% or more identical, 97% or more identical, 98% or more identical, 99% or more identical to any one of the δ-toxin proteins set out in SEQ ID NOs: 1, 2, 3, 4, 5, 6, 7, or 8.

Compounds of the Disclosure

Compounds for use in methods of the disclosure are selected for the ability to specifically inhibit activity of δ-toxin. Compounds therefore neutralize the ability of δ-toxin to stimulate mast cell de-granulation. Compounds provided neutralize δ-toxin by specifically binding δ-toxin, specifically binding to mast cell receptors through which δ-toxin acts on mast cells, inhibit transcription of δ-toxin, inhibit translation of δ-toxin or inhibit cell surface expression of δ-toxin. Compounds neutralize δ-toxin either directly or indirectly. Examples of compounds of the disclosure include, but are not limited to, antibodies, binding peptides, and inhibitory polynucleotides.

Antibodies

An "antibody" refers to an intact immunoglobulin or to an antigen binding portion thereof that competes with the intact antibody for specific binding, unless otherwise specified. Antigen binding portions are, in various embodiments, produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, variable region fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

An "immunoglobulin" is a multimeric molecule. In a naturally occurring immunoglobulin, each multimer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5$^{th}$ Ed., US Dept. of Health and Human Services, PHS, NIH, NIH Publication no. 91-3242, 1991. Other numbering systems for the amino acids in immunoglobulin chains include IMGT® (the international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

An antibody "specifically binds" to an antigen if it binds to the antigen with a dissociation constant of 1 nanomolar or less. In various embodiments, the antibody is a monoclonal antibody. In various embodiments, the antibody is part of a mixture of antibodies in polyclonal antisera. In various embodiments, the antibody is selected from polyclonal antisera. Selection of an antibody from polyclonal antisera is routinely practiced in the art through, for example, immobilization of the antigen and selectively washing the antibody from the antigen.

Binding Peptides

Binding peptides are compounds that, like antibodies, specifically bind to a δ-toxin antigen. A binding peptide "specifically binds" to an antigen if it binds to the target with a dissociation constant of 1 nanomolar or less.

Binding peptides are available from a number of sources or can be generated, as described below.

Libraries of peptides are commercially available from, for example and without limitation, PolyPeptide Laboratories SAS (Strasbourg, France) and JPT Peptide Technologies GmbH (Berlin, Germany)). Binding peptides are also amenable to chemical synthesis. Selected peptides are subjected to peptide optimization using a microarray-based analysis to identify peptides retaining δ-toxin affinity. Peptides include those comprising all naturally occurring amino acids, all non-naturally occurring (non-conventional) amino acids or mixtures of naturally occurring and non-naturally occurring amino acids.

Non-naturally occurring amino acids include 2-aminobutyric acid (Abu); 2-Amino-isobutyric acid (Aib); β-Alanine (Bal); β-Homoglutamatic acid (Bhe); β-Homophenylalanine (Bhf); β-Homolysine (Bhk); β-Homoleucine (BM); β-Homoasparagine (Bhn); β-Homoglutamine (Bhq); β-Homoarginine (Bhr); β-Homoserine (Bhs); β-Homotyrosine (Bhy); β-Homoaspartic acid (Bhd); β-Homovaline (Bhv, Btl); β-Homoasparagin (Bhn, Btq); (S)-Cyclohexylalanine (Cha); (S)-Citrullin (Cit); (S)-2,4-Diaminobutyric acid (Dab); (S)-Diaminopropionic acid (Dap); (S)-2-Propargylglycine (Eag); (S)-N(omega)-nitro-arginine (Eew); L-homophenylalanine (Hfe); (S)-Homo-arginine (Har); (S)-Homo-citrulline (Hci); (S)-Homo-cysteine (Hcy); (S)-2-Amino-5-methyl-hexanoic acid (Hle); (S)-Homo-lysine (Hly); (S)-Norleucine (Nle); (S)-N-Methylalanine (Nma); (S)-N-Methyl-Aspartic acid (Nmd); (S)-N-Methyl-glutamic acid (Nme); (S)-N-Methyl-phenylalanine (Nmf); N-Methyl-glycine (Nmg); (S)-N-Methyl-lysine (Nmk); (S)-N-Methyl-leucine (Nml); (S)-N-Methyl-arginine (Nmr); (S)-N-Methyl-serine (Nms); (S)-N-Methyl-valine (Nmv); (S)-N-Methyl-tyrosine (Nmy); (S)-2-Amino-pentanoic acid (Nva); (S)-2-Pyridyl-alanine (Opa); (S)-Ornithine (Orn); L-phenylglycin (Phg); 4-Phenyl-butyric acid (PhPrCO); Polyethylene glycol (PEG); Selenomethionine (Sem); 1,2,3,4-L-tetrahydroisoquinolinecarboxylic acid (Tic); (13-Amino-4,7,10-trioxa-tridecayl)-succinamic acid (Ttds) and Carboxyfluorescein (FAM).

Inhibitory Oligonucleotides

Inhibitory oligonucleotides neutralize δ-toxin generally by inhibiting expression of the peptide in the host. Given that the amino acid sequences for δ-toxins are known in the art, the worker of ordinary skill will appreciate that every possible inhibitory oligonucleotide can readily be envisioned, produced and utilized. Oligonucleotides contemplated by the present disclosure include DNA, RNA and modified forms thereof, as defined herein. An "oligonucleotide" is understood in the art to be an oligomer comprising individual nucleotide subunits. Oligonucleotides include those comprised of all naturally occurring nucleotides, those with modified nucleotides, and those with a combination of both. As is known in the art, the naturally occurring nucleobases are adenine (A), guanine (G), cytosine (C), thymine (T) and uracil (U). Non-naturally occurring nucleotides are also known in the art. See, Benner et al., U.S. Pat. No. 5,432,272 and Freier et al., *Nucleic Acids Research*, vol. 25: pp 4429-4443 (1997), EP 1 072 679, WO 97/12896, U.S.

Pat. No. 3,687,808, The Concise Encyclopedia Of Polymer Science And Engineering, pages 858-859, Kroschwitz, J. I., ed. John Wiley & Sons, 1990; Englisch et al., 1991, Angewandte Chemie, International Edition, 30: 613, and Sanghvi, Y. S., Chapter 15, Antisense Research and Applications, pages 289-302, Crooke, S. T. and Lebleu, B., ed., CRC Press, 1993.

Oligonucleotides that specifically hybridize to a δ-toxin-encoding polynucleotide are generally from about 5 nucleotides to about 78 nucleotides in length. More specifically, oligonucleotides that are about 5 to about 77 nucleotides in length, about 5 to about 76 nucleotides in length, about 5 to about 75 nucleotides in length, about 5 to about 74 nucleotides in length, about 5 to about 73 nucleotides in length about 5 to about 72 nucleotides in length, about 5 to about 71 nucleotides in length, about 5 to about 70 nucleotides in length, about 5 to about 69 nucleotides in length, about 5 to about 68 nucleotides in length, about 5 to about 67 nucleotides in length, about 5 to about 66 nucleotides in length, about 5 to about 65 nucleotides in length about 5 to about 64 nucleotides in length, about 5 to about 63 nucleotides in length, about 5 to about 62 nucleotides in length, about 5 to about 61 nucleotides in length, about 5 to about 60 nucleotides in length, about 5 to about 59 nucleotides in length, about 5 to about 58 nucleotides in length, about 5 to about 57 nucleotides in length about 5 to about 56 nucleotides in length, about 5 to about 55 nucleotides in length, about 5 to about 54 nucleotides in length, about 5 to about 53 nucleotides in length, about 5 to about 52 nucleotides in length, about 5 to about 51 nucleotides in length, about 5 to about 50 nucleotides in length, about 5 to about 49 nucleotides in length about 5 to about 48 nucleotides in length, about 5 to about 47 nucleotides in length, about 5 to about 46 nucleotides in length, about 5 to about 45 nucleotides in length, about 5 to about 44 nucleotides in length, about 5 to about 43 nucleotides in length, about 5 to about 42 nucleotides in length, about 5 to about 41 nucleotides in length about 5 to about 40 nucleotides in length, about 5 to about 39 nucleotides in length, about 5 to about 38 nucleotides in length, about 5 to about 37 nucleotides in length, about 5 to about 36 nucleotides in length, about 5 to about 35 nucleotides in length, about 5 to about 34 nucleotides in length, about 5 to about 33 nucleotides in length about 5 to about 32 nucleotides in length, about 5 to about 31 nucleotides in length, about 5 to about 29 nucleotides in length, about 5 to about 28 nucleotides in length, about 5 to about 27 nucleotides in length, about 5 to about 26 nucleotides in length, about 5 to about 25 nucleotides in length, about 5 to about 24 nucleotides in length about 5 to about 23 nucleotides in length, about 5 to about 22 nucleotides in length, about 5 to about 21 nucleotides in length, about 5 to about 20 nucleotides in length, about 5 to about 19 nucleotides in length, about 5 to about 18 nucleotides in length, about 5 to about 17 nucleotides in length, about 5 to about 16 nucleotides in length about 5 to about 15 nucleotides in length, about 5 to about 14 nucleotides in length, about 5 to about 13 nucleotides in length, about 5 to about 12 nucleotides in length, about 5 to about 11 nucleotides in length, about 5 to about 10 nucleotides in length, about 5 to about 9 nucleotides in length, about 5 to about 8 nucleotides in length about 5 to about 7 nucleotides in length, or about 5 to about 6 nucleotides in length. Accordingly, oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, or 78 nucleotides in length are contemplated.

Pharmaceutical Compositions

In another aspect, the disclosure provides a pharmaceutical composition comprising the compound as described herein and one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or a dextrin, a chelating agent such as EDTA, glutathione, a stabilizer, and an excipient. In accordance with appropriate industry standards, preservatives are also added. In various aspects, the formulation of the pharmaceutical composition includes any suitable components that are non-toxic to recipients at the dosages and concentrations employed. Accordingly, the composition is, in various aspects, formulated with appropriate excipient solutions as diluents, and/or vehicles such as cocoa butter, carbowaxes and polyethylene glycols. Additionally, the compound is formulated, in various aspects, as powders, granules, ointments, solutions, suspensions, gels, microspheres, and aerosols. Further examples of components that may be employed in pharmaceutical formulations are presented in Remington's Pharmaceutical Sciences, $16^{th}$ Ed. (1980) and $20^{th}$ Ed. (2000), Mack Publishing Company, Easton, Pa.

The pharmaceutical compositions is generally administered topically. Localized administration, e.g., at a site of inflammation, is contemplated, including transdermal delivery and sustained-release compositions. In various embodiments, the compounds are formulated for topical administration by a variety of methods. An example of such a method includes encapsulating an appropriate amount of a compound in a vector selected from the group consisting of macro-capsules, micro-capsules, nano-capsules, liposomes, chylomicrons and microsponges. Another example of such a method includes absorbing a compound on a material selected from the group consisting of powdered organic polymers, talcs, bentonites, and other mineral supports. Another example includes mixing the compound with other ingredients selected from a group comprising extracted lipids, vegetable extracts, liposoluble active principles, hydrosoluble active principles, anhydrous gels, emulsifying polymers, tensioactive polymers, synthetic lipids, gelling polymers, tissue extracts, marine extracts, Vitamin A, Vitamin C, Vitamin D, Vitamin E, solar filters, and antioxidants. Other examples of suitable compositions are described, for example, in U.S. Patent Application Publication Number 2005/0249720. In various embodiments, the compounds are incorporated into a gelanic form, such as oil/water emulsions and water/oil emulsions, milks, lotions, gelling agents and thickening agents, tensioactive and emulsifying polymers, pomades, lotions, capillaries, shampoos, soaps, powders, sticks and pencils, sprays, and body oils. Colloidal dispersion systems are also contemplated in various aspects as a delivery vehicle to enhance the in vivo stability of the compound and/or to target the compound to a particular location. Colloidal dispersion systems include, but are not limited to, macromolecule complexes, nanocapsules, microspheres, beads and lipid-based systems including oil-in-water emulsions, micelles, mixed micelles, liposomes and lipid:peptide complexes. An example of a colloidal dispersion system is a plurality of liposomes (see, generally, Chonn et al., Current Op. Biotech. 6, 698-708 (1995)). Sustained-release dosage forms of the compounds are also contemplated.

Dosing and Administration

The precise amount of the compound administered to a subject is not critical, except that it should be a sufficient amount to effect improvement of the inflammatory condition. Dosing is dependent on a number of factors, including severity and responsiveness of the condition to be treated, and with the course of treatment lasting from several days to several months, or until improvement of a condition is effected or a diminution of a symptom is achieved. By way of example, in various embodiments compounds are administered to achieve from about 0.01 micrograms per milliliter (μg/mL) to about 10 milligrams per milliliter, from about 0.1 μg/mL to about 500 μg/mL, from about 0.1 μg/mL to about 1500 μg/mL, from about 1 μg/mL to about 2000 μg/mL, and from about 0.1 μg/mL to about 5000 μg/mL, including any range within these ranges, final concentrations at a target site. Compositions that include the peptide or analog in a concentration in one or more of these ranges are appropriate. Similarly, appropriate dosage values can be estimated based on the experimental data provided herein.

Guidance as to particular dosages and methods of delivery is provided in the literature and generally available to practitioners in the art. Those skilled in the art will employ different formulations for nucleotides than for proteins or their inhibitors. Persons of ordinary skill in the art can easily estimate repetition rates for dosing based on measured residence times and concentrations of the drug in bodily fluids or tissues. Following successful treatment, it can be desirable to have the patient undergo maintenance therapy to prevent the recurrence of the disease state, wherein a selected compound is administered in maintenance doses.

Dermal Inflammation

In various aspects, dermal inflammation targeted by methods of the disclosure arises from δ-toxin interaction with mast cells. The action of δ-toxin is direct or indirect. Interaction with mast cells generally leads to degranulation of the cells and an inflammatory response. In various aspects, the inflammatory response manifests as atopic dermatitis. Atopic dermatitis (AD, a type of eczema) is an inflammatory, relapsing, non-contagious and pruritic (itchy) skin disorder. It has been given names like "prurigo Besnier," "neurodermitis," "endogenous eczema," "flexural eczema," "infantile eczema," and "prurigo diathésique." De Benedetto, et al., The Journal of Investigative Dermatology 129 (1): 14-30 (2009); Abels, et al., Zeitschrift fur Dermatologie, Venerologie, and verwandte Gebiete 57 (8): 711-725 (2006).

In various aspects, inflammation arises from, or is perpetuated by, a defective dermal barrier. Decreased ceramides, the major water-retaining lipids of the stratum corneum, leads to increased trans-epidermal water loss (TEWL) and contributes to dry cracked skin, predisposing to bacterial colonization. Alternatively, the pH of the skin surface in certain inflammatory indications is high or alkaline, creating a suitable environment for colonization.

Combination Therapy

Methods of the disclosure include a combination therapy wherein a compound of the disclosure is administered with one or more additional therapeutic agents. Therapeutic agents include proteins that are expressed at lower than normal levels in instances of dermal inflammation, antibiotics, anti-inflammatory agents and immunosuppressive agents. Each of these types of compounds are contemplated for use with a compound of the disclosure along with combinations of these agents with a compound of the disclosure.

Therapeutic Proteins

In various embodiments, the additional therapeutic compound is a protein that is involved in maintenance of the skin barrier (filaggrin-2, corneodesmosin, desmoglein-1, desmocollin-1, and transglutaminase-3) and generation of natural moisturizing factor (arginase-1, caspase-14, and gamma-glutamyl cyclotransferase) which is expressed at lower levels in dermal inflammation. Lower expression of skin barrier proteins and enzymes involved in the generation of the natural moisturizing factor could further exacerbate barrier defects and perpetuate water loss from the skin.

Antibiotics

Methods of the disclosure contemplate combination therapy with a compound of the disclosure with one or more antibiotics. Antibiotics contemplated for combination therapy include the general classes of beta-lactams, carbapenems, penicillins, cephalosporins, macrolides, fluoroquinolones, sulfonamides, tetracyclines, aminoglycosides, quinolones, oxazolidinones, ansamycins, glycopeptides, lincosamides, lipopeptide, monobactams, nitrofurans, polypeptides, cyclic lipopeptides, glycylcyclines, and lipiarmycins. More generally, these compounds are described by their mode of action, including those that target the bacterial cell wall (penicillins and cephalosporins), or those that target the cell membrane (polymixins). Those compounds that interfere with essential bacterial enzymes (rifamycins, lipiarmycins, quinolones, and sulfonamides) are generally bactericidal, those that target protein synthesis (aminoglycosides, macrolides, and tetracyclines) are usually bacteriostatic.

Specific antibiotic compounds contemplated include penicillin, amoxicillin, cephalexin, clarithromycin, erythromycin, clarithromycin, azithromycin, ciprofloxacin, levofloxacin, ofloxacin, co-trimoxazole, trimethoprim, tetracycline, doxycycline, gentamicin ampicillin, rifampin, norfloxacin, furazolidone, silver sulfadiazine, tigecycline, dapsone, cefoperazone, prontosil, gemifloxacin, hydrocortisone/acetic acid, enoxacin, sulfisoxazole, sulfadimidine, sulfapyridine, sulfamerazine, grepafloxacin, sulfalene, sulfamethoxypyridazine, sulfaphenazole, sulfabenzamide, sulfamoxole, sulfametrole, sulfametoxydiazine, sulfaperin, sulfathiourea, sulfametomidine, daptomycin, tigecycline, linezolid, fidaxomicin, dicloxacillin, oxacillin, metronidazole, mupirocin, or fusidic acid.

Anti-Inflammatories

Combination therapy according to the disclosure also contemplates use of a compound of the disclosure in combination with one or more anti-inflammatory agents, including steroids, non-steroidal anti-inflammatory drugs (NSAIDS) and immune selective anti-inflammatory derivatives (ImSAIDs). Specific anti-inflammatory compounds include hydrocortisone, methylprednisolone, nimesulide, naproxen, rilonacept, diclofenac+misoprostol, sulfasalazine, betamethasone, valdecoxib, aspirin, diclofenac, mesalamine, sulindac, balsalazide, cortisone, oxaprozin, prednisone, dexamethasone, olsalazine, magnesium salicylate, diflunisal, budesonide, diclofenac epolamine, balsalazide disodium, canakinumab, mesalamine, etodolac, loteprednol, nimesulide, fenoprofen, diclofenac sodium, meclofenamate, mefenamic acid, lumiracoxib, triamcinolone acetonide, acetonide, rimexolone, diclofenac potassium, aspirin, ibuprofen, naproxen, corticosteroids, and acetaminophen.

Immunosuppressives

Combination therapy also contemplates use of a compound of the disclosure with one or more immunosuppressive agents. Immunosuppressive agents include, for example and without limitation, azathioprine, 6-mercaptopurine, methotrexate, tacrolimus, cyclosporine, antistaphylococcal, macrolide antibiotics (and clarithromycin), and penicillinase-resistant penicillin.

The following examples are given merely to illustrate aspects of the disclosure and not in any way to limit its scope.

Example 1

Materials and methods utilized in experiments described herein include the following.

Bacterial Strains

S. aureus strain 8325-4 and its isogenic toxin mutant (Δαβγ) have been previously described in Nilsson, et al., Infect Immun 67, 1045-1049 (1999). S. aureus strains SA113 and Newman, and isogenic mutants deficient in lipoprotein diacylglyceryl transferase (Δlgt) have also been previously described in Stoll, et al., Infect Immun 73, 2411-2423 (2005). S. aureus strains LAC and MW2, their isogenic δ-toxin mutants (Δhld), the psm gene deleted mutants (Δpsmα, Δpsmβ), and LAC agr mutant (Δagr) have been described in Wang et al., Nat Med 13, 1510-1514 (2007). The Agr quorum-sensing system of S. aureus controls the expression of virulence factors in response to autoinducing peptides (AIPs). The isogenic Δhld mutant of S. epidermidis 1457, a clinical isolate[20] was produced by an allelic replacement procedure[21]. This was done in a way analogous to the S. aureus Δhld mutants used herein, abolishing translation by exchanging the third base in the hld start codon from ATG to ATA (to avoid interfering with the function of RNAIII). LAC P3-lux was constructed by integration of the S. aureus LAC agr P3 promoter fused to the luxABCDE genes with codon usage optimized for staphylococci[22] into the Φ11 attB site of the S. aureus genome, using a procedure described by Luong and Lee[23]. Plasmid pTX$_A$hld was constructed by cloning the hld coding sequence containing the ribosomal binding site region in the BamH1/Mlu1 sites of plasmid pTX$_A$[10]. The hld gene was amplified from the genomic DNA of the respective strain, because the δ-toxin sequence differs in one amino acid in position 10 (serine or glycine) in these two strains. The δ-toxin is constitutively expressed in these plasmids. See Table 1 for all oligonucleotides used in generation of the strains. Clinical isolates of S. aureus from children diagnosed with AD were obtained originally from the Department of Laboratory Medicine and Pathobiology at University of Toronto, as described in Yeung, et al., Microbes Infect 13, 189-197 (2011). S. epidermidis (NI335), S. cohnii (NI446), S. saprophyticus (NI488), S. xylosus (NI987), S. sciuri (NI981), S. succinus (NI534), S. lentus (NI487) and S. fleuretti (NI533) were isolated by plating on BHI after culturing at 37° C. for two days under aerobic conditions. Identification of bacterial species was verified by 16S rRNA gene sequencing as described in Hasegawa, et al., J Biol Chem 281, 29054-29063 (2006). Bacterial supernatants were produced by overnight culture with shaking in tryptic soy broth (TSB) followed by filtration through a 0.2 µm filter.

TABLE 1

| Name | Sequence (5'-3'); Sequence Identifier |
|---|---|
| Construction of pTXΔhld | |
| Delta Barn | CTAGATCACAGAGATGTGATGGATCCTAGTTGATGAGTTG; SEQ ID NO: 16 |
| Delta Mlu | GTTGGGATGGCTTAATAACGCGTACTTTTAGTACTATACG; SEQ ID NO: 17 |
| Construction of S. epidermidis hld mutant | |
| HLDATT1 | GGGGACAAGTTTGTACAAAAAAGCAGGCTTGGTACTTCTGGTTC GTCAAAGTAAGAGGCACA; SEQ ID NO: 18 |
| HLDATT2 | GGGGACCACTTTGTACAAGAAAGCTGGGTGGCACTTCTGGTTCG TCAAAGTAAGAAGCACA; SEQ ID NO: 19 |
| HLD1 | CGAAAGGAGTGAAGTTATAATAGCAGCAGATATC; SEQ ID NO: 20 |
| HLD2 | GATATCTGCTGCTATTATAACTTCACTCCTTTCG; SEQ ID NO: 21 |
| Integration of P3-lux in the S. aureus genome | |
| P3prEco | CAATTTTACACCACTCTCCTCACTGGAATTCCATTATACG; SEQ ID NO: 22 |
| P3prBam | ATGCGGATCCCTCATCAACTATTTTCCATCACATCTCTGT; SEQ ID NO: 23 |
| luxBamHI | ATGCGGATCCTGCAGATGAAGCAAGAGGAG; SEQ ID NO: 24 |
| luxSalI | ATGCGTCGACGCAGCGGTATTTTTCGATCA; SEQ ID NO: 25 |
| luxArvseq | AAGGCGCGACTGTTATTCAT; SEQ ID NO: 26 |

Mice

C57BL/6, C57BL/6-Kit W-sh/Kit W-sh (B6.CG-Kit W-sh/HNihrJaeBsmJ), and BALB/c mice were purchased from Jackson Laboratories (Bar Harbor, Me.). Syk+/− mice of breeding age can be obtained by one of ordinary skill in the art using conventional breeding techniques and/or recombinant technology. For the experiments described herein, Syk+/− mouse breeders were a gift of Dr. Steven Teitelbaum (Washington University School of Medicine, St. Louis, Mo.) and Syk −/− embryos were generated by intercrossing. All mouse strains were housed under pathogen-free conditions. The animal studies were conducted under approved protocols by the University of Michigan Committee on Use and Care of Animals.

Synthetic Peptides

The synthetic peptides fPSMcc2 (fMGIIAGIIK-VIKSLIEQFTGK; SEQ ID NO: 9), fPSMcc3 (fMGI-IAGIIKFIKGLIEKFTGK; SEQ ID NO: 10), fδ-toxin (fMAQDIISTIGDLVKWIIDTVNKFTKK; SEQ ID NO: 11), (WRWWWW-CONH2; SEQ ID NO: 12) and MMK-1

(LESIFRSLLFRVM; SEQ ID NO: 13) were purchased from American Peptide. Unformylated δ-toxin (MAQDIIS-TIGDLVKWIIDTVNKFTKK; SEQ ID NO: 1) was synthesized at The University of Michigan Protein Structure Facility. Polyclonal anti-δ-toxin antibody was produced in rabbits by immunization with a synthetic multiple antigenic peptide displaying an 18-amino-acid peptide (IGDLVKWI-IDTVNKFTKK; SEQ ID NO: 3) (Sigma-Genosys) from the full-length δ-toxin sequence. Rabbit IgG was purified from rabbit serum on Protein A (Pierce) according to the manufacturer's protocol.

Skin Disease Score

The severity of skin lesions was scored according to defined macroscopic diagnostic criteria in a blind fashion[29]. In brief, the total clinical score of skin lesions was designated as the sum of individual scores, graded as 0 (none), 1 (mild), 2 (moderate), and 3 (severe) for thickness, erythema, edema, erosion, and scaling.

Immunoglobulin Levels

Serum IgG1 and IgG2a were measured with an ELISA kit (Cayman chemical). Serum IgE was also measured with an ELISA kit (Bethyl Laboratories). An ELISA for OVA-IgE was described in Nakajima et al., *J. Allergy Clin. Immunol.* 129, 1048-1055 (2012).

RNA Isolation from Human Skin Samples

Wash fluid derived from lesional and normal skin of AD patients was collected using a 2.5-cm-diameter polypropylene chamber as described in Travers et al., J. Allergy Clin. Immunol. 125, 146-152e141-142 (2010). 100 µl of the samples were mixed with an equal volume of RNAprotect Bacteria Reagent (QIAGEN®) and RNA extracted with Bacterial RNA Kit (OMEGA®). The human studies were approved by the Indiana University Institutional Review Committee. Informed consent was obtained from all subjects.

Quantitative Real Time RT-PCR cDNA was synthesized using High Capacity RNA-to-cDNA Kit (Applied Biosystems), according to the manufacturer's instructions. Quantitative real time RT-PCR (qPCR) was performed using a SYBR green PCR master mix (Applied Biosystems) and StepOne Real-time PCR system (Applied Biosystems). Primers to amplify mouse Fpr genes (Riviere et al., Nature 459, 574-577 (2009)) and bacterial genes (RNAIII, gyrB, 16S rRNA) (Seidl et al., Antimicrob. Agents Chemother. 55, 5631-5639 (2011) and Barman et al., Infect. Immun. 76, 907-915 (2008)) have been described. Expression of mouse Fpr genes was normalized to that of Gapdh (F; 5-CCTCGTCCCGTAGACAAAATG-3 (SEQ ID NO: 14), R; 5-TCTCCACTTTGC-CACCTGCAA-3 (SEQ ID NO: 15)) and expression was analyzed by the $2^{-\Delta\Delta Ct}$ method. RNAIII expression in human skin samples was normalized to that of *S. aureus* gyrB and that of gyrB to universal bacterial 16S rRNA and relative expression calculated by the $2^{-\Delta Ct}$ method. RNAIII and gyrB expression in some human skin samples were below the detection limit and were arbitrarily given a value of zero for statistical analysis. LAC wt and LAC Δagr cultured for 24 hours were used as reference controls.

Measurement of P3-Lux Expression

For determination of the levels of P3-lux expression in culture, $10^5$ ml$^{-1}$ LAC P3-lux strain was suspended in TSB and luminescence emitted from P3-lux-expressing bacteria was measured using a LMax luminometer (Molecular Devices). For in vivo bioluminescence imaging (BLI), mice were sacrificed, the skin dressing removed and immediately placed into the light-tight chamber of the CCD camera system (IVIS200, Xenogen). Luminescence emitted from lux-expressing bacteria in the tissue was quantified using the software program living image (Xenogen).

Statistical Analysis

All analyses were performed using GraphPad Prism. Differences were considered significant when p values were less than 0.05.

Example 2

In a first series of experiments, degranulation of mast cells was measured in response to contact with various *Staphylococcus* strains. Degranulation was measured in cell culture as follows.

Preparations of BMCMCs and fetal skin-derived mast cells (FSMCs) were previously described in Yamada, et al., *J Invest Dermatol* 121, 1425-1432 (2003). The purity of MCs was confirmed by surface expression of CD45 and CD117 (eBioscience).

Degranulation of MCs was assessed by β-hexosaminidase assay as previously described in Yamada, et al., *J Invest Dermatol* 121, 1425-1432, (2003). Briefly, MCs ($2\times10^6$ ml$^{-1}$) were preloaded with or without anti-DNP IgE (0.3 µg ml$^{-1}$) in RPMI with IL-3 for 15 hours. The cells were resuspended in Tyrode's buffer (Sigma) at $2\times10^4$ cells per 100 µl for FSMCs or $1\times10^5$ cells per 100 µl for BMCMCs and MC/9 cells, aliquoted in triplicate into a 96-well U-bottom plate and incubated with EGTA (1 mM, Sigma), LY294002 (100 µM, Sigma) and WRW4 (Trp-Arg-Trp-Trp-Trp-Trp-CONH2 (SEQ ID NO: 12, 10 mM, American peptide) and Cyclosporine H (10 µM, Alexis Biochemicals) for 30 min, and then stimulated with DNP-HSA (30 ng ml$^{-1}$) TNP-HSA (30 nM) for 30 min, followed by exposure to Ionomycin (1 µM, Sigma) δ-toxin (indicated concentrations), PSMαs (indicated concentrations) or FPR2 ligands for 15 min. Results of various stimuli are given as a relative percentage, where freeze and thaw of total cell culture represents 100%.

Figure 5A:
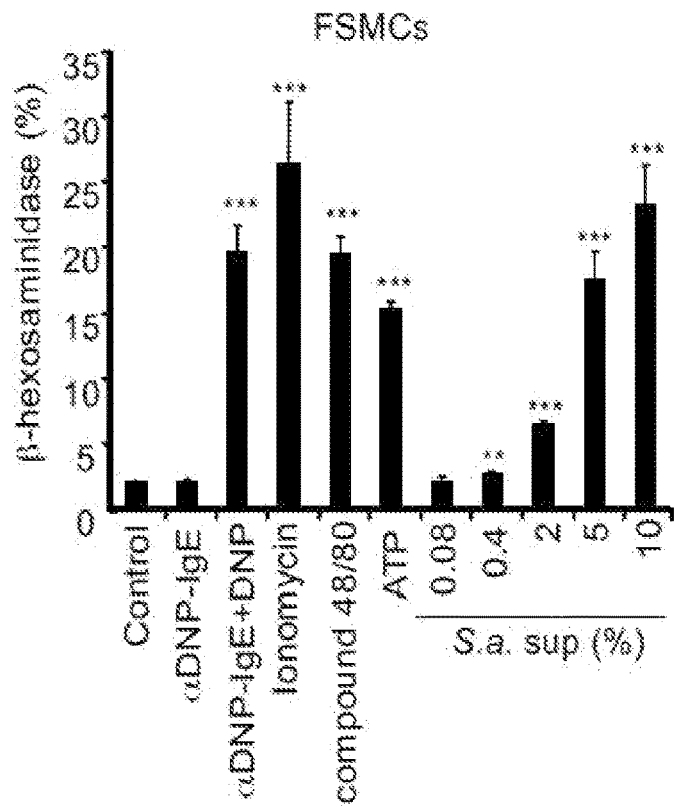
FIG. 5. Culture supernatant from *S. aureus* induces MC degranulation. (a) β-hexosaminidase activity from supernatants of fetal skin-derived MC (FSMC) cultures stimulated with medium alone (Control), αDNP-IgE alone, aDNP-IgE plus DNP, ionomycin, ATP and indicated concentrations of culture supernatant from *S. aureus* (8325-4). (b) β-hexosaminidase activity from supernatants of MC/9 cell cultures stimulated with indicated stimuli. (c) β-hexosaminidase activity from supernatants of MC/9 cells stimulated with 10% culture supernatant of indicated *Staphylococcus* species. Data represent means±s.d. of triplicate cultures. *P<0.05; ***P<0.001, two-tailed Student's t-test. (d) MC/9 cells were incubated 60 minutes in medium (Control), 10% *S. aureus* culture supernatant (8325-4) or medium containing Nigericin (10 µM, used as a positive control). Percentage of propidium iodide (PI)-positive cells were measured by flow cytometry. Data are representative of at least two independent experiments.
Figure 5B:
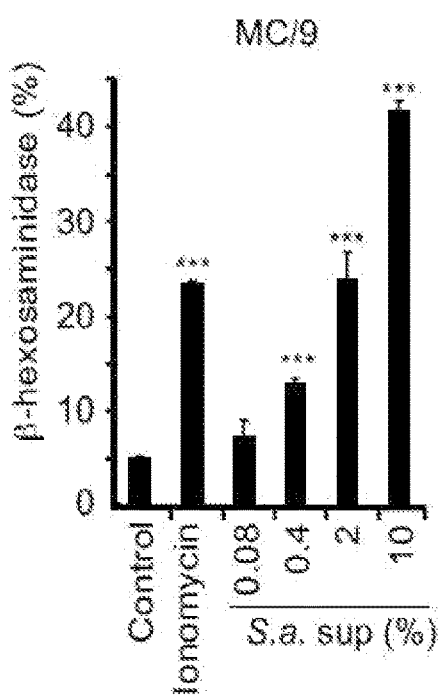
Figure 5D:
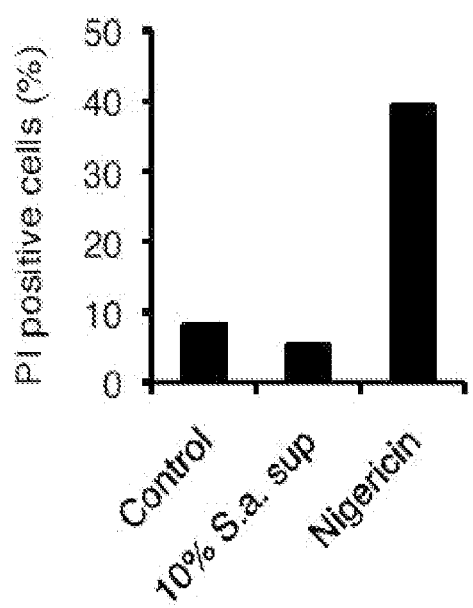

A first experiment was designed to determine whether *S. aureus* can release factors that induce MC degranulation. Results showed that the culture supernatant of *S. aureus* induced rapid and robust degranulation of MCs in a dose-dependent manner (FIG. 1*a*, FIGS. 5*a* and *b*).

Analysis of a panel of *Staphylococcus* isolates revealed that the culture supernatant of several *S. aureus* strains as well as of that from *S. epidermidis* and *S. saprophyticus*, but not of *S. xylosus*, *S. sciuri*, *S. cohnii*, *S. succinus*, *S. lentus* or *S. fleuretti*, elicited MC degranulation (FIG. 5*c*).

Figure 1B:
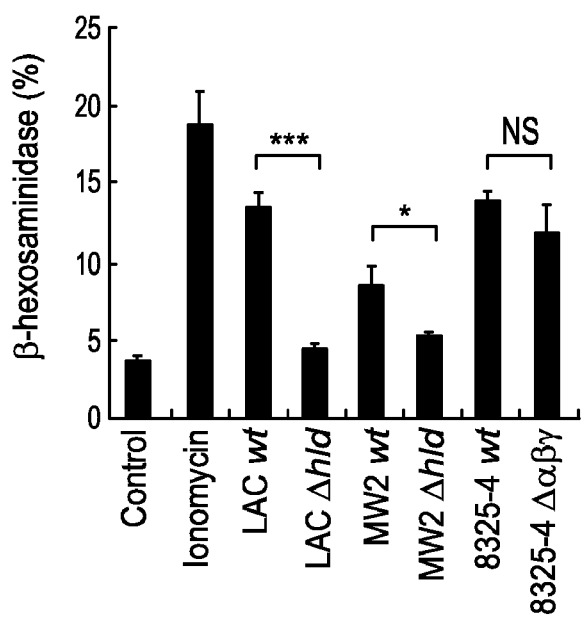
Figure 7A:
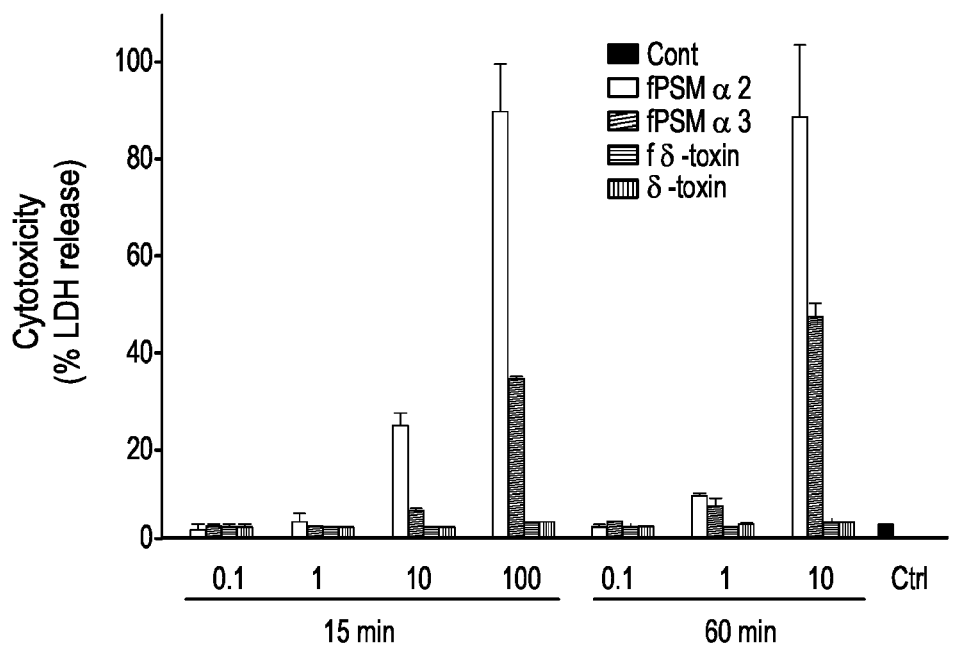
FIG. 7. MC degranulation activity of δ-toxin is independent of formylation. (a) % LDH released from MC/9 cells stimulated by medium alone (Ctrl) and indicated concentrations (µg ml-1) of PSMs for 15 or 60 minutes. (b) β-hexosaminidase assay from supernatants of MC/9 cells stimulated with indicated concentrations (µg ml-1) of formylated PSMαs. (c) β-hexosaminidase assay from supernatants of MC/9 cells stimulated with indicated concentrations (µg ml-1) of unformylated δ-toxin (δ-toxin) or formylated δ-toxin (fδ-toxin) (left panel). β-hexosaminidase assay from supernatants of MC/9 cells stimulated with indicated concentrations (µg ml-1) of unformylated δ-toxin (δ-toxin) or control peptide (right panel). (d) IL-8 secretion in cultured supernatant of human neutrophils stimulated by indicated concentrations (µg ml-1) of phenol-soluble modulins (PSMs). Data represent means±s.d. of triplicate cultures. Data are representative of three independent experiments.
Figure 7B:
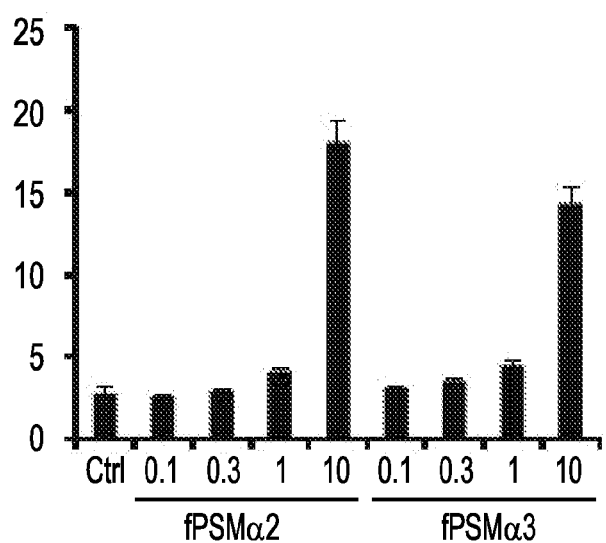
Figure 7C:
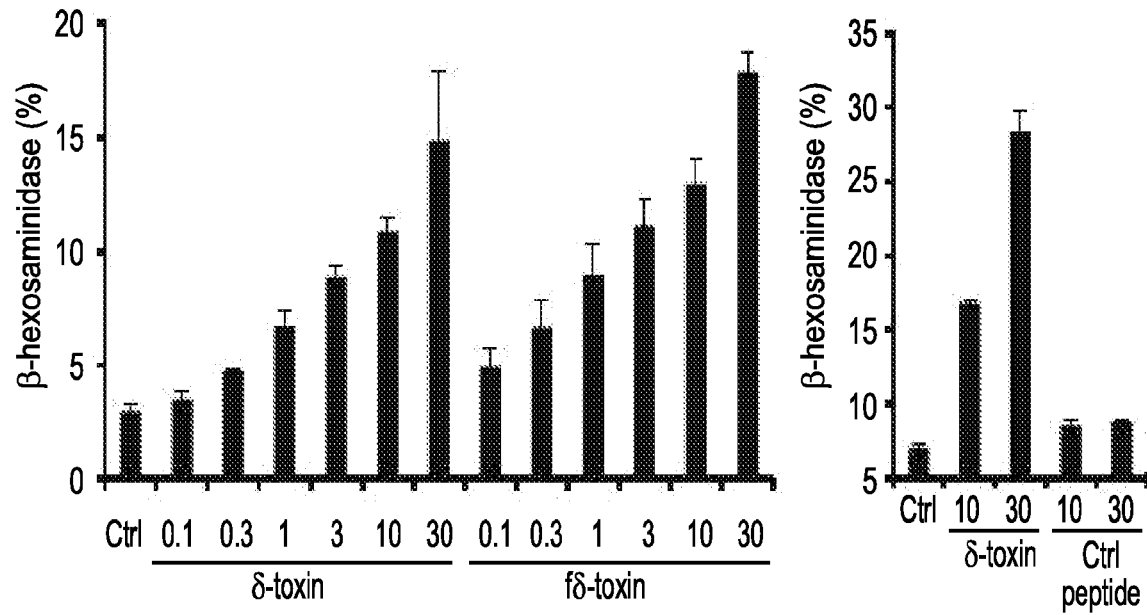

TLR2 stimulation via lipopeptides has been shown by some studies, but not others, to induce MC degranulation. See Supajatura, et al., *J Clin Invest* 109, 1351-1359 (2002); Selander, et al., *J Immunol* 182, 4208-4216 (2009). However, neither the culture supernatants of *S. aureus* deficient in lipoproteins (Δlgt), which lacks TLR2-stimulating activity (Schmaler, et al., *J Immunol* 182, 7110-7118 (2009)), nor that from bacteria deficient in α-, β-, and γ-hemolysins (Δαβγ) were impaired in MC degranulation activity (FIG. 1*b*, FIG. 5*c*, and FIG. 7*c*).

Analysis revealed that MC degranulation activity was enriched in the culture supernatant of *S. aureus* (FIG. 6*a*) and was present in the supernatant of *S. aureus* grown in defined chemical medium supplemented with 2% yeast extract (FIG. 6*a*).

Figure 6B:
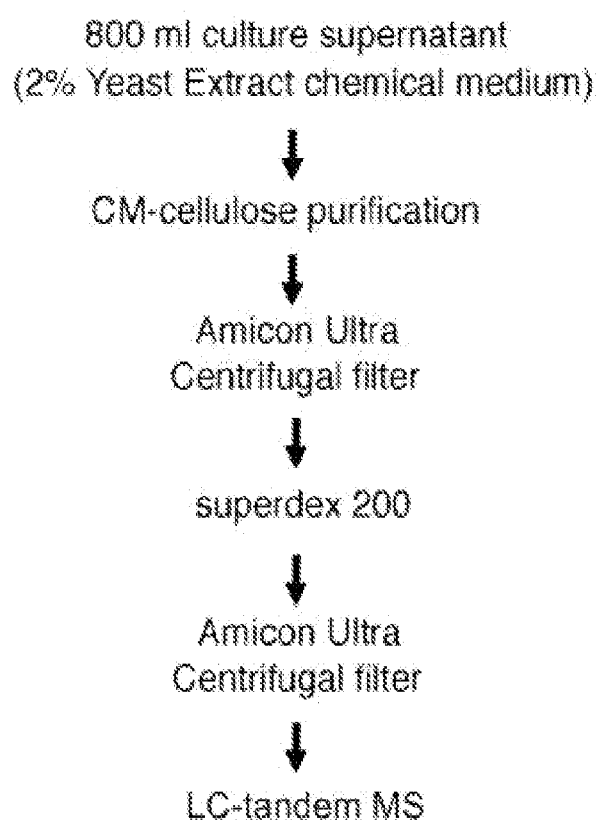
FIG. 6. Characterization, purification and mass spectrometry identification of δ-toxin. (a) β-hexosaminidase activity compared with that of BHI culture supernatant (sup) and bacterial pellet (100%). (b) Purification scheme for identification of δ-toxin. (c) Proteins identified in the purified sample. The summarized "total independent spectra" is indicative of the relative abundance of a specific protein in the purified sample. Full length of mature form δ-toxin sequence were detected (MAQDIISTIGDLVKWI-IDTVNKFTKK; SEQ ID NO: 1). (BHI; brain heart infusion, TSB; tryptic soy broth, DEAE; Diethylaminoethyl, CM; Carboxymethyl.

The MC degranulation-inducing factor was sensitive to heat, phenol/chloroform extraction and protease K treatment, indicating that it was a protein (FIG. 6*a*). Furthermore, the MC degranulation-inducing factor bound to both diethylaminoethyl and carboxymethyl cellulose matrices and was present in the void fraction on gel filtration at neutral pH (FIG. 6b).

Example 3

In view of the results above, a process to purify a factor from S. aureus culture supernatant that induced degranulation was designed (FIG. 6b).

S. aureus was cultured in 700 ml chemical defined medium supplemented with 2% yeast extract (see Miller, R. D. & Fung, D. Y. Amino acid requirements for the production of enterotoxin B by Staphylococcus aureus S-6 in a chemically defined medium, Miller et al., *Appl Microbiol* 25, 800-806 (1973).) Filtered culture supernatant was incubated with carboxymethyl cellulose equilibrated with 10 mM sodium citrate (pH 5.5), and eluted with a linear gradient of 0-1 M NaCl. Fractions containing β-hexosaminidase activity were collected and adjusted to pH 7.4, 100 mM HEPES. The sample was concentrated using Amicon Ultra-15, 5 kDa filter (Millipore). The concentrated sample was further fractionated with a Superdex 200 10/300 GL column (GE). Final positive fractions were pooled and concentrated using an Amicon Ultra-15 filter (FIG. 2c).

Liquid chromatography-mass spectrometry analysis was then utilized to more fully characterize the isolated protein. The purified sample was denatured in 8 M urea, reduced by incubation with 10 mM DTT at 37° C. for 30 mM and alkylated using 50 mM iodoacetamide at room temperature for 30 minutes. The protein sample was digested with sequencing grade trypsin (Promega) overnight at 37° C. The reaction was terminated by acidification with trifluoroacetic acid (0.1% v/v) and peptides were purified using a SepPak C18 cartridge following the manufacturer's protocol (Waters Corporation). Eluted peptides were directly introduced into an ion-trap mass spectrometer (LTQ-XL, ThermoFisher) equipped with a nano-spray source. The mass spectrometer was operated in data-dependent MS/MS mode to acquire a full MS scan (400-2000 m/z) followed by MS/MS on the top 6 ions from the full MS scan. Dynamic exclusion was set to collect 2 MS/MS spectra on each ion and exclude it for a further 2 mM. Raw files were converted to mzXML format and searched against the S. aureus NCTC 8325 database supplemented with a decoy (reverse) database using X! Tandem with k-score plug-in using an open-source search engine developed by the Global Proteome Machine. The search parameters included a precursor peptide mass tolerance window of 1 Da and fragment mass tolerance of 0.5 Da. Oxidation of methionine (+16 Da), and carbamidomethylation of cysteines (+57 Da) were considered as variable modifications. The search was restricted to tryptic peptides with one missed cleavage. Results of the X! Tandem search were then subjected to Trans-Proteomic Pipeline (TPP) analysis, a suite of software including PeptideProphet and ProteinProphet. All proteins with a ProteinProphet probability of >0.9 were considered positive and verified manually.

The purified material revealed that δ-toxin (also called δ-hemolysin or Phenol-Soluble Modulin gamma (PSMγ)), a 2.9 kDa peptide secreted by S. aureus, was the most abundant and significant protein identified in the purified sample (FIG. 6c).

To confirm this result, the ability of the S. aureus strains LAC and MW2 that express δ-toxin, and their isogenic δ-toxin-deficient strains (Δhld), to induce MC degranulation was assessed. Results showed that MC degranulation induced by S. aureus culture supernatant was completely dependent on the expression of δ-toxin (FIG. 1b and FIG. 7a).

Figure 16A:
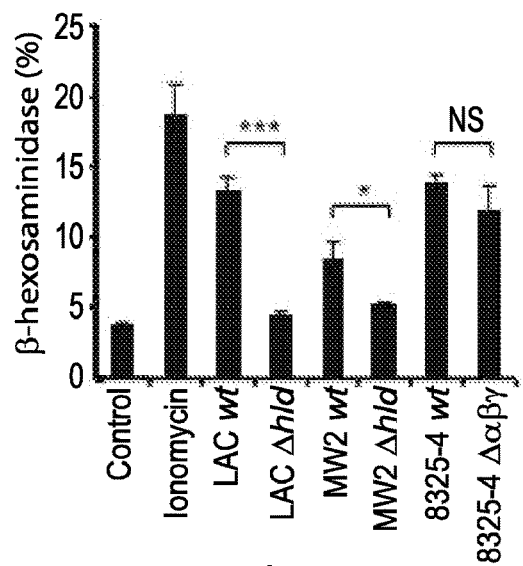
FIG. 16. Amount of δ-toxin in *S. aureus* supernatant. (a) MC degranulation activity of supernatants of MC/9 cells stimulated with 2% of culture supernatant of *S. aureus* strains. Data represent means±s.d. of triplicate cultures. NS; not significant, *P<0.05; ***P<0.001, two-tailed Student's t-test. (b) δ-toxin expressions of filtered supernatants from *S. aureus* strains (SA113, LAC and 8325-4) detected by RP-HPLC/ESI-MS. ND; not detected. Bars represent the means. (c) δ-toxin expression in supernatants from *S. aureus* wild-type (LAC (pTx Δ 16)), δ-toxin deletion (LAC Δhld (pTx Δ 16)) and complemented strain (LAC Δhld (pTx Δ hld)), detected by extracted ion chromatograms. Chromatography was performed as described previously[15]. Data are representative of three independent experiments.

Mutant analyses in two S. aureus strains revealed that MC degranulation induced by S. aureus culture supernatant required expression of δ-toxin whereas deficiency of related PSMα or PSMβ peptides had minimal or no effect on MC degranulation (FIG. 1b and FIG. 16a). Importantly, complementation of the Δhld mutant strain with δ-toxin producing plasmid, but not control plasmid, restored the ability of the culture supernatant to induce MC degranulation (FIG. 1b and FIG. 16a).

Example 4

Figure 1C:
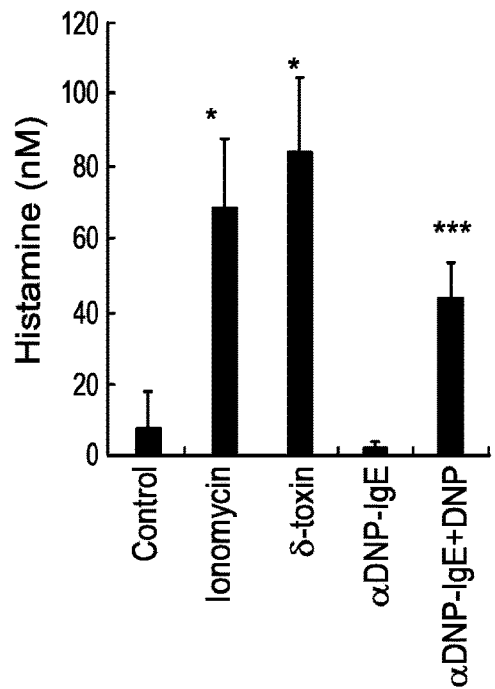

After δ-toxin stimulation, rapid release of histamine, another feature of MC degranulation, was observed (FIG. 1c). Histamine concentration was measured in a culture supernatant of fetal skin-derived MCs (FSMCs) after stimulation with synthetic δ-toxin at 30 μg ml$^{-1}$ for 15 minutes.

Figure 1D:
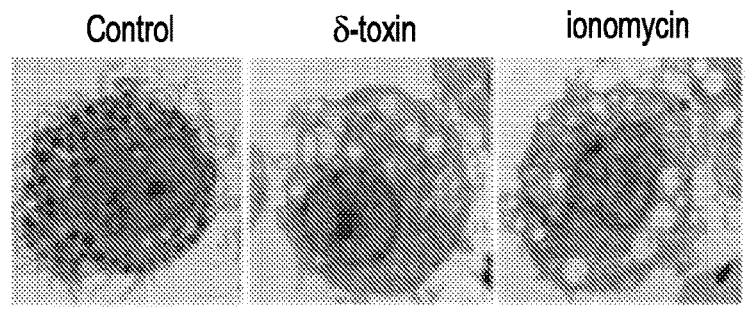

Furthermore, transmission electron microscopy revealed classical features of MC degranulation without loss of plasma membrane integrity upon δ-toxin stimulation (FIG. 1d). These results indicated that δ-toxin is the MC degranulation-inducing factor released by S. aureus.

Example 5

The gene for δ-toxin is embedded in the gene for the regulatory RNA, i.e., RNAIII (Novick, R. P. et al. Synthesis of staphylococcal virulence factors is controlled by a regulatory RNA molecule. Novik, et al., *EMBO J* 12, 3967-3975 (1993)). The RNAIII and PSM genes are regulated by AgrA (Queck, et al., *Mol Cell* 32, 150-158, (2008)). Because the function of RNAIII and expression of PSMs are not affected in the δ-toxin S. aureus mutants used in these studies (Wang, et al., *Nat Med* 13, 1510-1514 (2007)), the results indicate that δ-toxin is the major MC degranulation-inducing factor released by S. aureus.

PSMs, especially PSMα2 and PSMα3 induce cell death and IL-8 release in human neutrophils. (Wang et al., *Nat Med* 13, 1510-1514 (2007); Kretschmer, et al., *Cell Host Microbe* 7, 463-473 (2010)). Because δ-toxin is highly related to PSMα2 and PSMα3, the viability of MCs after stimulation with synthetic PSMα2, PSMα3, or δ-toxin, was assessed. In accord with results in neutrophils (Wang, R. et al. Identification of novel cytolytic peptides as key virulence determinants for community-associated MRSA. Wang et al., *Nat Med* 13, 1510-1514 (2007)), PSMα2 and PSMα3 induced robust loss of cell viability in MCs (FIG. 7a).

Chemokines and cytokines released from cells were measured with enzyme-linked immunosorbent assay (ELISA) kits (R&D Systems). For tissue cytokines, skin tissue (5×10 mm² area) was removed and homogenized. The skin homogenates were centrifuged and supernatants were collected for cytokine measurements by ELISA.

Figure 16B:
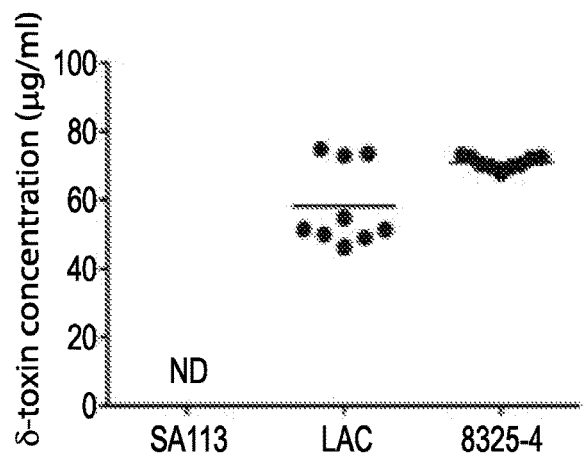
Figure 16C:
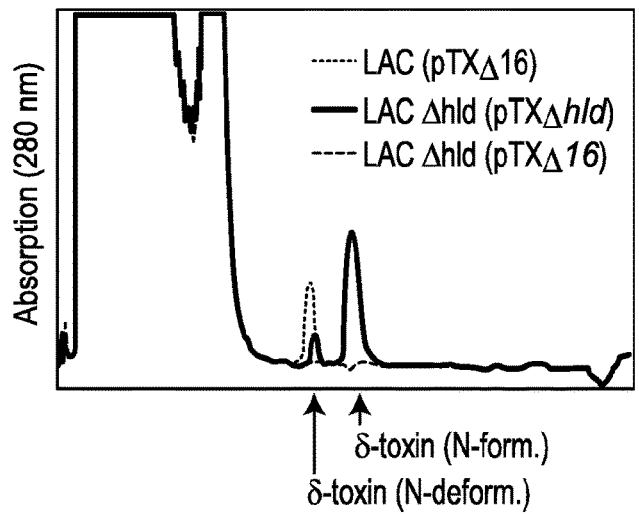

Stimulation with δ-toxin did not induce detectable cell death in MCs (FIG. 16a). Notably, formylation of the N-terminus of the δ-toxin peptide was not required for MC degranulation activity whereas it was essential for the ability of δ-toxin to induce the release of IL-8 from human neutrophils (FIGS. 16b and 16c). Non-toxic concentrations of PSMαs did not possess any MC-degranulation activity (FIG. 7b). In contrast, stimulation with a concentration of δ-toxin that induces robust MC degranulation did not induce detectable cell death in MCs (FIGS. 7a and 7c).

Figure 7D:
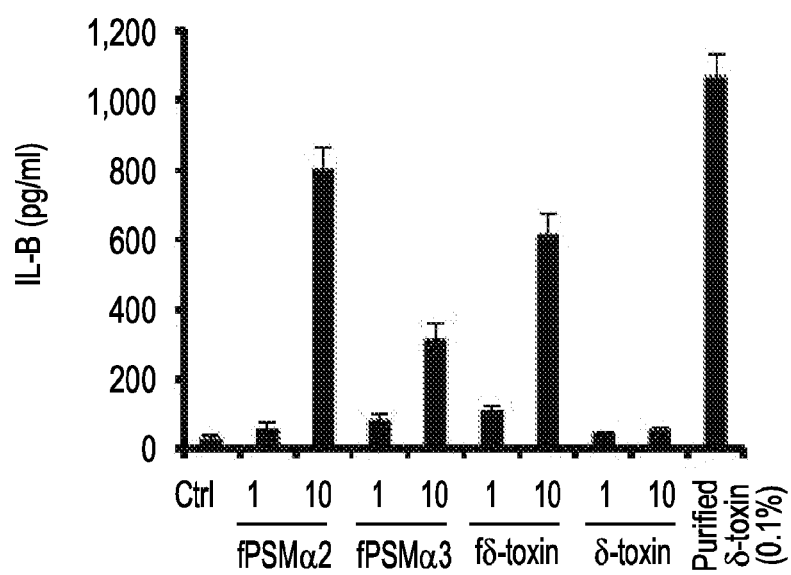
Figure 8A:
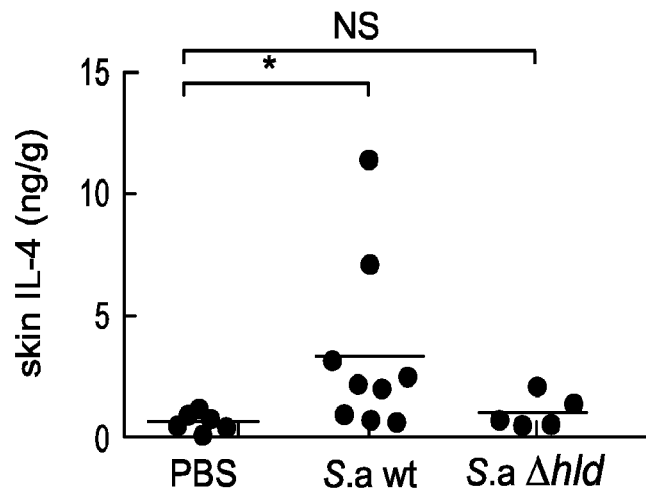
FIG. 8. a—Stimulation of primary mouse macrophages and keratinocytes with PSMα2, but not δ-toxin, triggered robust cell death; b—mice colonized with wild-type *S. aureus* developed greater amounts of serum IgE and the cytokine IL-4 than mice inoculated with the δ-toxin mutant bacterium.
Figure 8B:
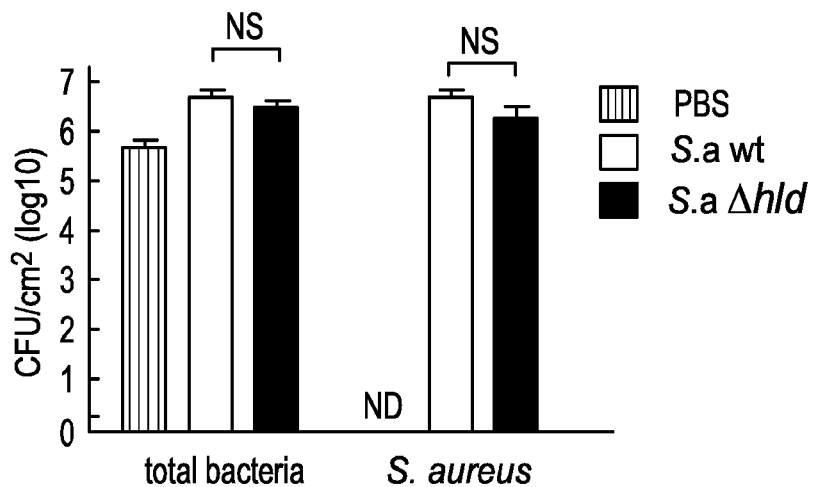
Figure 9:
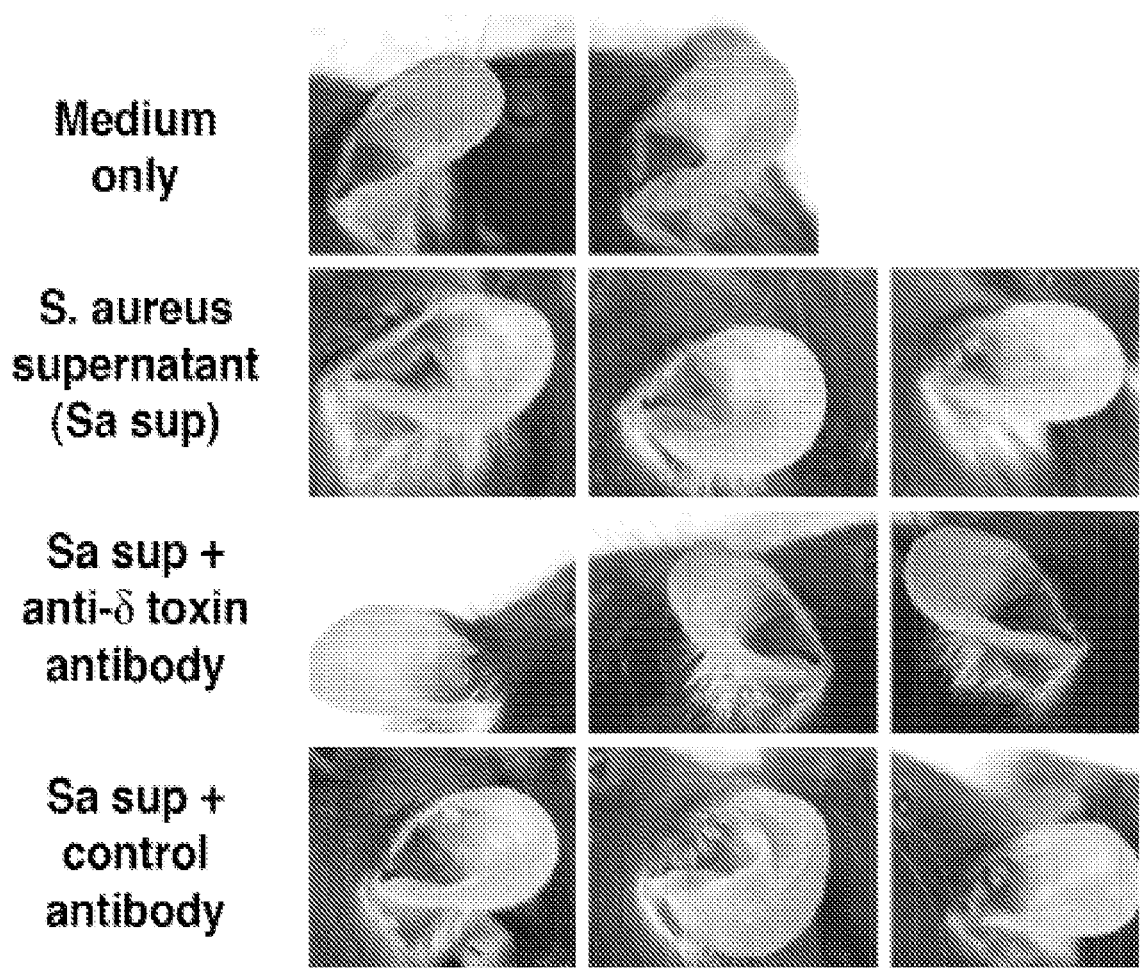
FIG. 9. Supernatant from *S. epidermidis*, a bacterium present in normal skin, possessed weak MC degranulation, which correlated with smaller amounts of δ-toxin, when compared to that from *S. aureus* strains, but the deficiency of δ-toxin had a larger effect on MC degranulation in *S. aureus* than in *S. epidermidis*.
Figure 10:
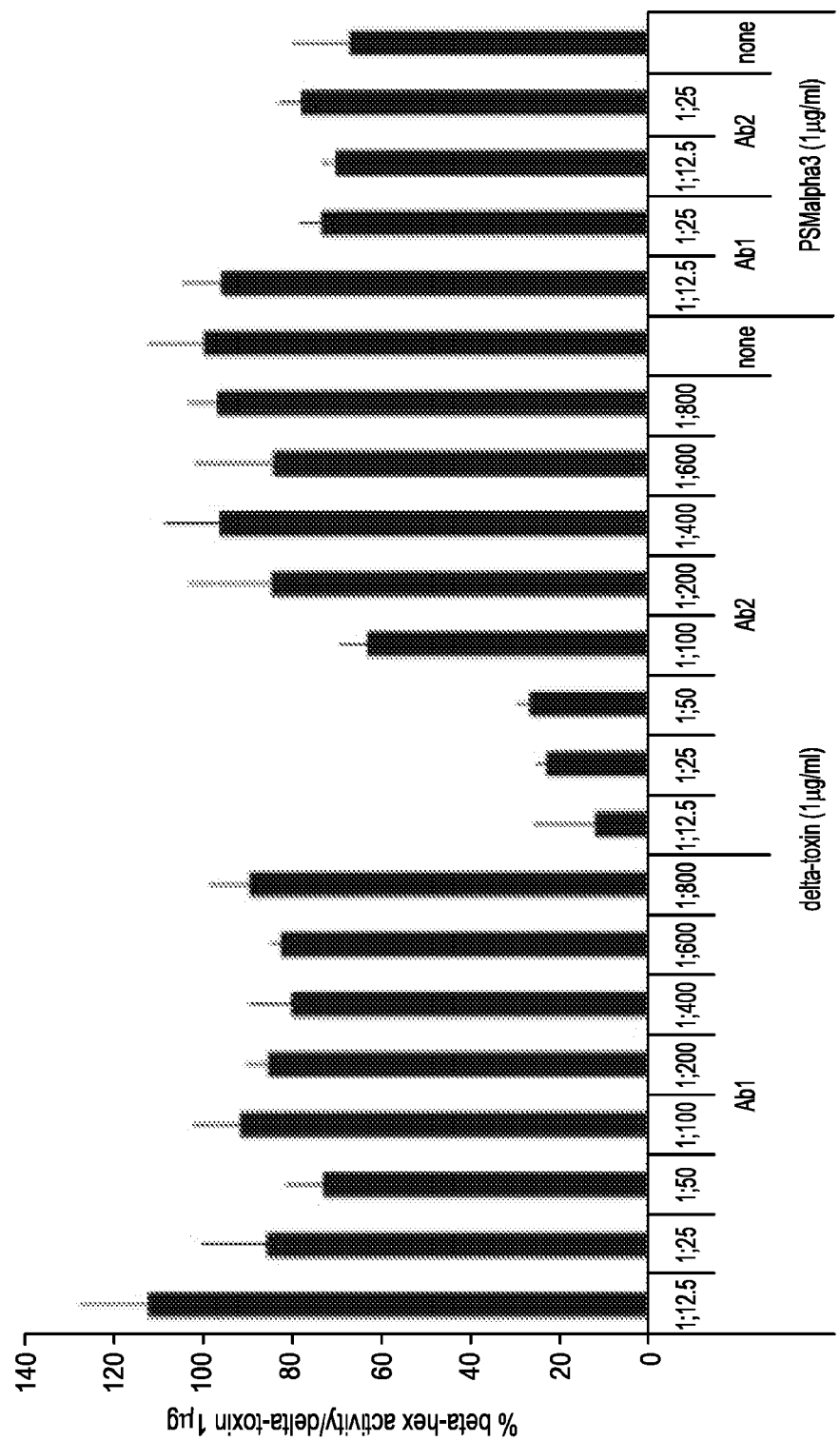
FIG. 10. the culture supernatant from the δ-toxin positive LAC strain induced leaking of Evans blue dye whereas that from δ-toxin-negative LACΔhld and SA113 strains did not.
Figures 11A, 11B:
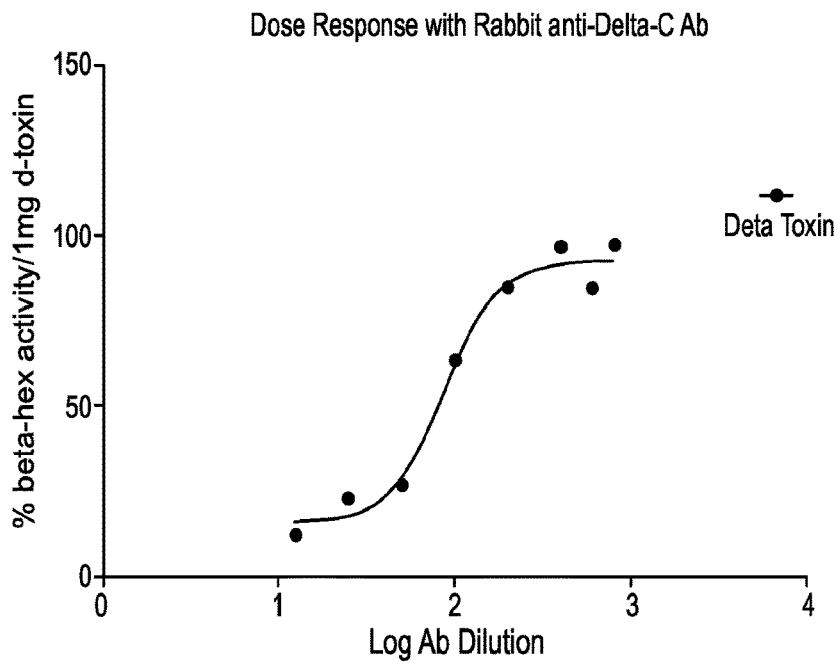
FIG. 11. a, Delta-C antibody has an EC50 of approximately 86, meaning that at a dilution of 1:86, the affinity purified antibody inhibits 50% of the hexosaminidase production, as determined by plotting using 4-parameter linear regression. b, Data characterizing the graph is presented.
Figure 17:
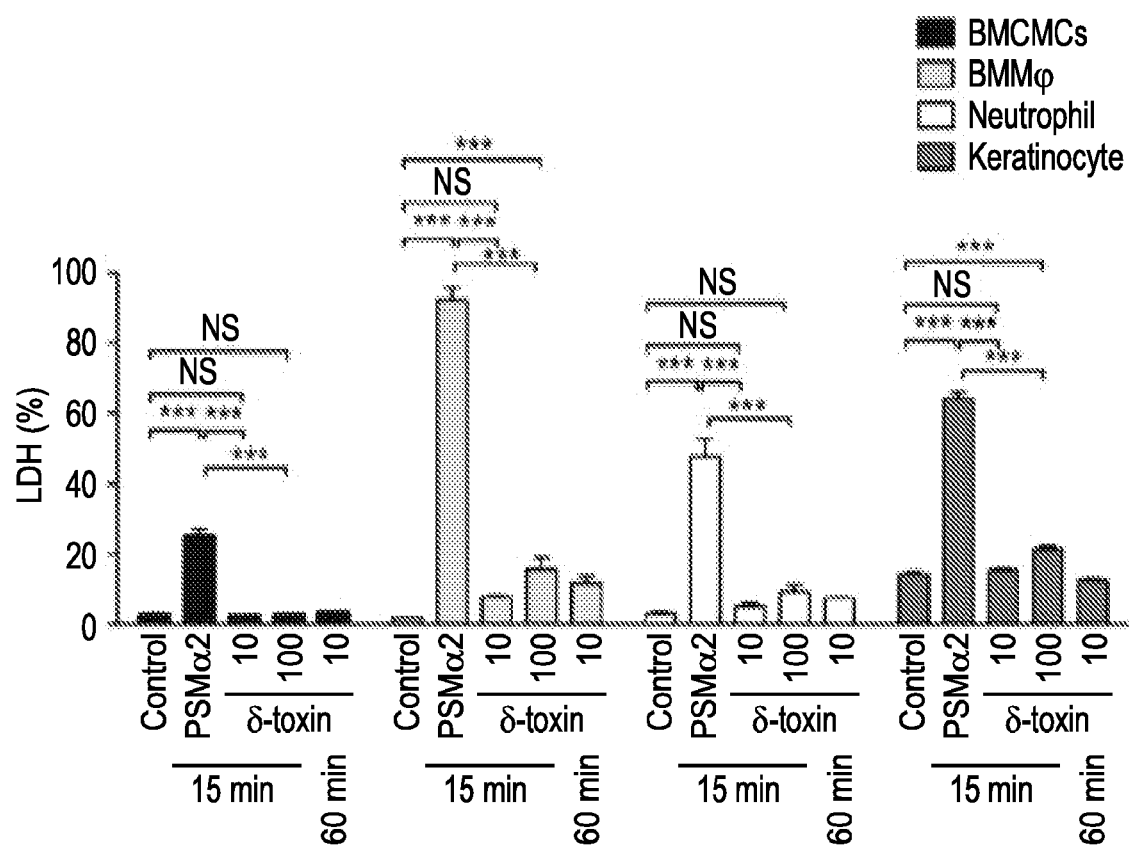
FIG. 17. Cell toxicity of δ-toxin. BMCMCs, BMMφ (bone marrow derived macrophages), bone marrow neutrophils and primary keratinocytes isolated from mice were stimulated with PSMα (10 μg ml−1) or δ-toxin (10 or 100 μg ml−1) for indicated times. Cell toxicity was measured by LDH assay. Data represent means±s.d. of triplicate cultures. NS; not significant, ***P<0.001, one-way ANOVA with Tukey's post-hoc test for multiple comparisons. Data are representative of two independent experiments.

Consistent with previous results, stimulation of human neutrophils with formylated PSMα2, PSMα3 or δ-toxin induced robust IL-8 release (FIG. 16c and FIG. 7d). Moreover, stimulation of primary mouse macrophages and keratinocytes with PSMα2, but not δ-toxin, triggered robust cell death (FIG. 17). Thus, the MC degranulation activity induced by δ-toxin is not associated with cell death and is different from other activities triggered by PSMα2 and PSMα3.

Figure 1E:
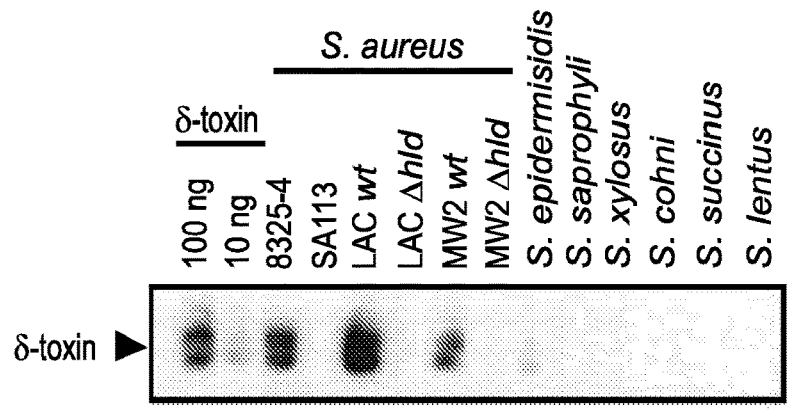
Figure 18A:
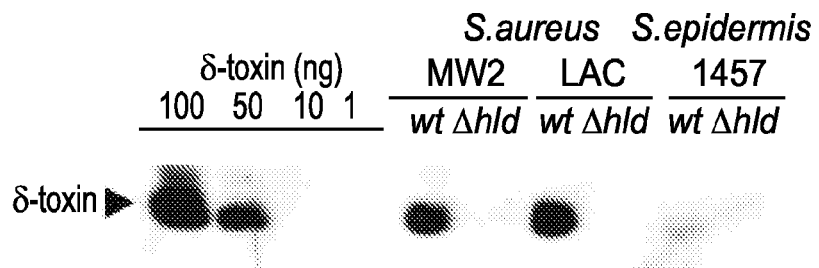
FIG. 18. MC degranulation activity of δ-toxin in supernatant from *S. aureus* and *S. epidermidis*. (a) Immunoblot analysis of culture supernatants of *S. aureus* wild-type (LAC), δ-toxin deletion (LAC Δhld), *S. epidermidis* wild-type (1457) and δ-toxin deletion (1457 Δhld)(0.25 μl per well). (b) β-hexosaminidase from MC/9 cells stimulated by medium alone (Control), culture supernatants of *S. aureus* wild-type (LAC), δ-toxin deletion (LAC Δhld), *S. epidermidis* wild-type (1457) and δ-toxin deletion (1457 Δhld). Data represent means±s.d of triplicate cultures. *P<0.05, P<0.01, *P<0.001, two-tailed Student's t-test. Data are representative of three independent experiments.
Figure 18B:
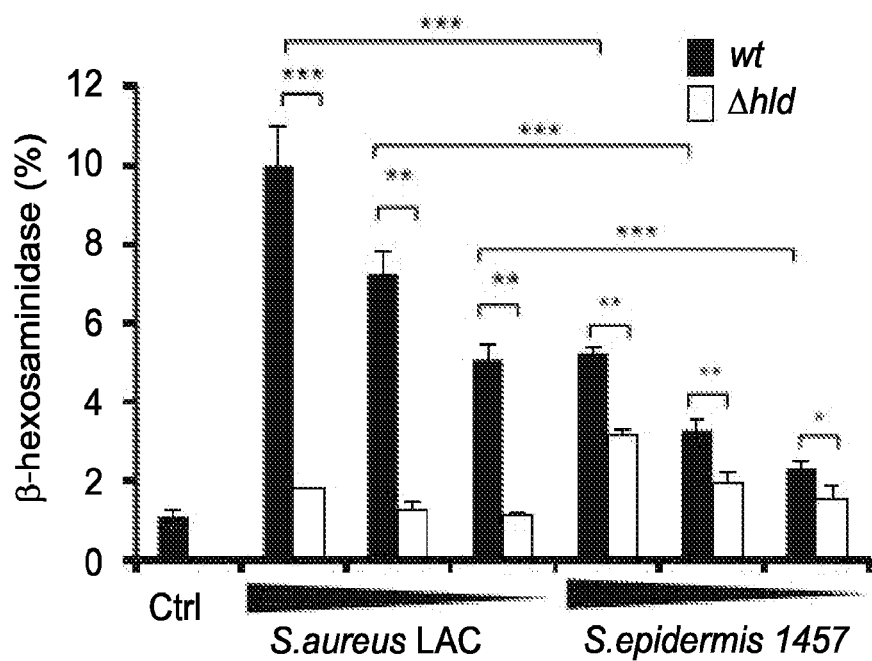

Immunoblotting antibody confirmed that the presence of δ-toxin in *S. aureus* supernatants correlated with MC degranulation activity (FIG. 1e). Notably, supernatant from *S. epidermidis*, a bacterium that is present in normal skin, possessed weak MC degranulation, which correlated with smaller amounts of δ-toxin when compared to that from *S. aureus* strains (FIG. 1e and FIG. 18). Furthermore, deficiency of δ-toxin had a larger effect on MC degranulation in *S. aureus* than in *S. epidermidis* (FIG. 18).

To assess whether δ-toxin induces MC degranulation in vivo, synthetic δ-toxin was injected into the skin of mouse ears and MC degranulation was monitored by the vascular leakage of Evan's blue dye into the extravascular space using the passive cutaneous anaphylaxis (PCA) assay.

Figure 31A:
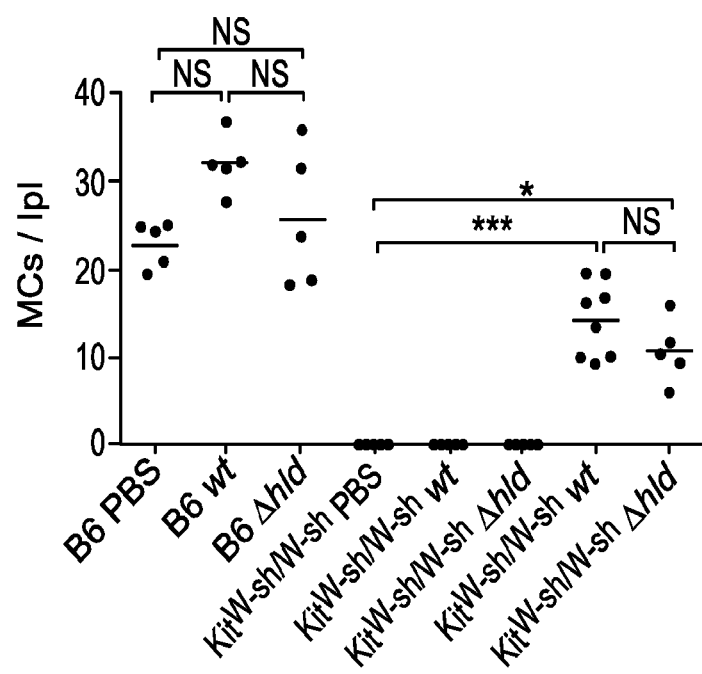
FIG. 31. Staphyloccocus δ-toxin promotes IgE production and inflammatory skin disease via mast cells. (a) The number of cutaneous MCs detected by toluidine blue staining. Five low power fields (lpf) were counted. A dot represents the average of MCs per lpf from one mouse. Bars represent the means. The results were derived from two of the pooled experiments. NS; no significant, *P<0.05, *P<0.001, Kruskal-Wallis test. (b) Representative skin histopathology of C57BL6 (B6), $Kit^{W-sh/W-sh}$ and MC-reconstituted $Kit^{W-sh/W-sh}$ mice colonized with wild-type S. aureus (S.a. wt), δ-toxin deficient S. aureus (S.a. Δhld) or treated with PBS. Skin sections were stained with H&E (HE) and toluidine blue (TB). Left 2 files, Bar=100 μm. Right 2 files shows high power images of degranulated MCs (yellow arrow heads indicate toluidine-positive granules outside MCs only found in S.a. wt inoculated skin but not in S.a. Δhld). Bar=10 μm. (c) Number of culturable bacteria and S. aureus in skin of B6 and $Kit^{W-sh/W-sh}$ mice 1 week post inoculation with S. aureus. Results are mean±s.e.m (B6; n=8, $Kit^{W-sh/W-sh}$; n=7). NS; no significant, P<0.01, ***P<0.001, two-tailed Student's t-test. Data are representative of at least two independent experiments.
Figure 31B:
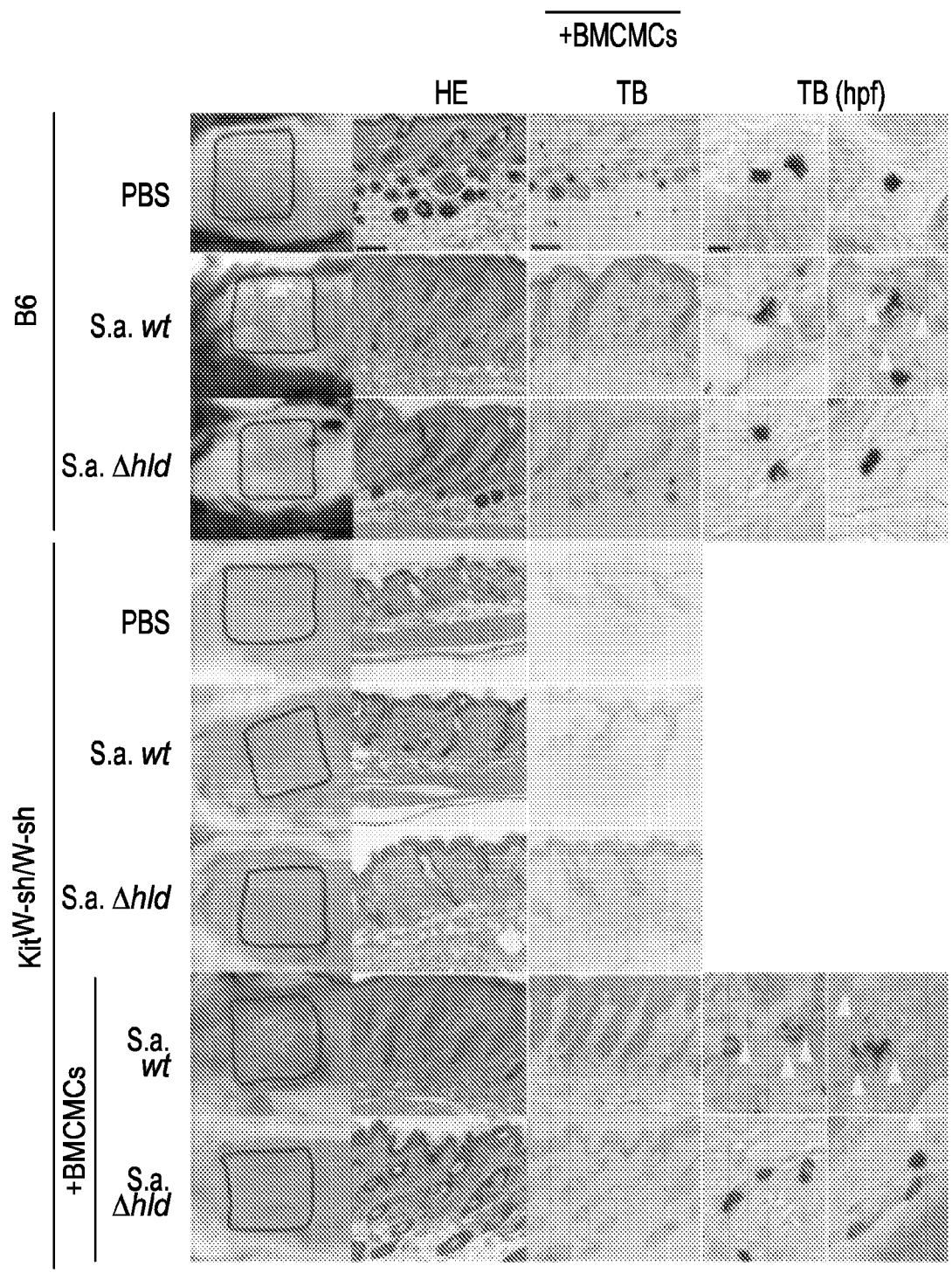
Figure 31C:
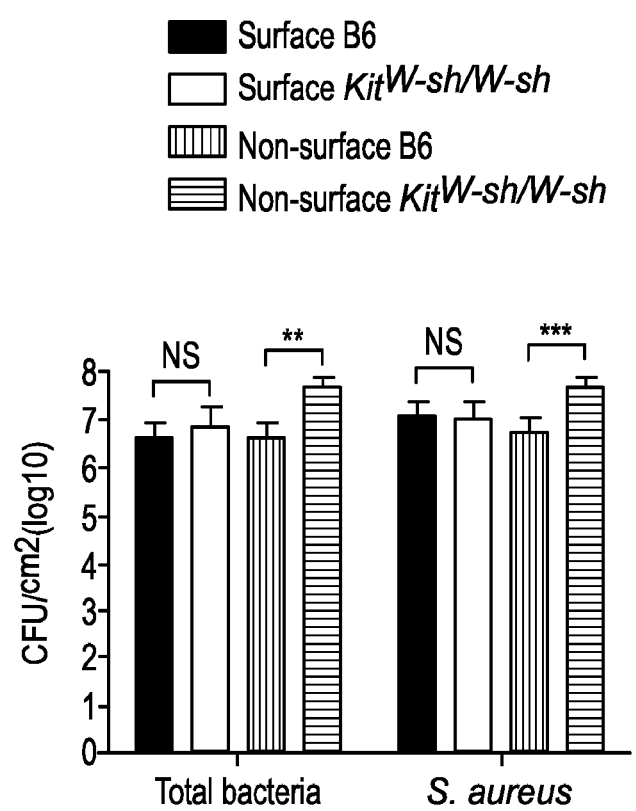
Figure 32A:
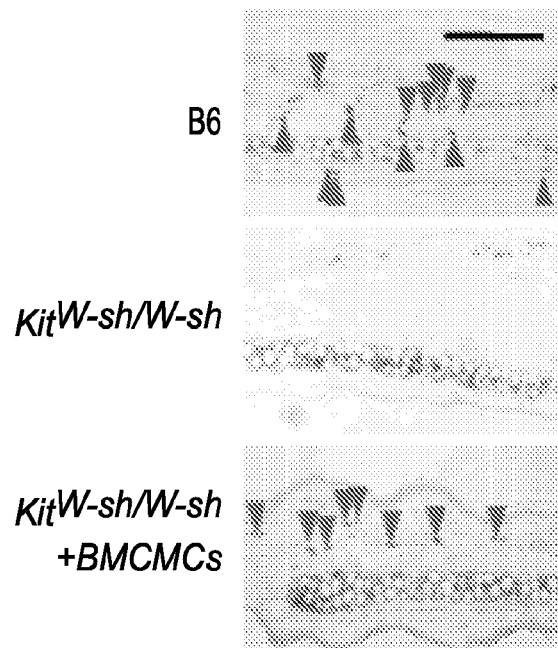
FIG. 32. The number of cutaneous MCs in the ear pina detected by toluidine blue staining. (a) Representative ear histopathology of C57BL6 (B6), $Kit^{W-sh/W-sh}$ and MC-reconstituted $Kit^{W-sh/W-sh}$ mice. Skin sections were stained with toluidine blue. Red arrow heads indicate toluidine-positive MCs. Bar=200 μm. (b) Number of cutaneous MCs detected by toluidine blue staining. Dots represent different high power fields (hpf) from 5 mice. Bars represent the means. *P<0.05, ***P<0.001, Kruskal-Wallis test. Data are representative of three independent experiments.
Figure 32B:
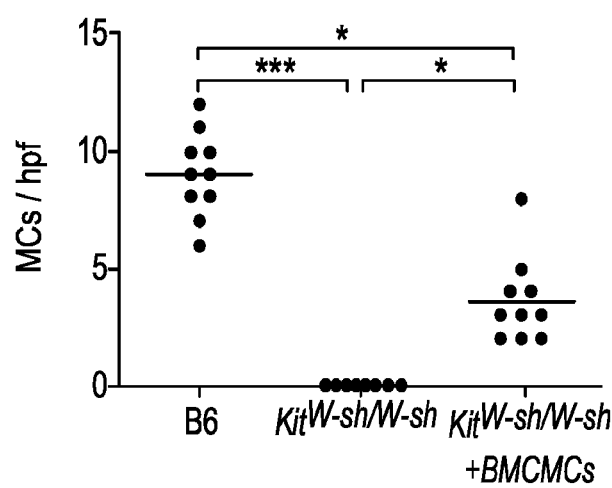

PCA assay was performed as previously described with minor modifications in Wershil, et al., *J Clin Invest* 87, 446-453 (1991). For bone marrow-derived cultured mast cell (BMCMC) reconstitution experiments, $10^6$ BMCMCs in 40 μl of PBS were injected into the ear skin of $Kit^{W-sh/W-sh}$ mice, as described in Grimbaldeston et al., Am. J. Pathol. 167, 835-848 (2005). Four to six weeks later, the mice were subjected to experimental PCA or epicutaneous *S. aureus* sensitization. The reconstitution rate of cutaneous MCs was quantified blindly by an independent observer and scored as number of MCs per low power field in toluidine blue-stained tissue slides by microscope. The average rate of reconstituted MCs was about 40% in the ear pina and about 50% in the back skin (FIGS. 31 and 32). PCA assay was performed as described, with minor modifications. Ears of mice were injected intradermally with or without αDNP-IgE (clone SPE-7, Sigma) in 40 μl saline and 15 hours later, mice were challenged with 20 μl saline with or without synthetic δ-toxin (100 μg or 5 μg). After inoculation, 0.1 ml of 5 mg ml −1 Evans blue dye was injected intravenously. Extravasation of Evans blue dye was monitored for 30 minutes, and 4 mm of punched-out biopsies were incubated at 63° C. overnight in 200 μl formamide. Quantitative analysis of extracts was determined by measuring the absorbance at 600 nm.

Figure 1F:
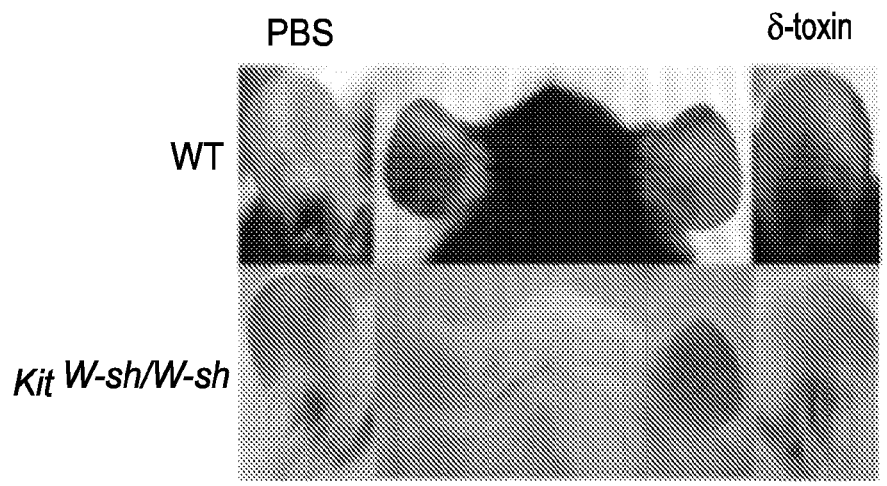
Figure 1G:
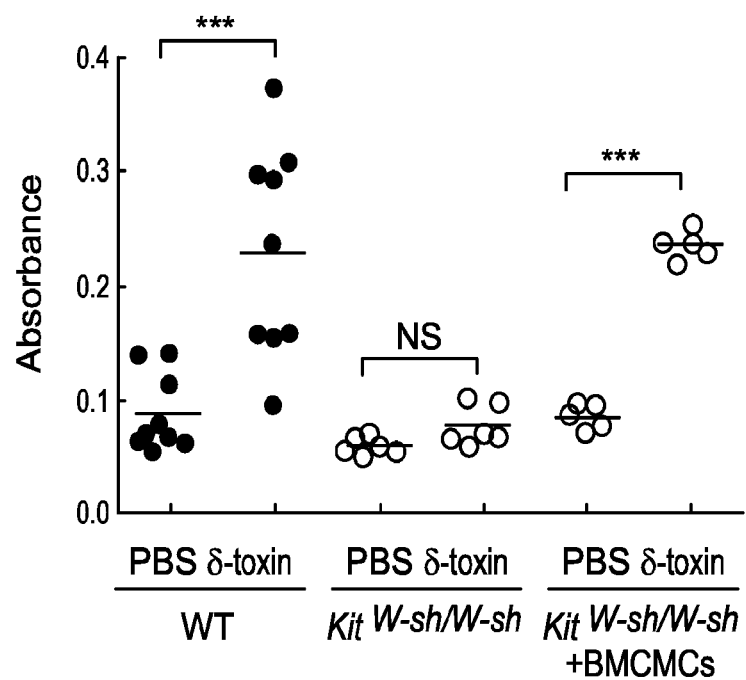

Intradermal administration of δ-toxin induced Evan's blue dye leaking at the site of injection in the ears of wild-type mice, but not in MC-deficient $Kit^{W-sh/W-sh}$ mice (FIGS. 1f and 1g).

Figure 19A:
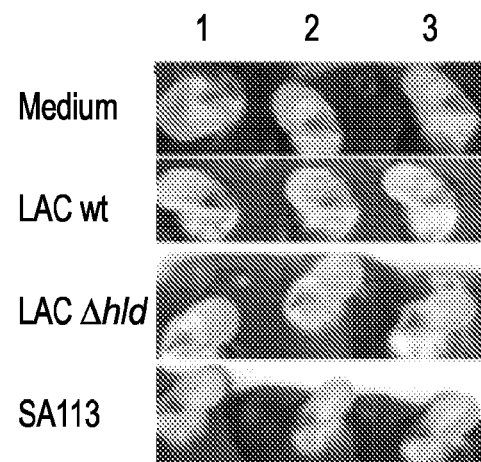
FIG. 19. δ-toxin in *S. aureus* culture supernatant induces MC degranulation in vivo. (a) C57BL6 mice were injected intradermally into the left and right ears with 40% *S. aureus* culture supernatant from LAC wt, LAC Δhld and SA113 or 40% TSB (as control). Culture supernatants were diluted by PBS. Three representative mice for each group are shown. (b) Quantification of Evans blue extracted from skin tissue of C57BL6 mice is shown. Dots represent individual ear samples pooled from three independent experiments. P<0.01, *P<0.001, Kruskal-Wallis test. Bars represent the means.
Figure 19B:
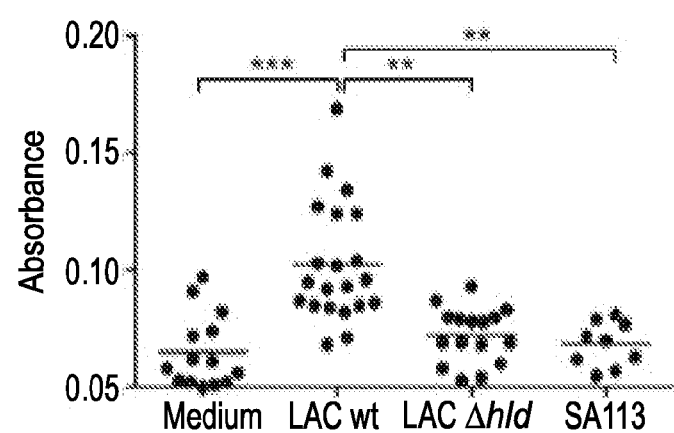

Importantly, reconstitution of the skin of $Kit^{W-sh/W-sh}$ mice with bone marrow-derived MCs (BMDMCs) restored leaking of the dye upon intradermal administration of δ-toxin (FIG. 1g). Moreover, the culture supernatant from the δ-toxin positive LAC strain induced leaking of Evans blue dye whereas that from δ-toxin-negative LACΔhld and SA113 strains did not (FIG. 19). These results indicate that δ-toxin induces MC degranulation in vitro and in vivo.

δ-toxin triggers $Ca^{2+}$ influx through N-formyl peptide receptor 2 (FPR2) in human neutrophils (Kretschmer, D. et al. Human formyl peptide receptor 2 senses highly pathogenic *Staphylococcus aureus*. Kretschmer, et al., *Cell Host Microbe* 7, 463-473 (2010)). Because $Ca^{2+}$ influx is an essential step in MC degranulation, the ability of δ-toxin to induce $Ca^{2+}$ influx in MCs was assessed.

In brief, FSMCs ($2 \times 10^6$ ml$^{-1}$) were preloaded with or without anti-DNP-IgE (0.3 μg ml$^{-1}$) in RPMI with IL-3 for 15 hours. Cells were washed and loaded with Fluo-4AM (5 μM, Life Technologies) for 30 minutes. Cells were washed again and further incubated in Tyrode's buffer with or without EGTA (1 mM) for 30 minutes. DNP-HSA (30 ng ml$^{-1}$), Ionomycin (1 μM) or δ-toxin (30 μg ml$^1$) were used to induce calcium flux in these cells. $Ca^{2+}$ flux was measured using a flow cytometer (FACSCalibur, BD Biosciences) to monitor RFU (relative fluorescence units) as described in Vig, et al. *Nat Immunol* 9, 89-96 (2008).

Figure 2A:
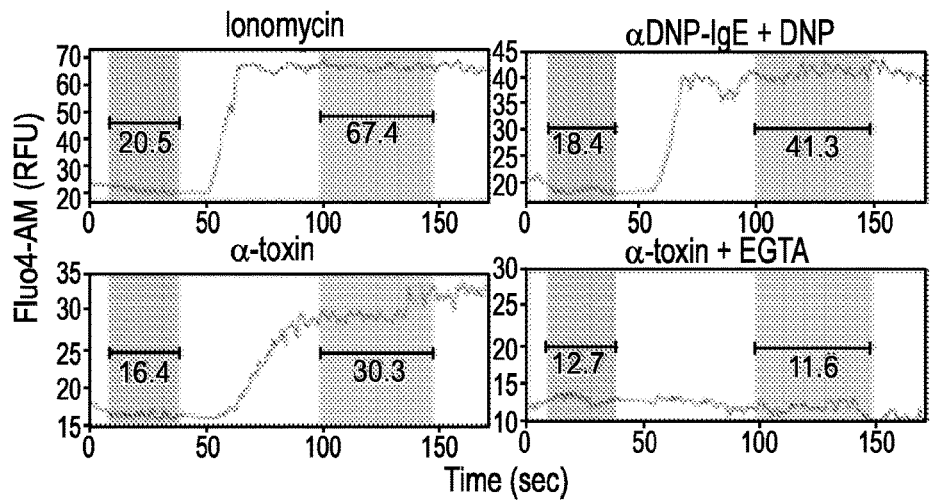
FIG. 2. δ-toxin-induced MC degranulation depends on Ca$^{2+}$ influx/PI3K pathway, but is independent of Syk. a, FSMCs loaded with the fluorescent Ca$^{2+}$ indicator Fluo-4AM with or without EGTA were stimulated for 50 sec. Baseline fluorescence (red) was measured, and then the MCs were stimulated with indicated stimuli and fluorescence shift (green) was measured. RFU, relative fluorescence units. b, c, MC degranulation activity (β-hexosaminidase assay) of supernatants of FSMCs pretreated with EGTA (b) or LY294002 (c) stimulated with medium alone (Crtl), ionomycin, DNP-HSA (DNP) plus anti DNP-IgE or δ-toxin (10 µg ml$^{-1}$). d, MC degranulation activity in FSMCs derived from Syk$^{-/-}$ and wild-type (WT) mice stimulated with indicated concentration of δ-toxin (µg ml$^{-1}$). Data represent means±s.d. of triplicates cultures and representative of at least 3 independent experiments (b-d). NS; no significant; *P<0.05; P<0.01; *P<0.001, 2-tailed t test.

Results showed that stimulation of MCs with ionomycin or DNP plus anti-DNP IgE induced rapid Ca 2+ influx (FIG. 2a).

Figure 2B:
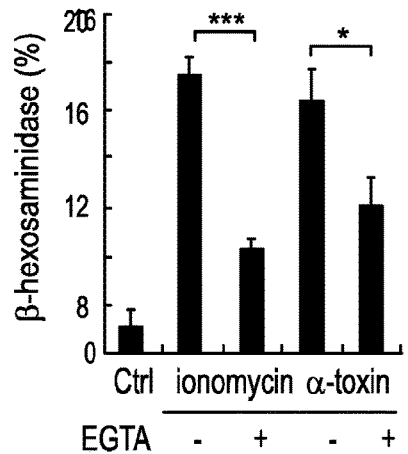
Figure 2C:
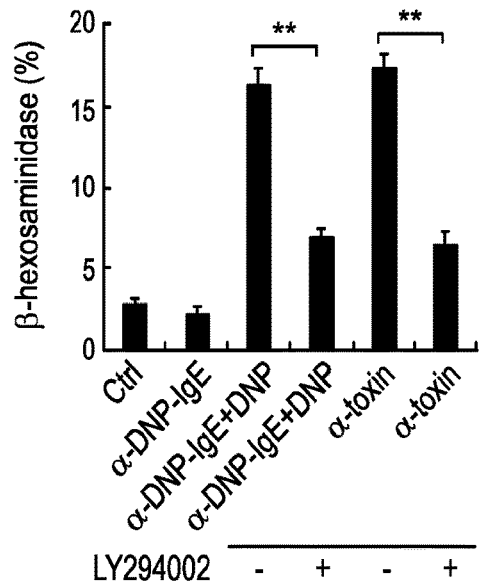

Likewise, δ-toxin triggered $Ca^{2+}$ influx and this was abrogated by treatment with the $Ca^{2+}$ chelator ethylene glycol tetraacetic acid (EGTA) (FIG. 2a). EGTA also blocked MC degranulation induced by ionomycin, DNP plus anti-DNP IgE or δ-toxin, indicating that MC degranulation induced by δ-toxin is mediated through $Ca^{2+}$ influx (FIG. 2b).

Figure 2D:
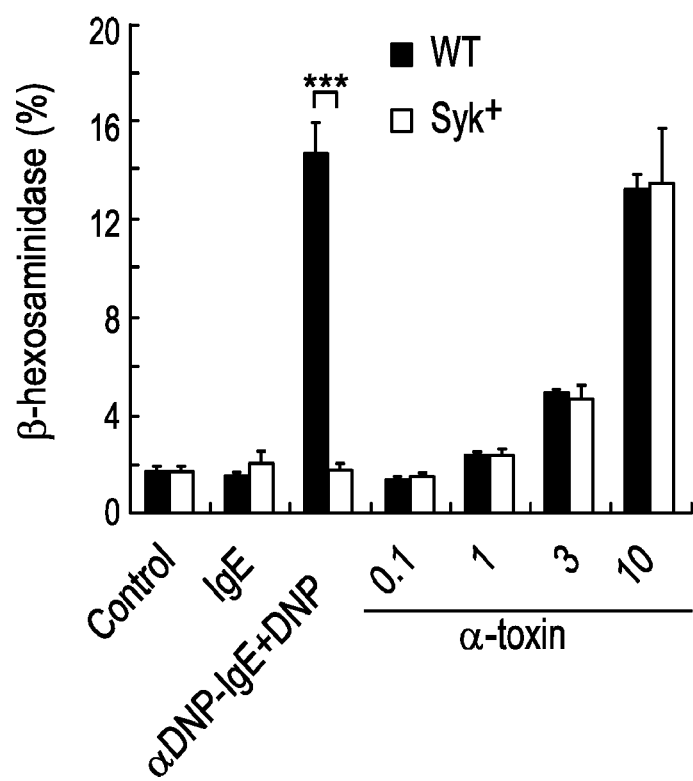
Figure 20:
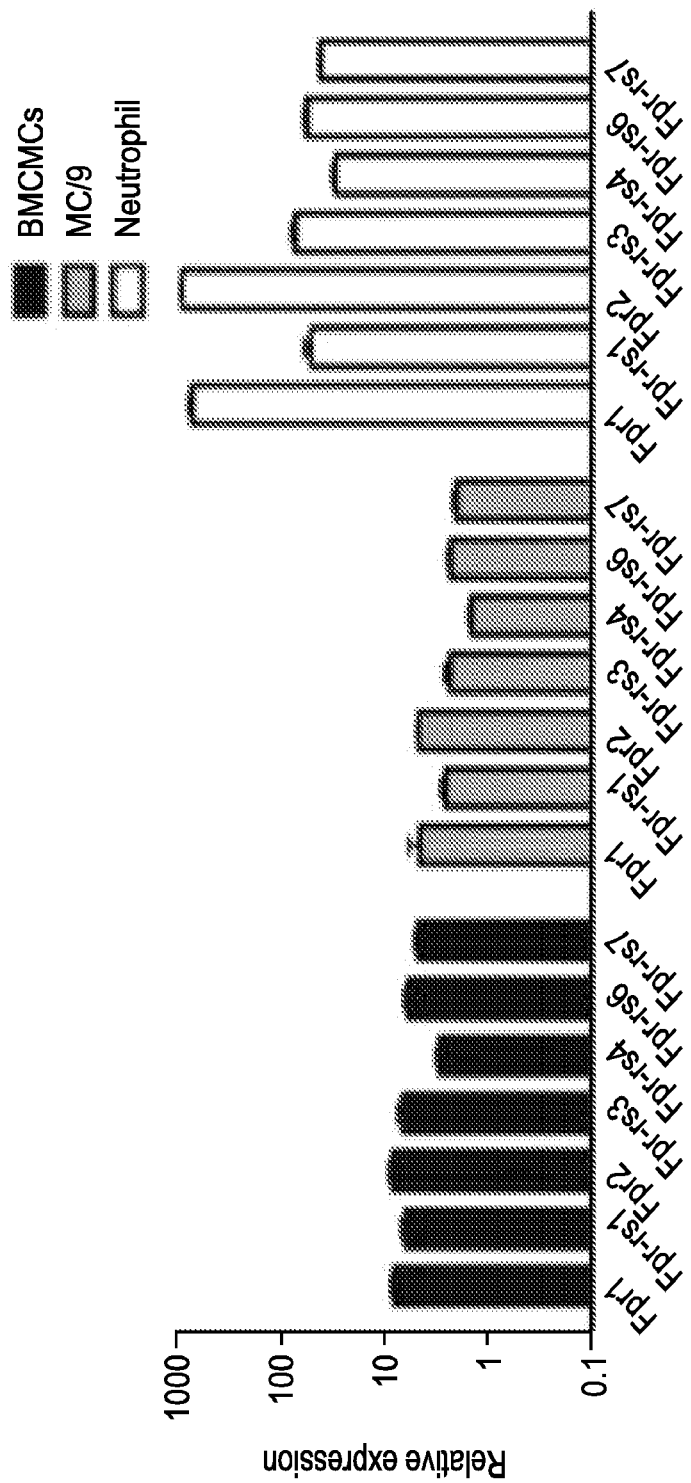
FIG. 20. Mouse Fpr gene expression. Expression of mouse Fpr genes in BMCMCs, MC/9 and bone marrow neutrophils. Expression is normalized to that of Gapdh. Data represent means±s.d. of triplicate cultures. Data are representative of two independent experiments.
Figure 21A:
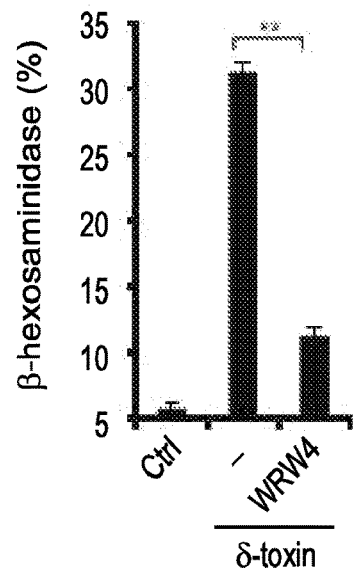
FIG. 21. MC degranulation activity induced by δ-toxin is inhibited by FPR antagonists. (a) MC degranulation activity (β-hexosaminidase assay) of supernatants of MC/9 cells pretreated with WRW4 peptide and then stimulated with δ-toxin (10 μg ml−1). (b) Quantification of Evans blue extracted from skin tissue of C57BL6 mice is shown. Mice were pretreated with or without WRW4 peptides (100 μM). One hour later, mice were injected intradermally into the ears with 40% culture supernatant from *S. aureus*. Dots represent individual ear samples. (c) β-hexosaminidase assay of supernatants of MC/9 cells pretreated with FPR1 antagonist (Cyclosporin H) and then stimulated with δ-toxin (10 μg ml-1). Data represent means±s.d. of triplicate cultures. In a,c, P<0.01, *P<0.001, two-tailed Student's t-test. In b, NS; not significant, **P<0.01, Kruskal-Wallis test. Bars represent the means. Data are representative of three independent experiments.
Figure 21B:
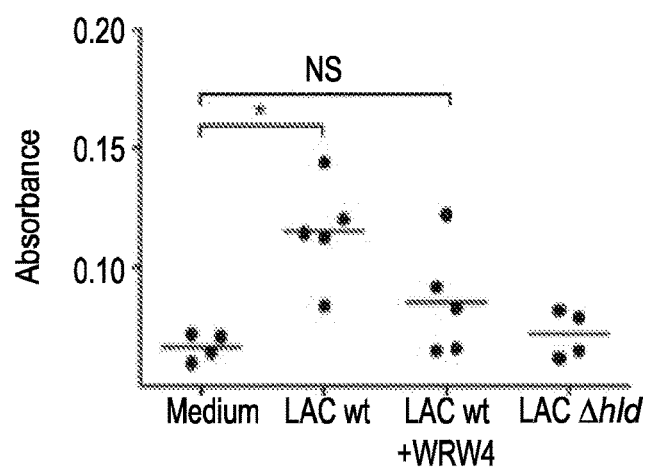
Figure 21C:
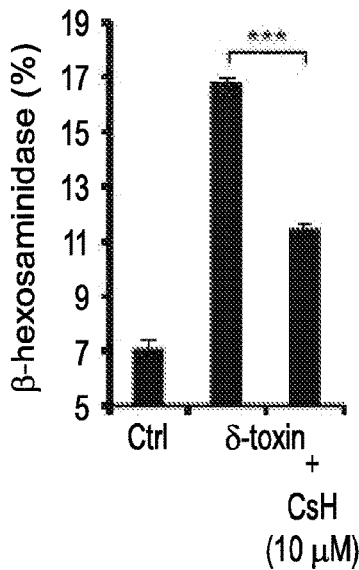
Figure 22A:
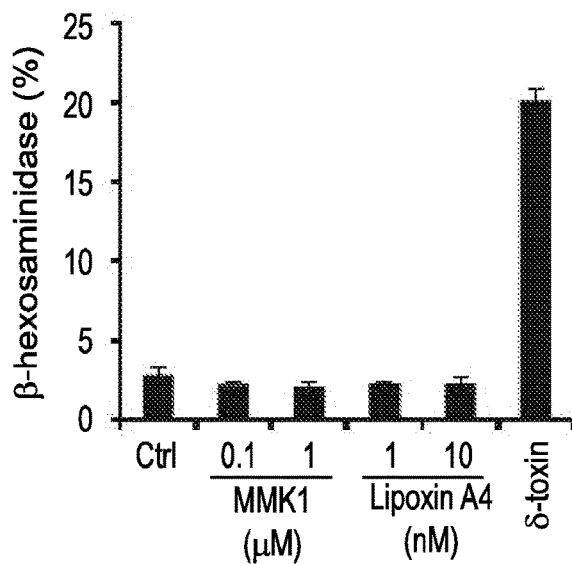
FIG. 22. Fpr2 is dispensable for MC degranulation activity induced by δ-toxin. (a) MC degranulation activity (β-hexosaminidase assay) in supernatants of MC/9 cells treated with indicated concentration of FPR2 agonists (MMK1, LipoxinA4). (b) MC degranulation activity of supernatants of MC/9 cells pretreated with pertussis toxin (PTX; 100 ng ml-1 and 200 ng ml−1) overnight and then stimulated with indicated concentrations of δ-toxin (μg ml-1). (c) β-hexosaminidase assay of supernatants of BMCMCs from WT and Fpr2$^{-/-}$ mice stimulated with δ-toxin (10 μg ml-1). Data represent means±s.d. of triplicate cultures. In b, *P<0.05, **P<0.01, two-tailed Student's t-test. Data are representative of three independent experiments.
Figure 22B:
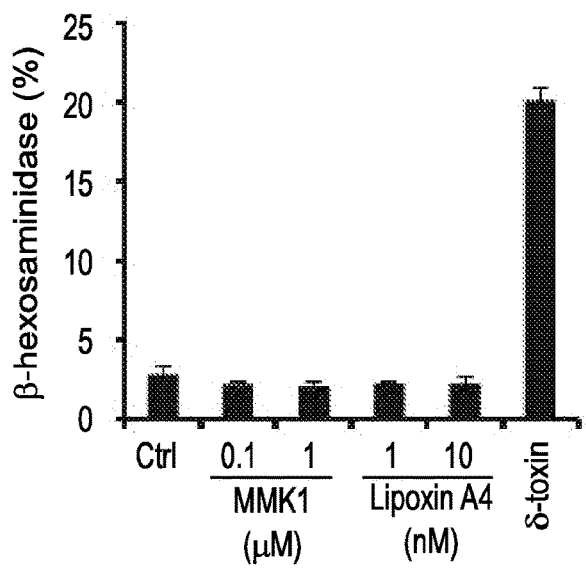
Figure 22C:
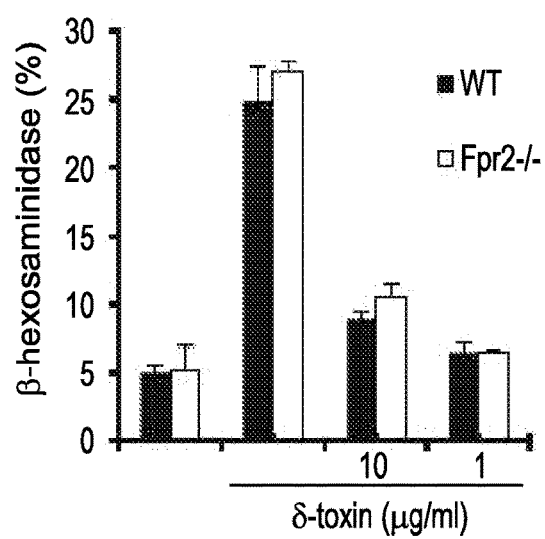

Similarly, MC degranulation induced by DNP plus anti-DNP IgE or δ-toxin was inhibited by the PI3 kinase inhibitor, LY294002, indicating that MC degranulation triggered by δ-toxin shares signaling events with those that are elicited by IgE crosslinking (FIG. 2c). However, unlike the MC degranulation triggered by antigen plus IgE, MC degranulation induced by δ-toxin did not require Syk (FIG. 2d). Fpr1, Fpr2 and related family members were expressed in mouse MCs, although their expression was higher in neutrophils (FIG. 20). Notably, pre-treatment of MCs with WRW4, a selective peptide antagonist of formyl peptide receptor-like 1 (FPRL1) that blocks human neutrophil activation induced by δ-toxin in vitro (Nielsen et al., Infect. Immun. 67:1045-1049 (1999)), inhibited MC degranulation induced by δ-toxin both in vitro and in vivo (FIGS. 21a and 21b). Cyclosporin H (CsH), an antagonist of human FPR1, also partially inhibited mouse MC degranulation induced by δ-toxin (FIG. 21c). However, human FPR2 ligands, MMK1 and Lipoxin A4, did not induce mouse MC degranulation (FIG. 22a). Furthermore, treatment with pertussis toxin (PTX), an inhibitor of G-protein coupled receptors, partially reduced MC degranulation induced by δ-toxin (FIG. 22b). However, MCs from wild-type and $Fpr2^{-/-}$ mice exhibited comparable MC degranulation induced by δ-toxin (FIG. 22c).

Collectively, these results indicate that δ-toxin induces MC degranulation via a signaling pathway that is different from that used by antigen and IgE.

Crosslinking of IgE Fc receptors by IgE and antigen, but not monomeric IgE, induces robust MC degranulation (Leung, et al., *Lancet* 361, 151-160, doi:S0140-6736(03) 12193-9 (2003)). However, stimulation with monomeric IgE can increase MC degranulation induced by certain molecules including compound 48/80 and substance P (Yamada, et al., *J Invest Dermatol* 121, 1425-1432, (2003)). Therefore, the ability of monomeric IgE to enhance the ability of δ-toxin to induce MC degranulation was tested.

Figure 3A:
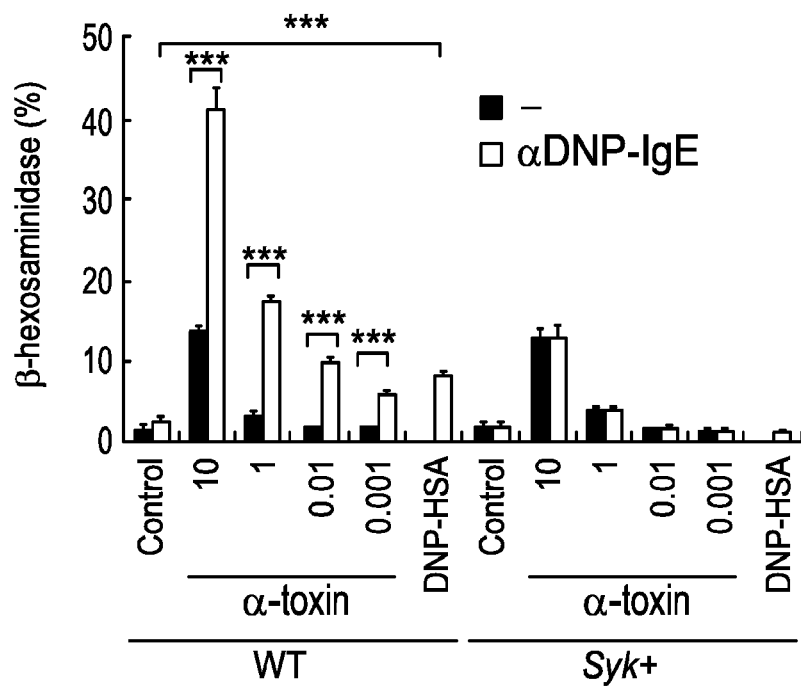
FIG. 3. Antigen-independent IgE signaling enhances δ-toxin-induced MC activation. a, MC degranulation activity in supernatants of FSMCs with or without anti DNP-IgE or TNP-IgE and then stimulated with δ-toxin (0.01 µg ml$^{-1}$), DNP-HSA (DNP) or TNP-HSA (TNP). b, MC degranulation activity in supernatants of FSMCs derived from Syk$^{-/-}$ and wild-type mice (WT) pretreated with or without anti DNP-IgE, and then stimulated with indicated concentration of δ-toxin (µg ml$^{-1}$). Representative of at least 3 independent experiments. P<0.01; *P<0.001, 2-tailed t test (a,b). Quantification of Evans blue extracted from skin tissue of C57BL6 mice injected intradermally into the left and right ears with δ-toxin (5 µg) or PBS, respectively. Data represent means±s.d. of triplicate cultures and representative of at least 3 independent experiments (a,b). Dots represent individual ear samples. Representative of 2 independent experiments. NS; no significant; *P<0.05, one-way ANOVA with Tukey post-hoc test for multiple comparisons.
Figure 3B:
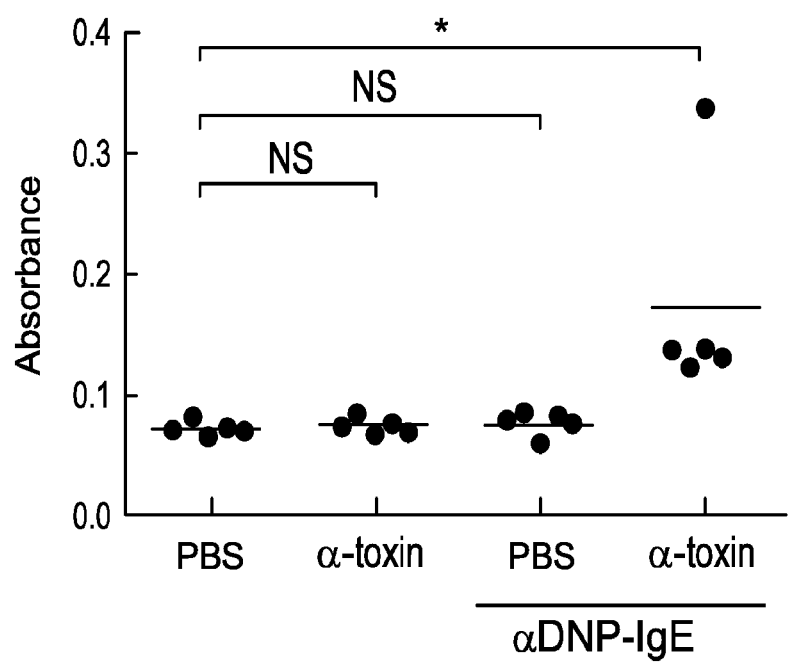

Pre-incubation of MCs with anti-DNP IgE or anti-TNP IgE alone dramatically increased the degranulation activity of δ-toxin (FIG. 3a). Notably, the synergistic effect of monomeric aDNP-IgE and δ-toxin was abrogated in MCs deficient in Syk (FIG. 3b).

To test whether the synergism between monomeric IgE and δ-toxin could be observed in vivo, monomeric IgE and δ-toxin were injected into the skin of mice at concentrations that do not induce MC degranulation and MC degranulation was monitored in vivo with the PCA assay. At these low concentrations, δ-toxin induced Evans blue dye leaking at the site of injection in mice pretreated with anti DNP IgE (FIG. 3b).

These results indicate that IgE increases the MC degranulation activity of δ-toxin in the absence of antigen.

Example 6

Figure 23A:
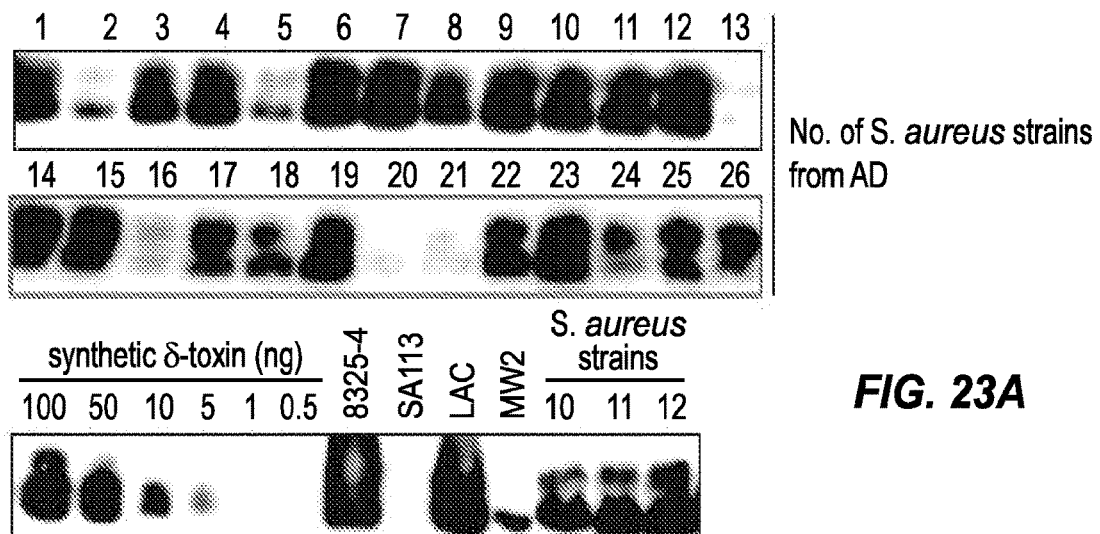
FIG. 23. *S. aureus* RNAIII is expressed in the lesional skin of human atopic dermatitis patients. (a) Immunoblot analysis of culture supernatants of 26 *S. aureus* strains (0.25 μl per well) that were isolated from the skin of atopic dermatitis skin lesions. Indicated amounts of synthetic δ-toxin were also loaded as controls. All isolates were methicillin-sensitive *S. aureus* except No. 23, which was community-associated methicillin-resistant *S. aureus*. Data are representative of at least two independent experiments. (b) *S. aureus* RNAIII expression in AD skin obtained from lesional and non-lesional skin. Expression was normalized to the *S. aureus* housekeeping gene, gyrB. LAC wt and LAC Δagr cultured 24 hours are shown as reference controls. (c) Expression of *S. aureus* gyrB was normalized to bacterial 16S rRNA. Samples that were negative for gyrB expression were also negative for RNAIII. ND; not detected. NS; not significant, **P<0.01, Wilcoxon test. Dots represent individual patient samples. Bars represent the means. Data are representative of three independent experiments.
Figure 23B:
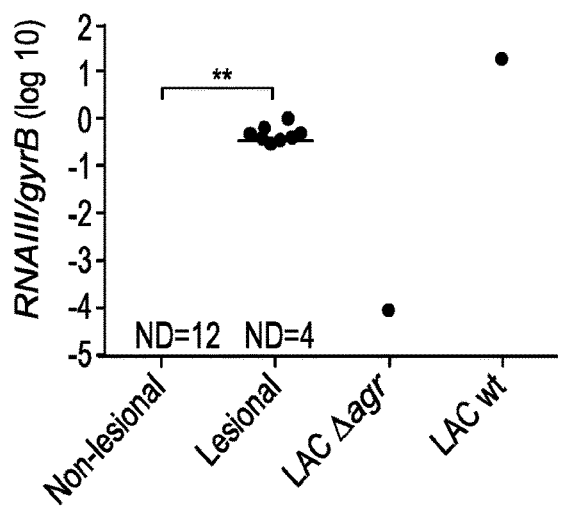
Figure 23C:
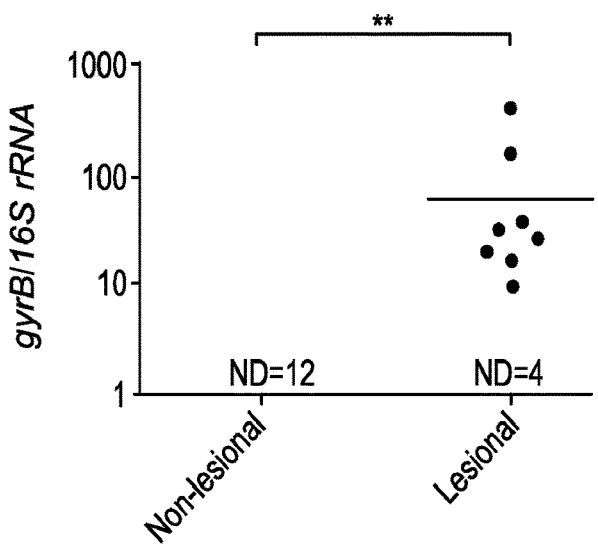

In view of the results above, an assay was designed to determine whether S. aureus isolates from the lesional skin of AD patients express δ-toxin. Notably, all supernatants from 26 S. aureus strains isolated from the lesional skin of AD patients produced δ-toxin (FIG. 23a). Moreover, RNAIII expression was detected in lesional skin colonized with S. aureus, but not normal skin, of AD patients (FIGS. 23b and 23c).

Figure 4A:
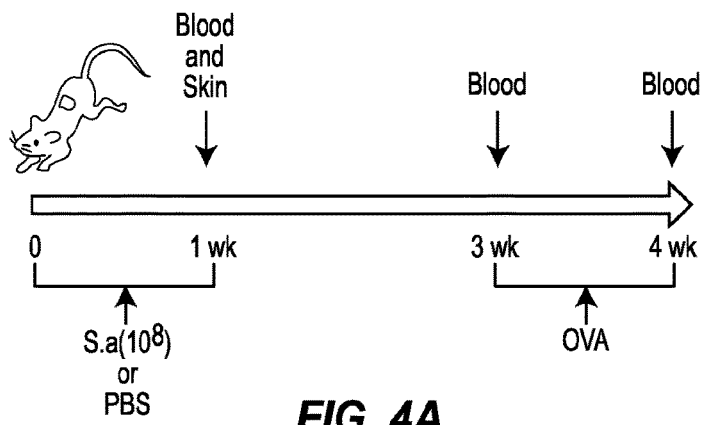
FIG. 4. *Staphyloccocus* δ-toxin promotes IgE production and inflammatory skin disease via mast cells. a, *S. aureus* colonization and OVA sensitization protocol. Mice were colonized epicutaneously with 10$^8$ CFU *S. aureus* using a gauze patch for 1 week. For OVA sensitization, a patch containing OVA or PBS was applied to the same skin site 2 weeks after *S. aureus* inoculation. b, Skin disease score 1 week post colonization with wild-type and δ-toxin mutant (Δhld) *S. aureus* or treated with PBS. P<0.01; *P<0.001, Kruskal-Wallis test with post-hoc Dunn's test for multiple comparisons. c, Representative skin phenotype and histopathology of BALB/c mice colonized with *S. aureus* or treated with PBS. Skin sections were stained with H&E. Bar=100 µm. Inset shows high power image with neutrophil-rich inflammation. d, Number of inflammatory cells in skin of BALB/c mice colonized with *S. aureus* or treated with PBS. Results depicted as number of inflammatory cells per high power field (hpf). e, Serum levels of IgE in BALB/c mice colonized with *S. aureus* or treated with PBS at 1 and 3 weeks post colonization with *S. aureus*. f, Serum levels of OVA-specific IgE after OVA sensitization in BALB/c mice colonized with *S. aureus* or treated with PBS. g, Skin disease score in C57BL/6 (B6), MC-deficient (Kit$^{W-sh/W-sh}$) and MC-deficient (Kit$^{W-sh/W-sh}$) mice reconstituted with MCs at 1 week after the inoculation with *S. aureus*. h, Serum levels of total IgE 1 week after colonization of B6, Kit$^{W-sh/W-sh}$ and Kit$^{W-sh/W-sh}$ mice reconstituted with MCs with wild-type and δ-toxin mutant (Δhld) *S. aureus* or treated with PBS. Dots represent individual mice pooled from two independent experiments. *P<0.05; P<0.01; *P<0.001, one-way ANOVA with Tukey post-hoc test for multiple comparisons (d-h).

To test whether δ-toxin plays a role in allergic skin disease, a modified epicutaneous disease model was used in which the skin of BALB/c mice previously colonized with wild-type or δ-toxin-deficient S. aureus was challenged once with ovalbumin (OVA) to assess antigen-specific IgE production (FIG. 4a). This epicutaneous OVA sensitization model in mice was carried out as previously described, with modifications in Spergel, et al., J Clin Invest 101, 1614-1622 (1998).

Figure 4B:
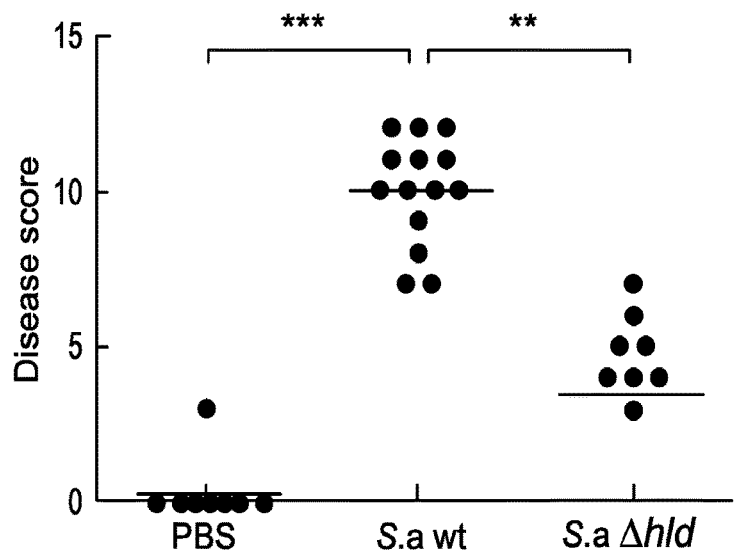
Figure 4C:
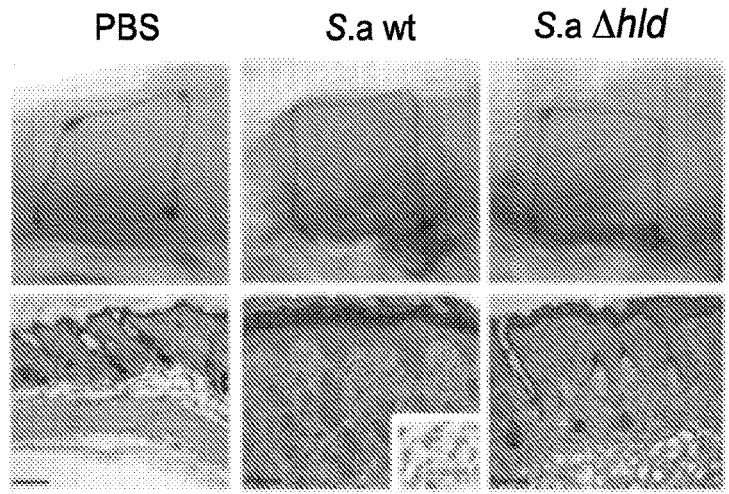
Figure 24A:
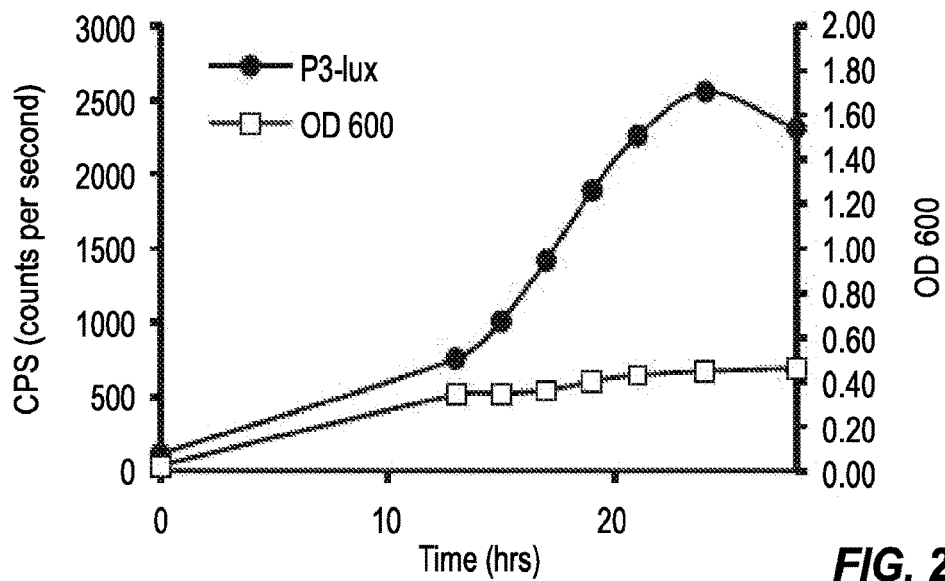
FIG. 24. δ-toxin gene expression in vivo. (a) δ-toxin gene expression of LAC P3-lux strain in TSB culture. P3-lux expression and bacterial concentration (Optical Density 600; OD600) were measured by LMax luminometer (Molecular Device). (b) Representative expression of S. aureus δ-toxin RNA 4 days after S. aureus colonization. Expression was detected by bioluminescence of S. aureus LAC wt and LAC P3-lux strains on a color scale overlaid on top of a grayscale image of mice. (c) Luminescence expression and the number of S. aureus in the skin of infected mice. Dot line represents the background level of luminescence. Data represent means+s.e.m. (day 1; n=5 mice, day 4 and 7; 4 mice pooled from 3 independent experiments.).
Figure 24B:
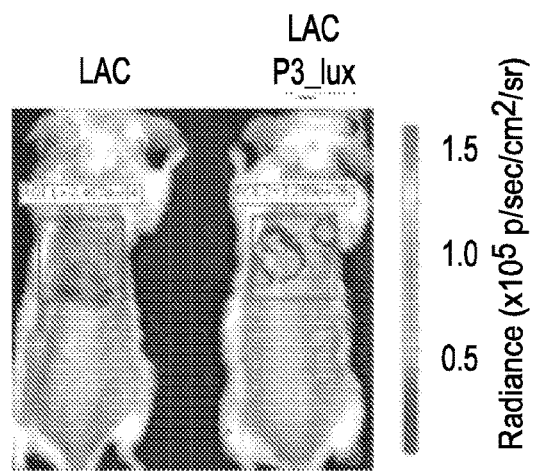
Figure 24C:
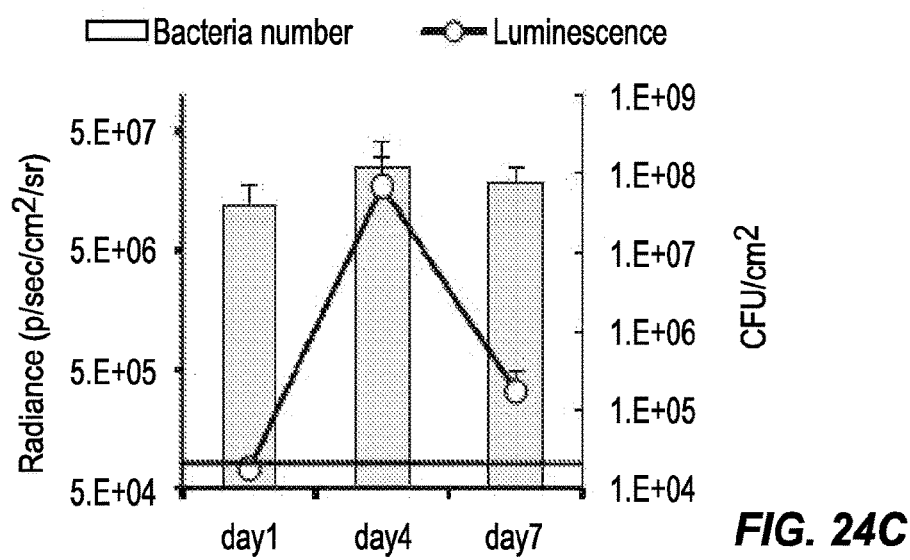

Briefly, the dorsal skin of 6- to 8-week-old female mice was shaved and stripped, three times, using a transparent bio-occlusive dressing (Tegaderm®; 3M). After overnight culture at 37° C. with shaking, S. aureus were cultured in fresh TSB medium for 4 hours at 37° C. with shaking, washed and resuspended in PBS at $10^8$ CFU of S. aureus LAC or LAC (Δhld) strains. 100 μl of the S. aureus suspension was placed on a patch of sterile gauze (1 cm×1 cm) and attached to shaved skin with a transparent bio-occlusive dressing. Each mouse was exposed to S. aureus for 1 week through the patch. One week after colonization with wild-type S. aureus, the mice developed severely inflamed reddened skin at the site of application (FIGS. 4b and 4c). Expression of hld was detected in the skin on day 4 after wild-type S. aureus colonization using a bioluminescent reporter S. aureus strain (FIG. 24). After a 2-week interval, each mouse was challenged once with 100 μg ovalbumin (OVA, Grade V, Sigma) epicutaneously for 1 week and the animals were sacrificed for analyses. For the OVA sensitization model, BALB/c mice were sensitized epicutaneously with OVA (100 μg) with or without synthetic δ-toxin (100 μg) at the same skin site.

For histological analysis, skin tissue was formalin-fixed, paraffin-embedded and sectioned for H&E and Toluidine blue staining.

Figure 4D:
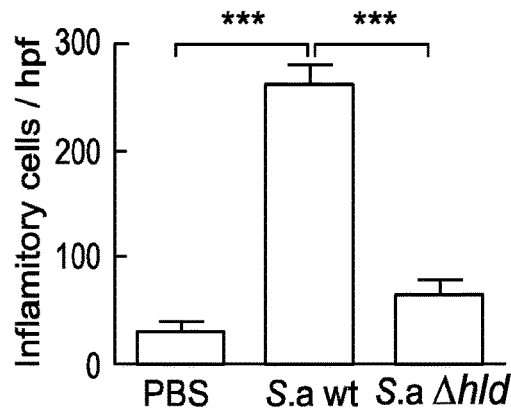
Figure 4E:
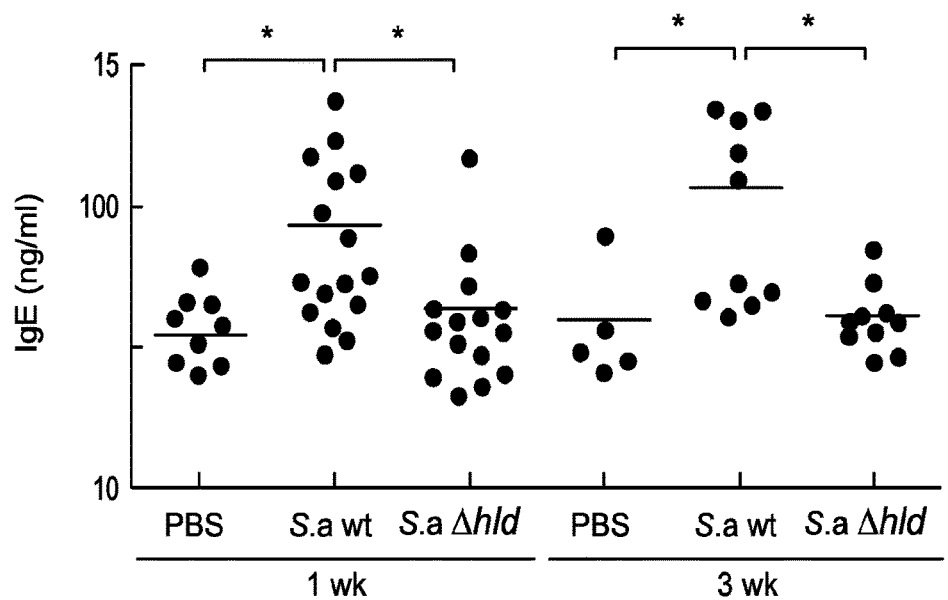
Figure 25A:
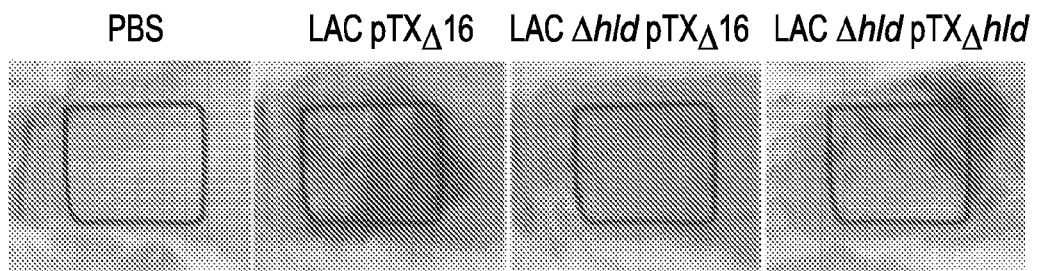
FIG. 25. δ-toxin-complemented S. aureus strain induces skin inflammation. (a) Representative skin phenotype and histopathology of BALB/c mice colonized with S. aureus wild-type (LAC pTx Δ 16), δ-toxin mutant (LACΔhld pTx Δ 16), δ-toxin-complemented strain (LACΔhld pTx Δ hld), or treated with PBS. (b) Skin disease score at 1 week post-colonization with S. aureus or treated with PBS. Dots represent individual mice pooled from two independent experiments. *P<0.05; ***P<0.001, Kruskal-Wallis test.
Figure 25B:
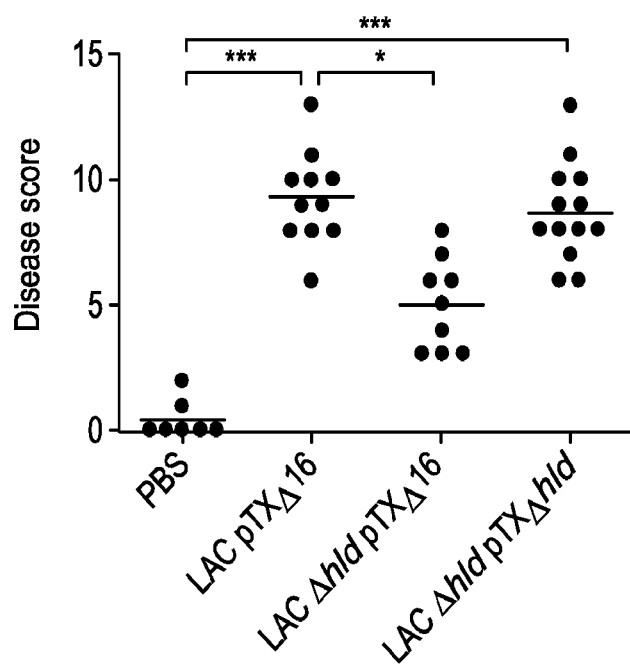
Figure 26A:
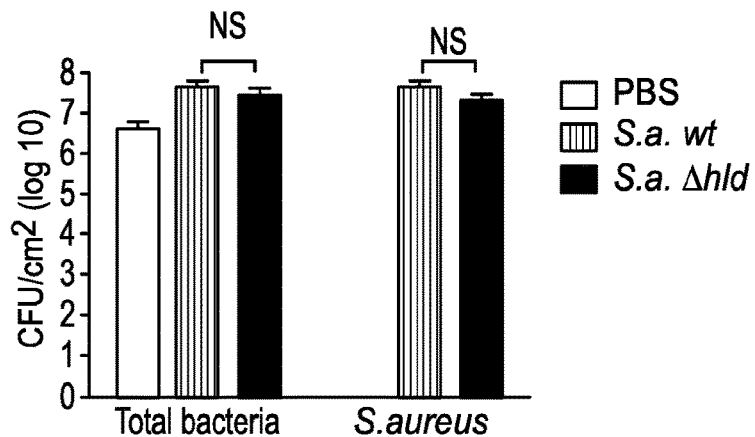
FIG. 26. The number of bacteria and IL-4 levels in skin colonized with S. aureus. (a and b) Number of culturable bacteria and S. aureus in the skin of BALB/c mice 1 week post-inoculation with S. aureus. Results are mean±s.e.m. (n=5). (a) Swabbed samples were plated on TSB and Baird-Parker agar plates, and colonies were counted 48 hours later. (b) Swabbed (surface) and skin homogenized (nonsurface) samples were plated on Baird-Parker agar plates, and colonies were counted 48 hours later. (c) IL-4 levels in skin of Balb/c mice inoculated with or without S. aureus (S.a. wt or S.a. Δhld) for 1 week. Dots represent individual mice. In a, b, NS—not significant, two-tailed Student's t-test. ND; not detected. In c, NS—not significant; *P<0.05, **P<0.01, Kruskal-Wallis test. Data are representative of at least two independent experiments.
Figure 26B:
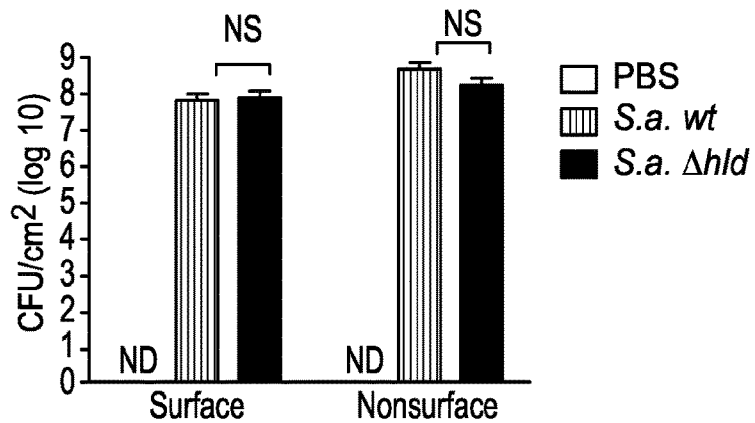
Figure 26C:
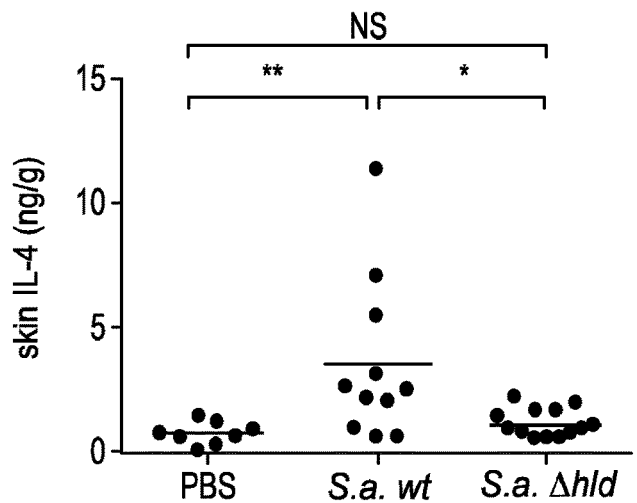
Figure 27A:
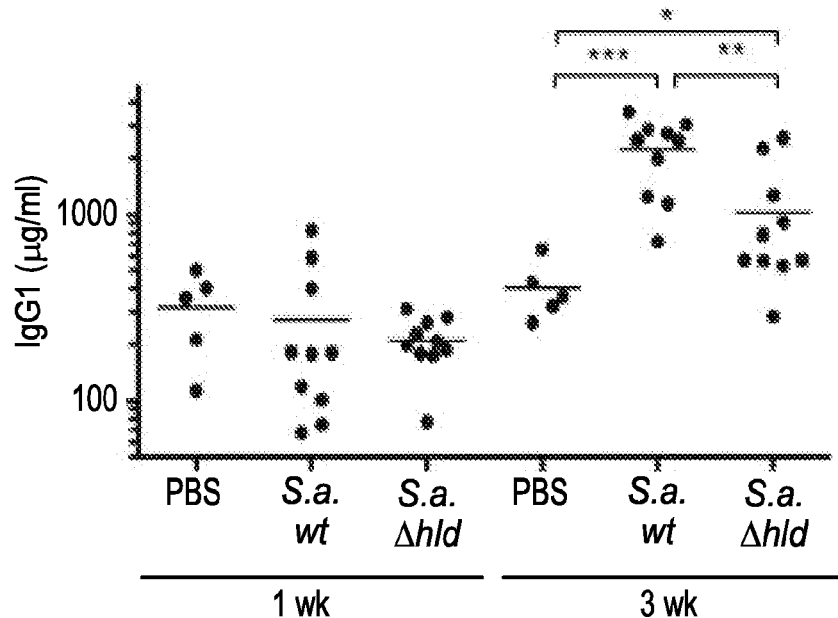
FIG. 27. IgG production in BALB/c mice colonized with S. aureus. Serum levels of IgG1 (a) and IgG2a (b) in BALB/c mice colonized with S. aureus or treated with PBS at 1 week and 3 weeks post-colonization with S. aureus. Dots represent individual mice. NS; not significant; *P<0.05, P<0.01,*P<0.001, Kruskal-Wallis test. Bars represent the means. Dots represent individual mice pooled from two independent experiments.
Figure 27B:
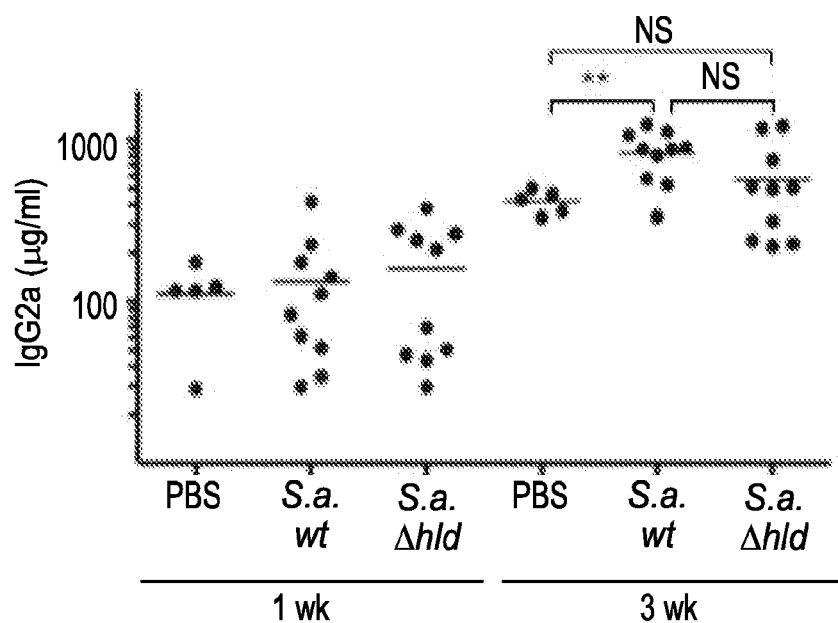

Histological analysis revealed spongiosis and parakeratosis in the epidermis and marked neutrophil-rich inflammatory infiltrates in the dermis of mice colonized with wild-type S. aureus (FIGS. 4c and 4d). In contrast, mice colonized with S. aureus lacking δ-toxin exhibited a significantly reduced skin inflammatory cell infiltrate and disease score (FIGS. 4c, 4b and 4d). Complementation of the Δhld mutant with a plasmid producing δ-toxin restored the disease score to levels comparable to the wild-type bacterium (FIG. 25). The differential ability of wild-type and mutant S. aureus to promote inflammatory disease was not explained by differences in skin colonization (FIGS. 17a, 26a and 26b). Furthermore, mice colonized with wild-type S. aureus developed greater amounts of total serum IgE and IgG1, but not IgG2a, as well as IL-4 in the skin than mice inoculated with the δ-toxin mutant bacterium (FIGS. 4e, 26c, and 27).

Figure 4F:
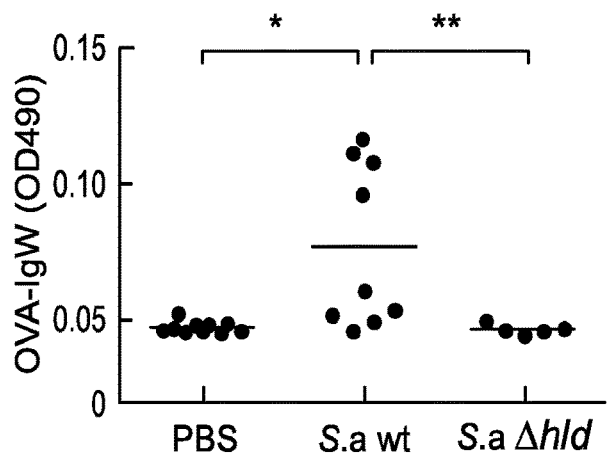
Figure 28A:
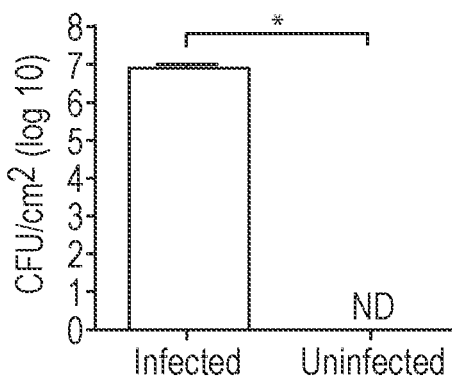
FIG. 28. Colonization of S. aureus without skin tape stripping induces inflammatory disease and IgE production. (a) Number of S. aureus in the total skin of C57BL6 mice colonized with S. aureus or treated with PBS at 1 week. Samples were homogenized and plated on Baird-Parker agar plates, and colonies were counted 48 hours later. Results are mean±s.e.m. (b) Skin disease score in C57BL6 mice at 1 week. (c) Serum levels of IgE in C57BL6 mice at 1 week. *P<0.05, Mann-Whitney test. Bars represent the means. Dots represent individual mice. Data are representative of at least two independent experiments.
Figure 28B:
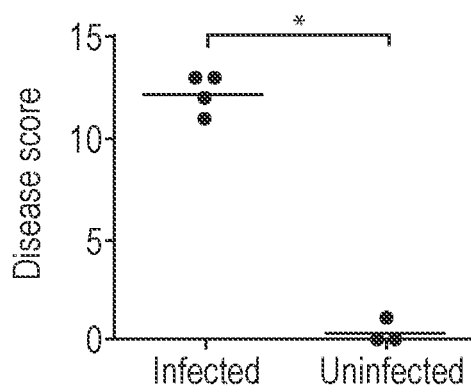
Figure 28C:
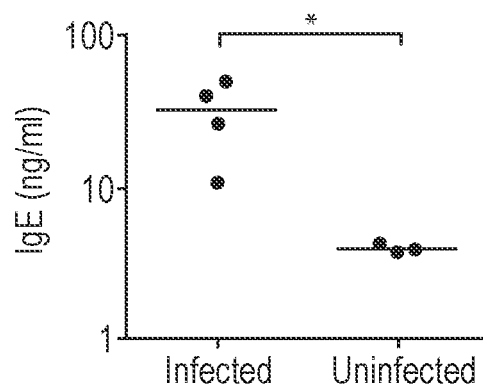
Figure 29A:
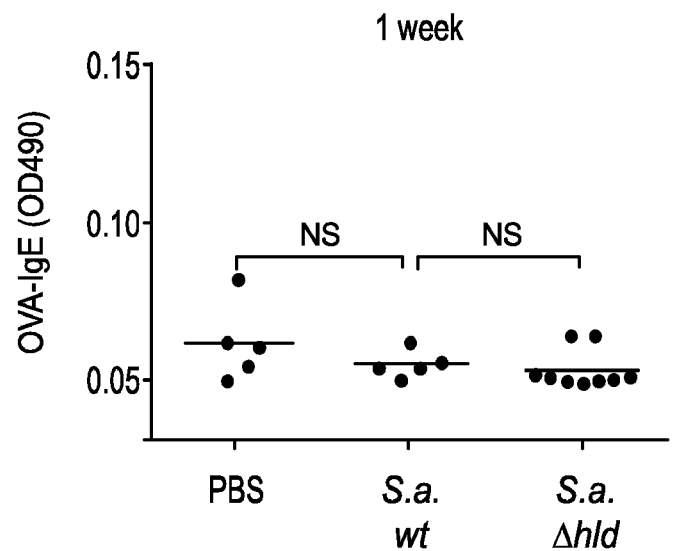
FIG. 29. S. aureus colonization after OVA administration does not induce OVA-IgE. (a) BALB/c mice were exposed epicutaneously with $10^8$ CFU S. aureus (LAC wt and LAC Δhld) and 100 μg OVA at the same time using a gauze patch for 1 week. Sera were collected at 1 week. (b) 100 μg OVA was given epicutaneously using a gauze patch for 1 week. After 1 week interval, BALB/c mice were exposed to $10^8$ CFU S. aureus (LAC wt and LAC Δhld) for 1 week. Sera were collected at 3 weeks. Serum IgE levels were measured by ELISA. NS; no significant, Kruskal-Wallis test. Bars represent the means. Data are representative of two independent experiments.
Figure 29B:
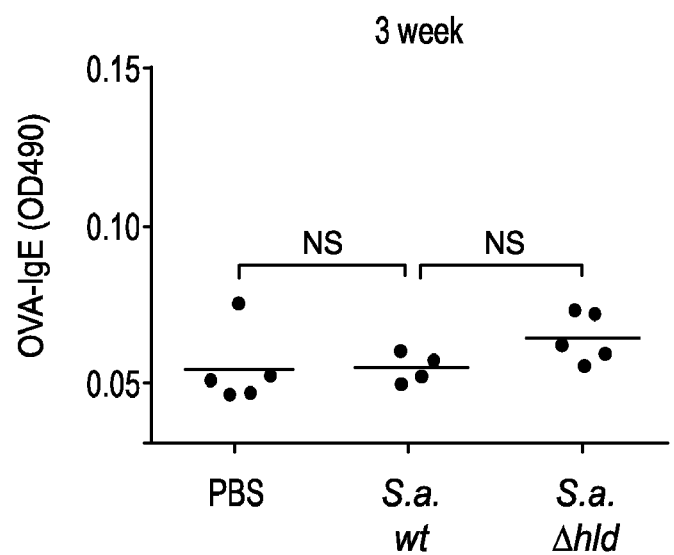
Figure 30A:
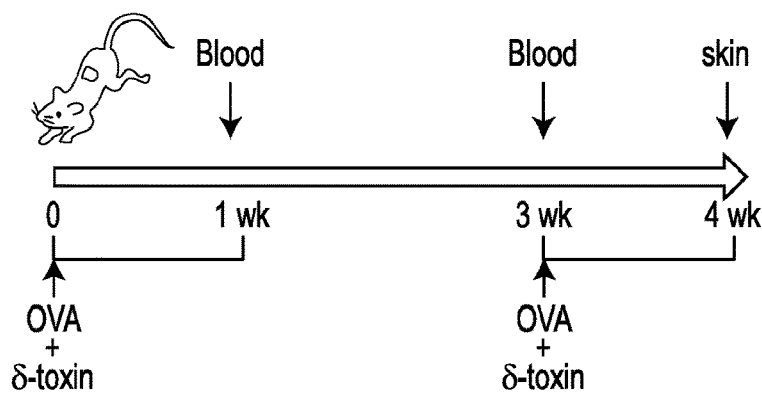
FIG. 30. Synthetic δ-toxin enhances allergic skin disease. (a) OVA sensitization protocol with or without δ-toxin. BALB/c mice were sensitized epicutaneously with OVA (100 μg) with or without synthetic δ-toxin (100 μg) for 1 week. After 2 week interval, mice were challenged with OVA (100 μg) with or without synthetic δ-toxin (100 μg) at the same skin site. (b) Representative skin phenotype (top panels) and histopathology (bottom panels) of mice. Notice white scaly areas as well as thickened epidermis and dermal inflammatory infiltrate in the skin of mice challenged with OVA plus δ-toxin. Skin sections were stained with H&E (HE). Bar=200 μm. (c) Skin disease score at 1 week and 4 weeks. Kruskal-Wallis test. (d-f) Serum levels of OVA specific IgE (d), IgG1(e) and IgG2a (f) in BALB/c sensitized with OVA with or without δ-toxin at 1 week and 3 weeks. Dots represent individual mice. NS; no significant, *P<0.05, P<0.01, *P<0.001, Kruskal-Wallis test. Bars represent the means. Data are representative of two independent experiments.
Figure 30B:
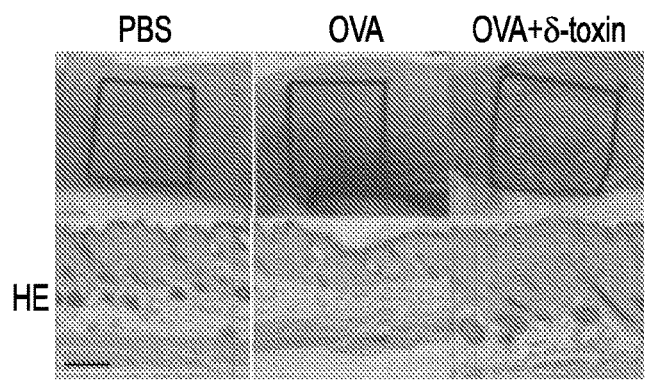
Figure 30C:
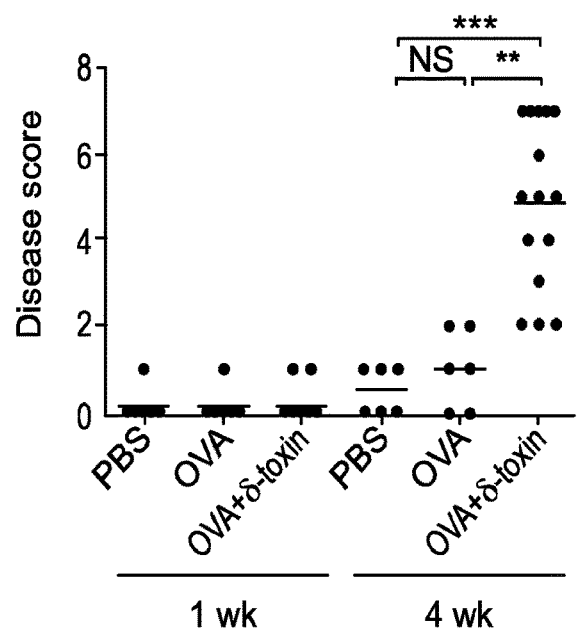
Figure 30D:
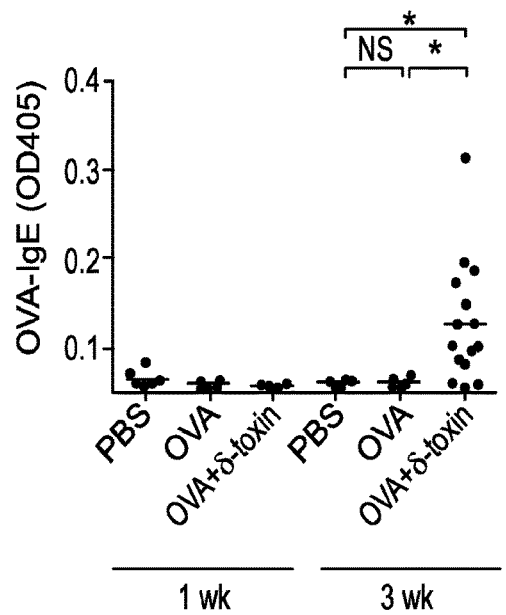
Figure 30E:
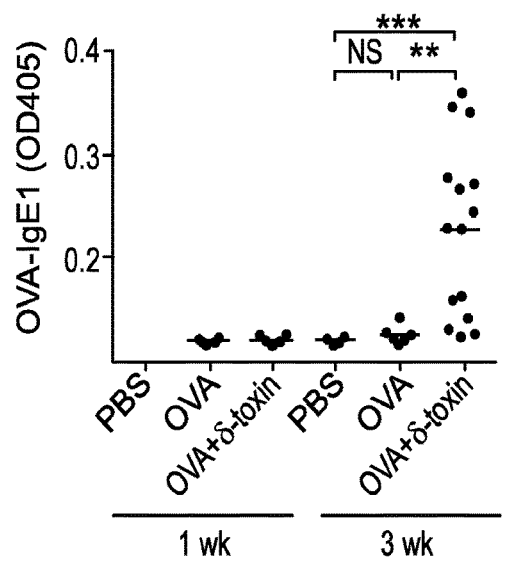
Figure 30F:
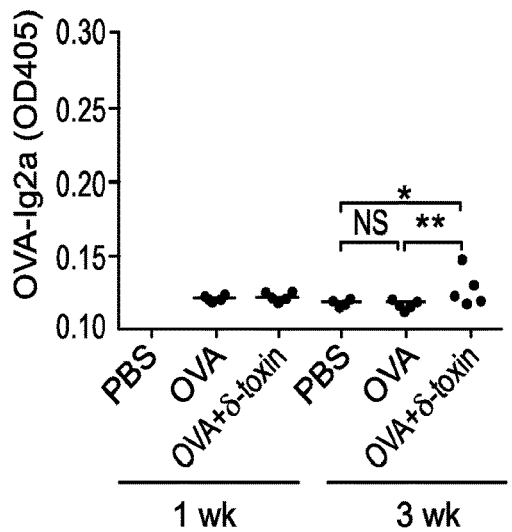

At three weeks, there was a slight increase in IgG1 production in mice colonized with the δ-toxin mutant bacterium compared to PBS control (FIG. 27), providing evidence of the existence of a minor S. aureus-dependent, but δ-toxin-independent pathway for IgG1 production. In addition, pre-colonization with wild-type, but not the δ-toxin-deficient, S. aureus enhanced the production of OVA-specific IgE (FIG. 4f). Colonization with S. aureus without disrupting the skin barrier by stripping also induced inflammatory disease and enhanced IgE responses (FIG. 28). Pre-colonization with δ-toxin-producing S. aureus was important to elicit antigen-specific IgE because administration of OVA prior to, or concurrent with, S. aureus colonization did not enhance OVA-specific IgE production (FIG. 29). To test whether δ-toxin is sufficient to trigger allergic skin disease, we epicutaneously sensitized the skin of mice with OVA in the presence and absence of δ-toxin and challenged the mice with OVA alone or OVA plus δ-toxin 3 weeks later. We found that δ-toxin triggered inflammatory skin disease including OVA-specific IgE and IgG1 production whereas challenge with OVA alone did not (FIG. 30).

Figure 4G:
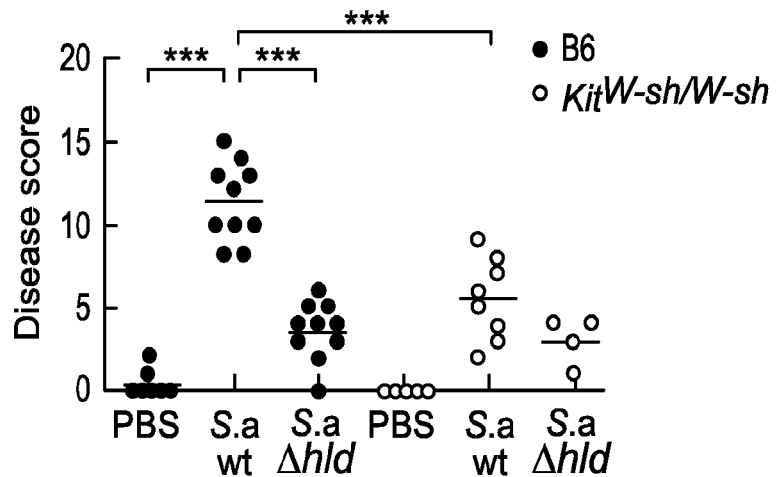
Figure 4H:
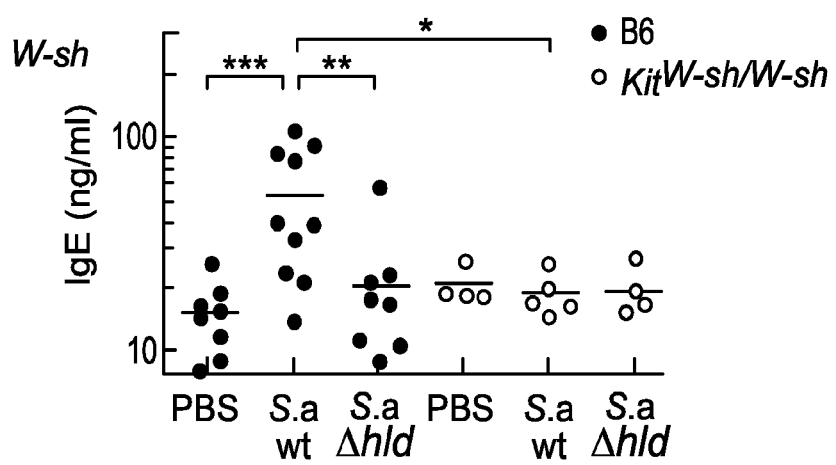

C57BL/6 mice colonized with wild-type S. aureus also developed higher serum IgE levels and more severe inflammatory skin disease than mice inoculated with S. aureus deficient in δ-toxin (FIGS. 4g and 4h). Importantly, MC-deficient $Kit^{W-sh/W-sh}$ mice inoculated with wild-type S. aureus showed reduced IgE serum levels and skin inflammation when compared to wild-type mice (FIGS. 4g and 4h). Adoptive transfer of MCs into the skin of $Kit^{W-sh/W-sh}$ mice restored skin disease and increase IgE production in mice colonized with wild-type, but not δ-toxin-deficient, S. aureus (FIGS. 4g, 4h, and 31). There were increased numbers of S. aureus and total bacteria in the skin of $Kit^{W-sh/W-sh}$ mice (FIG. 31), indicating that mast cells can regulate bacterial colonization under these experimental conditions. Microscopic analysis showed that the dermal MC densities in the skin of $Kit^{W-sh/W-sh}$ recipient mice were about 50% of those found in age-matched C57BL/6 mice (FIG. 31). Furthermore, toluidine-positive granules associated with MC degranulation were present in the skin of mice colonized with wild-type, but not δ-toxin-deficient, S. aureus (FIG. 31). Taken together, these results indicate that δ-toxin from S. aureus promotes allergic skin disease via activation of MCs.

Example 7

In order to generate antibodies immunospecific for δ-toxin, rabbits were immunized with a synthetic multiple antigenic peptide (MAP) immunogen containing sequence from the C-terminus of the S. aureus δ-toxin gene (IG-DLVKWIIDTVNKFTKK; (SEQ ID NO: 3)), linked to a helper T cell epitope from Plasmodium falciparum, referred to as T*(T star), which has the sequence: EYLNKIQNSL-STEWSPCSVT(SEQ ID NO: 9). Immune rabbits were bled and the serum was evaluated by ELISA for the presence of antibody specific for delta toxin. After confirmation that the serum contained the desired antibody, rabbit immunoglobulin was purified from the rabbit serum using Protein A. After performing a buffer exchange to replace the Tris buffer with PBS, the affinity-purified antibody was evaluated in an in vitro assay designed to assess the efficacy of the antibody to inhibit mast cell degranulation stimulated by full-length delta toxin.

Results showed that the delta-C-specific antibody is capable of inhibiting the production of hexosaminidase in a dose dependent fashion, while the control Ab does not have an inhibitory effect at any concentration.

The inhibition data from the dose-response data using the Delta-C rabbit antibody was plotted in a manner to allow determination, using 4-parameter linear regression, of the effective reciprocal dilution at which the production of hexosaminidase is at 50% of maximum (EC50). As shown in FIG. 2, the delta-C antibody has an EC50 of approximately 86. This value means that at a dilution of 1:86, the affinity purified antibody inhibits 50% of the hexosaminidase production.

Figure 12:
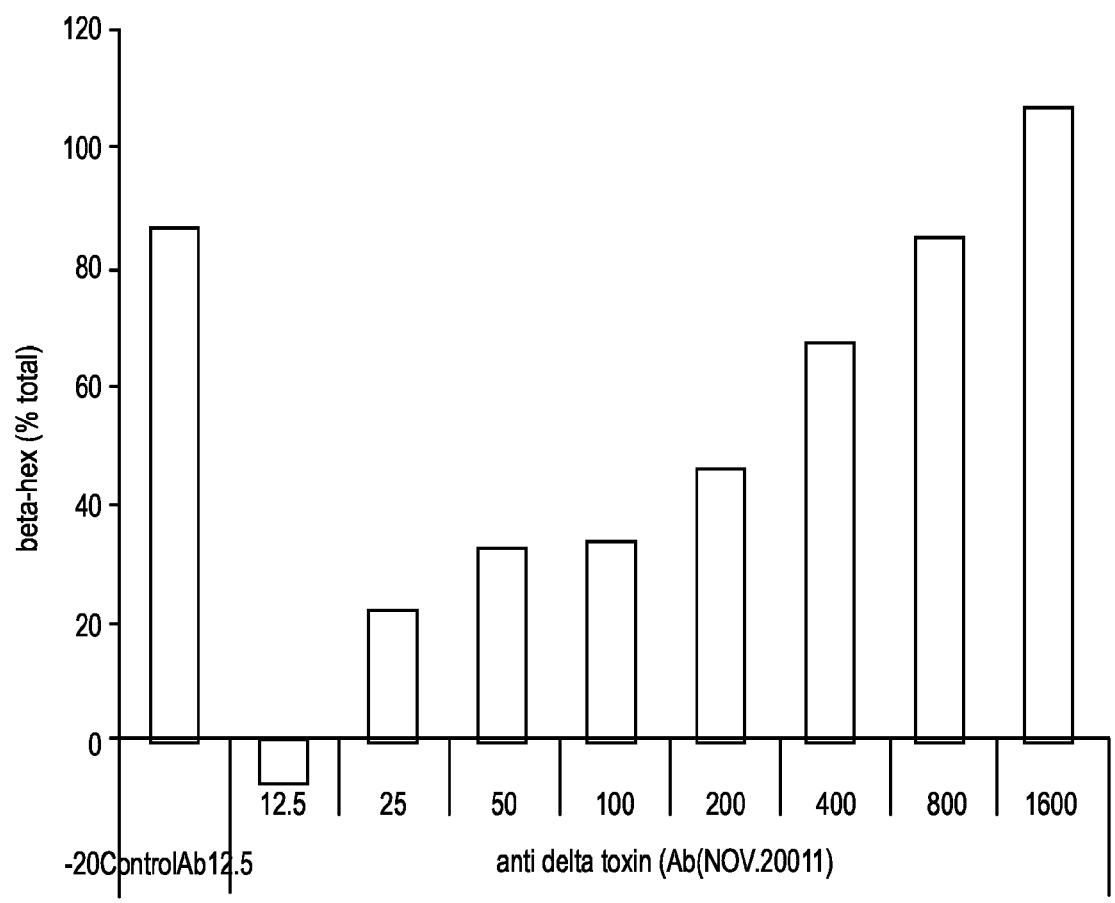
FIG. 12. a, b—pre-treatment of MCs with WRW4, a selective peptide antagonist of formyl peptide receptor-like 1 (FPRL1) that blocks human neutrophil activation induced by δ-toxin in vitro, inhibited MC degranulation induced by δ-toxin both in vitro and in vivo; c—Cyclosporin H, an antagonist of human FPR1, also partially inhibited mouse MC degranulation induced by δ-toxin.
Figure 14:
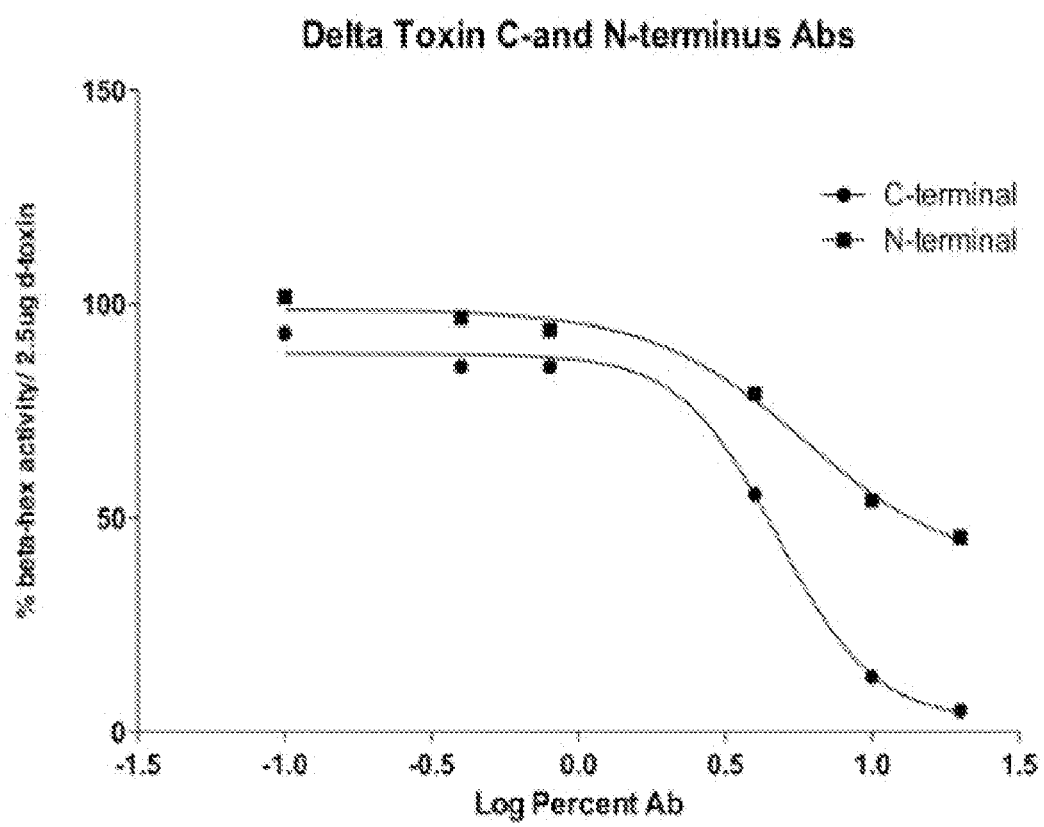
FIG. 14. Expression of hld was detected in the skin on day 4 after wild-type *S. aureus* colonization using a bioluminescent reporter *S. aureus* strain.

A repeat of the hexosaminidase assay using the affinity-purified rabbits antisera specific for the Delta-C immunogen demonstrated slightly more potent inhibition of hexosaminidase production compared to the first assay, as shown in FIGS. 3 and 12.

Antisera was also generated against a synthetic MAP that expressed sequence from the N-terminus of δ-toxin, MAQDIISTIGDLVKWIIDT (SEQ ID NO: 2) colinearly synthesized with an identical helper T cell epitope as the Delta-C immunogen. After affinity purification of the rabbit immunoglobulin, the antibody specific for the N-terminus of δ-toxin was evaluated side-by-side with the Delta-C antibody in the hexosaminidase assay. Both antibody preparations were adjusted to have the same antibody titer by ELISA before testing in the functional assay.

Data showed that rabbit antisera against the N-terminal-focused immunogen demonstrated efficacy to inhibit mast cell degranulation stimulated by delta toxin. FIG. 13. However, the N-terminal-focused antibody was found to be less potent than the Delta-C specific antibody. See FIG. 10, which shows the % beta hexosaminidase production produced by the mast cell line, MC/9, when stimulated with 1 μg/ml of synthetic delta toxin either in the absence of antibody or in the presence of control, affinity-purified rabbit antibody (Abl) or affinity purified rabbit antibody specific for the Delta-C immunogen. Also shown is the production of hexosaminidase in response to a control peptide (PSMalpha3). As is clear from the data, the delta-C-specific antibody is capable of inhibiting the production of hexosaminidase in a dose-dependent fashion, while the control Ab does not have an inhibitory effect at any concentration.

The inhibition data from the dose-response study using the Delta-C rabbit antibody can be plotted in a manner to allow determination, using 4-parameter linear regression, of the effective reciprocal dilution at which the production of hexosaminidase is at 50% of maximum (EC50). As shown in FIG. 11A, the delta-C antibody has an EC50 of approximately 86. This means that at a dilution of 1:86, the affinity-purified antibody inhibits 50% of the hexosaminidase production.

A repeat of the hexosaminidase assay using the affinity-purified rabbit antisera specific for the Delta-C immunogen demonstrated slightly more potent inhibition of hexosaminidase production compared to the first assay, as shown in FIG. 12 (shown along the x-axis are dilutions of affinity-purified Delta-C antibody).

Antisera was also generated against a synthetic MAP that expressed sequence from the N-terminus of delta toxin, MAQDIISTIGDLVKWIIDT (SEQ ID NO: 2), colinearly synthesized with an identical helper T cell epitope as the Delta-C immunogen. After affinity purification of the rabbit immunoglobulin, the antibody specific for the N-terminus of delta toxin was evaluated side-by-side with the Delta-C antibody in the hexosaminidase assay. Both antibody preparations were adjusted to have the same antibody titer by ELISA before testing in the functional assay.

As shown in FIG. 13, rabbit antisera raised against the N-terminal-focused immunogen demonstrates efficacy in inhibiting mast cell degranulation stimulated by delta toxin. However, the N-terminal-focused antibody appears less potent than the Delta-C specific antibody. An alternative expression of the data is shown in FIG. 14.

Each of the developed immunogens is capable of stimulating mast cell degranulation in vitro, with the Delta-C immunogen approximately 4× more potent at stimulating degranulation than the Delta-N immunogen. See FIG. 15. This increased ability of the Delta-C immunogen to stimulate mast cell degranulation is consistent with the observed increase in potency of antibodies to the Delta-C immunogen to inhibit hexosaminidase production and, hence, mast cell degranulation from MC/9 mast cells in vitro.

Example 8

In order to determine whether localized treatment with a δ-toxin antibody could mitigate mast cell degranulation in vivo, the following experiments were carried out.

One hour before culture supernatant challenge, 40 μl of either Delta-C Antibody, Control Antibody or PBS were injected into the ear (i.d.). One hour later, 40% Tryptic soy broth/PBS, or 40% *S. aureus* supernatant/PBS from overnight cultures of *S. aureus* were injected into the ear (i.d.). Mice were subsequently injected i.v. with 0.1 ml of saline containing 5 mg/ml Evans blue dye. Extravasation of Evans Blue dye was monitored for 15 minutes before photographs were acquired.

Results showed that local administration in the ears of C57BL/6 mice of *S. aureus* supernatant, which possesses high levels of mast cell degranulating activity in the form of delta toxin, develop blue ears as a result of the extravasation of Evans blue dye from capillaries. FIG. 9. Local treatment of the mice with the Delta-C antibody one hour prior to challenge with *S. aureus* supernatant completely mitigated the development of the blue ear, likely as a consequence of the antibody neutralization of delta toxin within the *S. aureus* supernatant. Control antibody can be observed to have a minimal effect on the development of the blue ear, while administration of medium only (negative control) does not cause dye extravasation or the development of the blue ear.

Example 9

*Staphylococcus aureus* pulse-field gel electrophoresis (PFGE) type USA300 transformed with a plasmid containing the P3 promoter followed by the luciferase gene (USA300-P3-Luc) was grown in tryptic soy broth (TSB) to mid-exponential stationary phase ($5\times10^8$ CFU/mL), as determined by optical density at 600 nm, from overnight cultured bacteria and harvested via centrifugation (4,000×g, 4° C., 5 minutes). Supernatant was removed and the bacterial pellet was washed twice with an equal volume of PBS. Bacteria were suspended in PBS at $5\times10^8$ CFU/mL, as confirmed by plating serial dilutions onto TSB. $2\times10^6$ CFU washed USA300-P3-Luc was incubated with wt USA300 8-hour filtered supernatant containing stimulatory auto-inducing peptide (AIP) at a final dilution of 1:10 and 40 μM each compound in a total of 40 μL/well of TSB on a 384-well plate. The *S. aureus* two-component agr system induces delta-toxin expression via expression of AIP at stationary growth phase and was used to stimulate activation of the P3 promoter. Alternatively, AIP produced by a different *S. aureus* strain, PFGE type USA400, acts to inhibit delta-toxin expression in USA300. As a positive control, samples were incubated with USA400 8-hour filtered supernatant containing inhibitory AIP at a final dilution of 1:10 instead of test compound. Samples were incubated at 37° C. for 2 hours, then analyzed for luminescence and optical density at 600 nm. Percent Inhibition was determined by the following formula:

$$\text{Percent inhibition} = 100 \times (\text{Lum}_{No\ inhibitor} - \text{Lum}_{compound}) / (\text{Lum}_{No\ Inhibitor} - \text{LUM}_{Positive\ control}).$$

Inhibitory compounds suitable for use in methods of inhibiting skin inflammation according to the disclosure were identified (Table 2) based on at least a 40% inhibition relative to the positive control, minimal reduction in growth as determined by optical density at 600 nm, and relatively low promiscuity (<10%) in relation to other high-throughput assays performed using these compounds.

TABLE 2

| % Inhibition | StDev* | Compounds that Inhibit RNAIII Induction | CCG_Number |
|---|---|---|---|
| 99.9 | 3.1 | HEXESTROL | CCG-39630 |
| 98.7 | 3.5 | SR 2640 | CCG-205156 |
| 97.9 | 2.9 | OCTOCRYLENE | EUSOLEX | CCG-213635 |
| 96.9 | 2.7 | ROBUSTIC ACID | CCG-39045 |
| 95.8 | 3.4 | CARNOSIC ACID | CCG-214849 |
| 90.9 | 2 | SODIUM MECLOFENAMATE | CCG-40117 |
| 90.8 | 2 | DIENESTROL | CCG-40189 |
| 89.5 | 2.2 | DICHLOROEVERNIC ACID | CCG-214058 |
| 87.8 | 4.1 | TPCK | CCG-213449 |
| 86.3 | 2.6 | CPD000466278_1H-Indole-2-propanoic acid, 1-[(4-chlorophenyl)methyl]-3-[(1,1-dimethylethyl)thio]-Alpha,Alpha-dimethyl-5-(1-methylethyl)- [CAS] | CCG-101053 |
| 85.7 | 2.6 | CPD000466395_RITONAVIR | CCG-101007 |
| 82.1 | 2 | AMINOETHOXYDIPHENYLBORANE | CCG-214123 |
| 81.6 | 1.6 | PYRETHRINS | DRIONE | CCG-212466 |
| 79.5 | 1.9 | Galangine | CCG-208629 |
| 78.9 | 1.9 | METHYL DEOXYCHOLATE | CCG-214200 |
| 76.1 | 1.4 | DANTRON | CCG-35470 |
| 76 | 2.1 | DIACERIN | CCG-40287 |
| 75.5 | 1.4 | PHENAZOPYRIDINE HYDROCHLORIDE | CCG-39935 |
| 75.3 | 1.8 | SMILAGENIN | CCG-38650 |
| 73.7 | 3.4 | 361549, GSK-3b Inhibitor VIII | CCG-206843 |
| 72.4 | 1.3 | PHENOLPHTHALEIN | CCG-39112 |
| 72.4 | 3.3 | Sulindac Sulfide | CCG-208108 |
| 71.9 | 1.8 | 2',4-DIHYDROXYCHALCONE | CCG-214400 |
| 71.3 | 2 | Lonidamine | CCG-204803 |
| 69.7 | 1.9 | CPD000469176_TIAGABINE HCl | CCG-100885 |
| 69.4 | 1.4 | CLOPIDOGREL SULFATE | CCG-39568 |
| 69.2 | 1.4 | FLUNIXIN MEGLUMINE | BANAMINE | CCG-213338 |
| 65.7 | 1.1 | TESTOSTERONE PROPIONATE | CCG-39107 |
| 65.1 | 1.7 | CPD000449318_Benzeneacetic acid, 2-[(2,6-dichlorophenyl)amino]-, monosodium salt [CAS] | CCG-100765 |
| 64.8 | 1.4 | ZOMEPIRAC SODIUM | CCG-39056 |
| 64.5 | 1.4 | APIGENIN DIMETHYL ETHER | CCG-214072 |
| 63.9 | 1.3 | NIFURSOL | CCG-213027 |
| 62.9 | 1.3 | HAEMATOXYLIN | CCG-38519 |
| 61.3 | 1.8 | URSOCHOLANIC ACID | CCG-38540 |
| 60.5 | 1.3 | GIBBERELLIC ACID | CCG-38588 |
| 60 | 1.2 | LUMIRACOXIB | PREXIGE | CCG-213068 |
| 59 | 1.4 | CPD000466283_Altanserin | CCG-101056 |
| 58.9 | 1.3 | MOXIDECTIN | CYDECTIN | CCG-213416 |
| 55.8 | 2.5 | 4Br-AHX | CCG-208771 |
| 55.8 | 1.4 | LUFENURON | PROGRAM | CCG-213976 |
| 55.7 | 1.1 | 3-DESHYDROXYSAPPANOL TRIMETHYL ETHER | CCG-38750 |
| 53.4 | 2.4 | XAV939 | CCG-208105 |
| 53.2 | 1.2 | CPD000466374_ORMETOPRIM | CCG-100900 |
| 52.8 | 1.1 | PANTOPRAZOLE | PROTONIX | CCG-213558 |
| 52.4 | 0.6 | NORETHINDRONE | CCG-40102 |
| 52.2 | 0.6 | DIHYDROERGOTAMINE MESYLATE | CCG-39548 |
| 51.9 | 0.6 | ERGOCALCIFEROL | CCG-38933 |
| 50.7 | 0.6 | DIBENZOTHIOPHENE | CCG-40229 |
| 49.9 | 2.2 | NCI16221 | CCG-208147 |
| 49 | 1 | CPD000466305_REPAGLINIDE | CCG-101013 |
| 48.7 | 1 | CPD000058555_LY 171883 | CCG-100826 |
| 47.8 | 0.8 | 5-CHLOROINDOLE-2-CARBOXYLIC ACID | CCG-39574 |

TABLE 2-continued

| % Inhibition | StDev* | Compounds that Inhibit RNAIII Induction | CCG_Number |
|---|---|---|---|
| 47.7 | 0.8 | CHLORANIL | CCG-39987 |
| 47.4 | 0.5 | DANAZOL | CCG-40338 |
| 47.2 | 0.8 | CHRYSOPHANOL | CCG-38348 |
| 46.5 | 0.4 | MEGESTROL ACETATE | CCG-40073 |
| 45.3 | 1.8 | SP 600125 | CCG-100672 |

*StDev = standard deviation

Example 10

Several S. aureus virulence factors are regulated by the global regulon agr+. The agr system is composed of two divergent operons designated P2 and P3. The P2 operon combines a density-sensing cassette (agrD and B) and a sensory transduction system composed of agrA and agrC. AgrA and agrC are required for autocatalytic activation of the promoter P2; they are also required for transcription from the divergent promoter P3. The S. aureus agr system ultimately acts through RNAIII, a 514-nucleotide transcript of the P3 operon. RNAIII encodes δ-toxin (hld), a 26-amino-acid peptide (SEQ ID NO:1). Delta-toxin and RNAIII stimulate the expression of post-exponentially expressed Staphylococcal extracellular toxins and enzymes. The inhibitory data disclosed in Example 9, coupled with the knowledge that the coding regions of δ-toxin and RNAIII overlap, and that δ-toxin and RNAIII have a regulatory influence over the deleterious exotoxins and enzymes that Staphylococcal species can elaborate, led to the realization that the inhibitors identified herein are useful not only in treating dermal inflammation, but in treating Staphylococcal colonization and, in particular, Staphylococcal infection. In an exemplary embodiment, a therapeutically effective amount of an inhibitory therapeutic identified in Table 2 is administered to a patient infected with S. aureus, such as a patient infected with MRSA (methicillin-resistant S. aureus).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the claimed subject matter are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the claimed subject matter and does not place a limitation on claim scope unless otherwise expressly indicated. No language in the specification should be construed as indicating any non-claimed element as essential to the practice of the invention.

Certain embodiments of this invention are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the claimed subject matter to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the claimed subject matter unless otherwise indicated herein or otherwise clearly contradicted by context.

What is claimed is:

1. A method for treating a staphylococcal disorder arising from mast cell-mediated cytokine release or mast cell degranulation due to *Staphylococcus* infection comprising the step of administering to an individual an amount of a compound therapeutically effective in inhibiting *Staphylococcus aureus* delta toxin.

2. The method of claim 1, wherein the staphylococcal disorder is skin inflammation arising from mast cell degranulation.

3. The method of claim 2 wherein the skin inflammation is dermatitis.

4. The method of claim 1 wherein the compound inhibits delta toxin activity.

5. The method of claim 4 wherein the compound binds delta toxin.

6. The method of claim 4 wherein the compound inhibits delta toxin interaction with mast cells.

7. The method of claim 4 wherein the compound inhibits delta toxin secretion or delta toxin expression.

8. The method of claim 1, wherein the compound is an anti-delta toxin antibody or antigen binding fragment thereof.

9. The method of claim 8, wherein the antibody or antigen binding fragment thereof is a polyclonal antibody, a monoclonal antibody, a humanized antibody, a chimeric antibody, a hybrid antibody, a single-chain antibody, a single chain Fv antibody, an Fab antibody, an Fab' antibody, an (Fab')$_2$, a diabody, or an antigen-binding fragment of a monoclonal antibody.

10. The method of claim 1 wherein the delta toxin comprises the sequence set forth in SEQ ID NO:1.

11. The method of claim 1, wherein the compound specifically binds a carboxy terminal region of the delta toxin (SEQ ID NO:3) or an amino terminal region of the delta toxin (SEQ ID NO:2).

12. The method of claim 1, wherein the compound is a delta toxin inhibitory RNA (RNAi) selected from the group consisting of an antisense RNA, a short hairpin RNA (shRNA), a small interfering RNA (siRNA), a microRNA (miRNA) and a ribozyme.

13. The method of claim 1 wherein the compound is selected from the group consisting of HEXESTROL; SR 2640; ROBUSTIC ACID; SODIUM MECLOFENAMATE; DIENESTROL; DICHLOROEVERNIC ACID; TPCK; CPD000466278_1H-Indole-2-propanoic acid, 1-[(4-chlorophenyl)methyl]-3-[(1,1-dimethylethyl)thio]-Alpha,Alpha-dimethyl-5-(1-methylethyl)- [CAS]; CPD000466395_RITONAVIR; AMINOETHOXYDIPHE-NYLBORANE; PYRETHRINS|DRIONE; Galangine; METHYL DEOXYCHOLATE; DANTRON; PHENAZOPYRIDINE HYDROCHLORIDE; SMI-LAGENIN; 361549, GSK-3b Inhibitor VIII; PHENOL-PHTHALEIN; Sulindac Sulfide; 2',4-DIHYDROXYCHAL-CONE; Lonidamine; CPD000469176_TIAGABINE HCl; CLOPIDOGREL SULFATE; FLUNIXIN MEGLUMINE-|BANAMINE; TESTOSTERONE PROPIONATE; CPD000449318_Benzeneacetic acid, 2-[(2,6-dichlorophenyl)amino]-, monosodium salt [CAS]; ZOMEPIRAC SODIUM; APIGENIN DIMETHYL ETHER; NIFURSOL; HAEMATOXYLIN; URSOCHOLANIC ACID; GIBBER-ELLIC ACID; LUMIRACOXIB|PREXIGE; CPD000466283 Altanserin; MOXIDECTIN|CYDECTIN; 4Br-AHX; LUFENURON|PROGRAM; 3-DESHYDROX-YSAPPANOL TRIMETHYL ETHER; XAV939; CPD000466374_ORMETOPRIM; PANTOPRA-ZOLE|PROTONIX; NORETHINDRONE; DIHYDROER-GOTAMINE MESYLATE; ERGOCALCIFEROL; DIBEN-ZOTHIOPHENE; NCI16221; CPD000466305_REPAGLINIDE; CPD000058555_LY 171883; 5-CHLOROINDOLE-2-CARBOXYLIC ACID; CHLORANIL; DANAZOL; CHRYSOPHANOL; MEGESTROL ACETATE; and SP 600125.

14. The method of claim 13 wherein the compound is selected from the group consisting of HEXESTROL; SR 2640; ROBUSTIC ACID; SODIUM MECLOFENAMATE; DIENESTROL; DICHLOROEVERNIC ACID; and TPCK.

15. The method of claim 1 consisting essentially of the step of administering to an individual an amount of a compound therapeutically effective in inhibiting *Staphylococcus aureus* delta toxin.

16. The method of claim 15, wherein the staphylococcal disorder is skin inflammation arising from mast cell degranulation.

17. The method of claim 16 wherein the skin inflammation is dermatitis.

18. The method of claim 15 wherein the compound binds delta toxin.

19. The method of claim 15 wherein the compound inhibits delta toxin interaction with mast cells, inhibits delta toxin secretion, or inhibits delta toxin expression.

20. The method of claim 15 wherein the compound is selected from the group consisting of HEXESTROL; SR 2640; ROBUSTIC ACID; SODIUM MECLOFENAMATE; DIENESTROL; DICHLOROEVERNIC ACID; TPCK; CPD000466278_1H-Indole-2-propanoic acid, 1-[(4-chlorophenyl)methyl]-3-[(1,1-dimethylethyl)thio]-Alpha,Alpha-dimethyl-5-(1-methylethyl)- [CAS]; CPD000466395_RITONAVIR; AMINOETHOXYDIPHENYLBORANE; PYRETHRINS|DRIONE; Galangine; METHYL DEOXYCHOLATE; DANTRON; PHENAZOPYRIDINE HYDROCHLORIDE; SMILAGENIN; 361549, GSK-3b Inhibitor VIII; PHENOLPHTHALEIN; Sulindac Sulfide; 2',4-DIHYDROXYCHALCONE; Lonidamine; CPD000469176_TIAGABINE HCl; CLOPIDOGREL SULFATE; FLUNIXIN MEGLUMINE|BANAMINE; TESTOSTERONE PROPIONATE; CPD000449318_Benzeneacetic acid, 2-[(2,6-dichlorophenyl)amino]-, monosodium salt [CAS]; ZOMEPIRAC SODIUM; APIGENIN DIMETHYL ETHER; NIFURSOL; HAEMATOXYLIN; URSOCHOLANIC ACID; GIBBERELLIC ACID; LUMIRACOXIB|PREXIGE; CPD000466283_Altanserin; MOXIDECTIN|CYDECTIN; 4Br-AHX; LUFENURON|PROGRAM; 3-DESHYDROXYSAPPANOL TRIMETHYL ETHER; XAV939; CPD000466374_ORMETOPRIM; PANTOPRAZOLE|PROTONIX; NORETHINDRONE; DIHYDROERGOTAMINE MESYLATE; ERGOCALCIFEROL; DIBENZOTHIOPHENE; NCI16221; CPD000466305_REPAGLINIDE; CPD000058555_LY 171883; 5-CHLOROINDOLE-2-CARBOXYLIC ACID; CHLORANIL; DANAZOL; CHRYSOPHANOL; MEGESTROL ACETATE; and SP 600125.

21. The method of claim 17 wherein the skin dermatitis is neurodermatitis.

22. The method of claim 17, wherein the skin inflammation arises from mast cell-mediated cytokine release.

23. A method of treating a *Staphylococcus aureus* infection comprising administering to an individual an amount of a compound therapeutically effective in inhibiting *Staphylococcus aureus* delta toxin activity.

24. The method of claim 23 wherein the *S. aureus* is a methicillin-resistant *S. aureus* (MRSA).

25. The method of claim 23 wherein the compound is an anti-delta toxin antibody or antigen binding fragment thereof.

26. The method of claim 25 wherein the antibody or antigen binding fragment thereof is a humanized antibody, a chimeric antibody, a hybrid antibody, a single-chain antibody, a single chain Fv antibody, an Fab antibody, an Fab' antibody, an (Fab')$_2$, a diabody, or an antigen-binding fragment of a monoclonal antibody.

27. The method of claim 25 wherein the antibody or antigen binding fragment thereof binds a carboxy-terminal region of delta toxin (SEQ ID NO:3) or an N-terminal region of delta toxin (SEQ ID NO:2).

28. The method of claim 23 wherein the compound is a polynucleotide selected from the group consisting of a delta toxin antisense oligonucleotide, a delta toxin inhibitory RNA (RNAi), a delta toxin short hairpin RNA (shRNA), a delta toxin small interfering RNA (siRNA), a delta toxin microRNA (miRNA) and a ribozyme interacting with a delta toxin transcript.

29. The method of claim 23 wherein the compound is selected from the group consisting of HEXESTROL; SR 2640; ROBUSTIC ACID; SODIUM MECLOFENAMATE; DIENESTROL; DICHLOROEVERNIC ACID; TPCK;
CPD000466278_1H-Indole-2-propanoic acid, 1-[(4-chlorophenyl)methyl]-3-[(1,1-dimethylethyl)thio]-Alpha, Alpha-dimethyl-5-(1-methylethyl)- [CAS]; CPD000466395_RITONAVIR; AMINOETHOXYDIPHENYLBORANE; PYRETHRINS|DRIONE; Galangine; METHYL DEOXYCHOLATE; DANTRON; PHENAZOPYRIDINE HYDROCHLORIDE; SMILAGENIN; 361549, GSK-3b Inhibitor VIII; PHENOLPHTHALEIN; Sulindac Sulfide; 2',4-DIHYDROXYCHALCONE; Lonidamine; CPD000469176_TIAGABINE HCl; CLOPIDOGREL SULFATE; FLUNIXIN MEGLUMINE|BANAMINE; TESTOSTERONE PROPIONATE; CPD000449318_Benzeneacetic acid, 2-[(2,6-dichlorophenyl)amino]-, monosodium salt [CAS]; ZOMEPIRAC SODIUM; APIGENIN DIMETHYL ETHER; NIFURSOL; HAEMATOXYLIN; URSOCHOLANIC ACID; GIBBERELLIC ACID; LUMIRACOXIB|PREXIGE;
CPD000466283_Altanserin; MOXIDECTIN|CYDECTIN; 4Br-AHX; LUFENURON|PROGRAM; 3-DESHYDROXYSAPPANOL TRIMETHYL ETHER; XAV939; CPD000466374_ORMETOPRIM; PANTOPRAZOLE|PROTONIX; NORETHINDRONE; DIHYDROERGOTAMINE MESYLATE; ERGOCALCIFEROL; DIBENZOTHIOPHENE; NCI16221; CPD000466305_REPAGLINIDE;
CPD000058555_LY 171883; 5-CHLOROINDOLE-2-CARBOXYLIC ACID; CHLORANIL; DANAZOL; CHRYSOPHANOL; MEGESTROL ACETATE; and SP 600125.

30. The method of claim 29 wherein the compound is selected from the group consisting of HEXESTROL; SR 2640; ROBUSTIC ACID; SODIUM MECLOFENAMATE; DIENESTROL; DICHLOROEVERNIC ACID; and TPCK.

* * * * *